United States Patent
Brocke et al.

(10) Patent No.: US 11,964,933 B2
(45) Date of Patent: *Apr. 23, 2024

(54) FLUORINATED AROMATIC COMPOUNDS

(71) Applicant: Merck Patent GmbH, Darmstadt (DE)

(72) Inventors: Constanze Brocke, Darmstadt (DE);
Dmitry Ushakov, Darmstadt (DE);
Carsten Fritzsch, Darmstadt (DE);
Dagmar Klass, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 87 days.

This patent is subject to a terminal disclaimer.

(21) Appl. No.: 17/767,080

(22) PCT Filed: Oct. 8, 2020

(86) PCT No.: PCT/EP2020/078195
§ 371 (c)(1),
(2) Date: Apr. 7, 2022

(87) PCT Pub. No.: WO2021/069535
PCT Pub. Date: Apr. 15, 2021

(65) Prior Publication Data
US 2023/0025385 A1     Jan. 26, 2023

(30) Foreign Application Priority Data
Oct. 10, 2019 (EP) .................... 19202339

(51) Int. Cl.
G02F 1/1333     (2006.01)
C07C 331/28    (2006.01)
C07C 331/30    (2006.01)
C09K 19/04     (2006.01)

(52) U.S. Cl.
CPC .......... *C07C 331/28* (2013.01); *C07C 331/30* (2013.01); *C09K 19/0403* (2013.01); *C07C 2601/14* (2017.05); *C07C 2601/16* (2017.05); *C09K 2019/0444* (2013.01); *C09K 2219/11* (2013.01)

(58) Field of Classification Search
CPC .... C09K 19/0403; C09K 19/04; C09K 19/12; C09K 19/18; C09K 2019/0444; C09K 2019/123; C09K 2019/183; C09K 2219/11; C07C 331/28; C07C 331/30; C07C 2601/14; C07C 2601/16; G02F 1/1333
See application file for complete search history.

(56) References Cited

U.S. PATENT DOCUMENTS

| 7,361,288 B2 | 4/2008 | Lüssem et al. |
| 9,567,214 B2 | 2/2017 | Zhou et al. |
| 9,593,279 B2 * | 3/2017 | Wittek ...................... H01Q 1/36 |
| 10,711,197 B2 | 7/2020 | Wittek et al. |
| 2023/0025385 A1 * | 1/2023 | Brocke ................. C07C 331/30 |
| 2023/0104326 A1 * | 4/2023 | Brocke ............. C09K 19/3098 |
| | | 252/299.63 |

FOREIGN PATENT DOCUMENTS

| DE | 102004029429 B4 | 4/2019 | |
| EP | 1054001 B1 | 7/2003 | |
| EP | 2982730 B1 | 10/2019 | |
| JP | 2002012871 A | 1/2002 | |
| JP | 2005120208 A | 5/2005 | |
| WO | 2014116238 A1 | 7/2014 | |
| WO | WO-2022207584 A2 * | 10/2022 | ............. C09K 19/04 |
| WO | WO-2022229124 A1 * | 11/2022 | ............. C09K 19/04 |

OTHER PUBLICATIONS

International Search report PCT/EP2020/078195 dated Dec. 23, 2020 (pp. 1-3).

* cited by examiner

*Primary Examiner* — Geraldina Visconti
(74) *Attorney, Agent, or Firm* — MILLEN, WHITE, ZELANO & BRANIGAN, P.C.; Csaba Henter

(57) ABSTRACT

The present invention relates to aromatic isothiocyanates of formula U

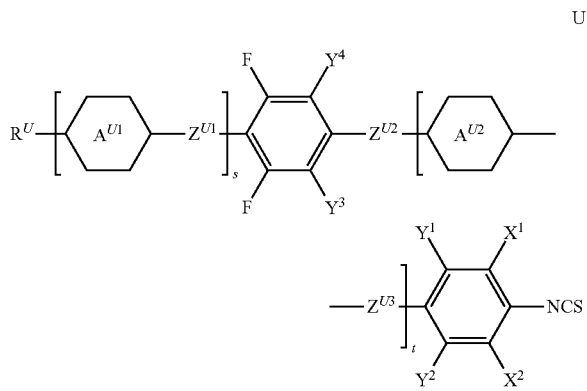

as defined in claim 1, to liquid-crystalline media comprising one or more compounds of formula U and to high-frequency components comprising these media, especially microwave components for high-frequency devices, such as devices for shifting the phase of microwaves, tunable filters, tunable metamaterial structures, and electronic beam steering antennas, e.g. phased array antennas.

20 Claims, No Drawings

FLUORINATED AROMATIC COMPOUNDS

The present invention relates to fluorinated aromatic compounds, liquid-crystalline media comprising same, and to high-frequency components comprising these media, especially microwave components for high-frequency devices, such as devices for shifting the phase of microwaves, tunable filters, tunable metamaterial structures, and electronic beam steering antennas (e.g. phased array antennas), and to said devices.

Liquid-crystalline media have a been used for many years in electro-optical displays (liquid crystal displays: LCDs) in order to display information. More recently, however, liquid-crystalline media have also been proposed for use in components for microwave technology, such as, for example, in DE 10 2004 029 429.1 A and in JP 2005-120208 (A).

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (Merck KGaA, Germany).

DE 10 2004 029 429 A describes the use of liquid-crystal media in microwave technology, inter alia in phase shifters. Therein, liquid-crystalline media with respect to their properties in the corresponding frequency range have been discussed and liquid-crystalline media based on mixtures of mostly aromatic nitriles and isothiocyanates have been shown.

In EP 2 982 730 A1, mixtures are described that completely consist of isothiocyanate compounds.

Fluorine atoms are commonly used in mesogenic compounds to introduce polarity. Especially in combination with a terminal NCS group high dielectric anisotropy values can be achieved, in particular when a NCS group in the 1-position has two fluorine atoms in its ortho positions as the overall molecular dipole is the sum of all individual dipoles of a molecule's partial structures. A well balanced compromise with respect to the number of fluorine atoms has to be found as fluorine substitution often has a negative influence in the nematic phase properties of a compound.

The liquid-crystalline compositions available for the use in microwave applications are still afflicted with several disadvantages. It is required to improve these media with respect to their general physical properties, the shelf life and the stability under operation in a device. In view of the multitude of different parameters which have to be considered and improved for the development of liquid crystalline media for microwave application it is desirable to have a broader range of possible mixture components for the development of such liquid-crystalline media.

An object of the present invention is to provide a compound for the use in liquid crystalline media with improved properties relevant for the application in the microwave range of the electromagnetic spectrum.

To solve the problem, a compound of formula U shown below is provided and a liquid crystalline medium comprising the compound.

The present invention relates to a compound of formula U

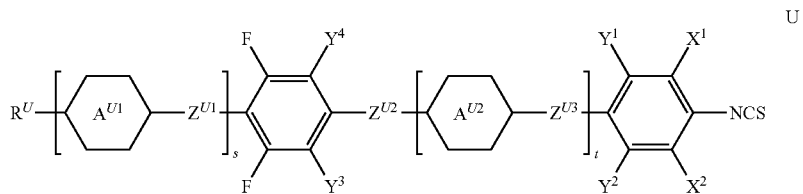

in which $R^U$ denotes H, alkyl or alkoxy having 1 to 12 C atoms, or alkenyl, alkenyloxy or alkoxyalkyl having 2 to 12 C atoms, in which one or more $CH_2$-groups may be replaced by

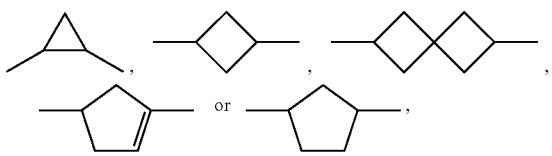

or a group $R^P$, $R^P$ denotes halogen, CN, NCS, $R^F$, $R^F$—O— or $R^F$—S—, wherein $R^F$ denotes fluorinated alkyl or fluorinated alkenyl having up to 9 C atoms, $Z^{U1}$, $Z^{U2}$, $Z^{U3}$ identically or differently, denote —CH=CH—, —CF=CF—, —CH=CF—, —CF=CH—, —C≡C— or a single bond, preferably —C≡C— or a single bond, $X^1$, $X^2$ identically or differently, denote H, Cl, F, $CH_3$ or $C_2H_5$, preferably H or F, $Y^1$, $Y^2$, $Y^3$, $Y^4$, identically or differently, denote H, F, Cl, or straight chain or branched or cyclic alkyl, alkenyl, alkoxy or alkenyloxy, each having up to 12 C atoms, where at least one of $Y^1$, $Y^2$, $Y^3$ and $Y^4$ is different from F, s is 0, 1 or 2, preferably 0 or 1, t is 0, 1 or 2, preferably 0 or 1, and s+t is 0, 1 or 2, preferably 0 or 1,

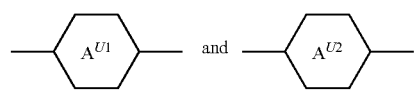

denote a radical selected from the following groups:
a) the group consisting of 1,4-phenylene, 1,4-naphthylene, and 2,6-naphthylene, in which one or two CH groups may be replaced by N and in which one or more H atoms may be replaced by L,
b) the group consisting of trans-1,4-cyclohexylene, 1,4-cyclohexenylene, bicyclo[1.1.1]pentane-1,3-diyl, 4,4"-bicyclohexylene, bicyclo[2.2.2]octane-1,4-diyl, spiro

[3.3]heptane-2,6-diyl, in which one or more non-adjacent CH$_2$ groups may be replaced by —O— and/or —S— and in which one or more H atoms may be replaced by F, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms.

The present invention further relates to a compound of formula UN

These properties as a whole make the media particularly suitable for use in components and devices for high-frequency technology and applications in the microwave range, in particular devices for shifting the phase of microwaves, tunable filters, tunable metamaterial structures, and electronic beam steering antennas (e.g. phased array antennas).

Herein, "high-frequency technology" is taken to mean applications of electromagnetic radiation having frequencies in the range of from 1 MHz to 1 THz, preferably from 1 GHz to 500 GHz, more preferably 2 GHz to 300 GHz, particularly preferably from about 5 GHz to 150 GHz.

As used herein, halogen is F, Cl, Br or I, preferably F or Cl, particularly preferably F.

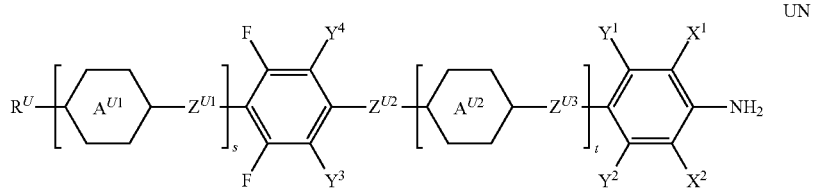

in which the groups and parameter have the meanings given above for formula U.

According to another aspect of the present invention there is provided a process for the synthesis of compounds of formula U from compounds of formula UN given below.

The present invention further relates to a liquid-crystalline medium comprising a compound of formula U and to the use of a liquid-crystalline medium comprising a compound of formula U in a component for high-frequency technology.

According to yet another aspect of the present invention there is provided a component and a device comprising said component, both operable in the microwave region of the electromagnetic spectrum. Preferred components are phase shifters, varactors, wireless and radio wave antenna arrays, matching circuits and adaptive filters.

Preferred embodiments of the present invention are subject-matter of the dependent claims or can be taken from the description.

Surprisingly, it has been found that it is possible to achieve liquid-crystalline media having excellent stability and at the same time a high dielectric anisotropy, suitably fast switching times, a suitable, nematic phase range, high tunability and low dielectric loss, by using compounds of formula U in liquid-crystalline media. In particular, the use of compounds of formula U enable liquid crystal media with reduced dielectric loss without or insignificant negative influence on other relevant parameters such as inter alia nematic phase range, dielectric anisotropy or tunability.

The media according to the present invention are distinguished by a high clearing temperature, a broad nematic phase range and excellent low-temperature stability (LTS). As a result, devices containing the media are operable under extreme temperature conditions.

The media are further distinguished by high values of the dielectric anisotropy and low rotational viscosities. As a result, the threshold voltage, i.e. the minimum voltage at which a device is switchable, is very low. A low operating voltage and low threshold voltage is desired in order to enable a device having improved switching characteristics and high energy efficiency. Low rotational viscosities enable fast switching of the devices according to the invention.

Herein, alkyl is straight-chain or branched or cyclic and has 1 to 15 C atoms, is preferably straight-chain and has, unless indicated otherwise, 1, 2, 3, 4, 5, 6 or 7 C atoms and is accordingly preferably methyl, ethyl, n-propyl, n-butyl, n-pentyl, n-hexyl or n-heptyl.

Herein, branched alkyl is preferably isopropyl, s-butyl, isobutyl, isopentyl, 2-methylhexyl or 2-ethylhexyl.

As used herein, cyclic alkyl is taken to mean straight chain or branched alkyl or alkenyl having up to 12 C atoms, preferably alkyl having 1 to 7 C atoms, in which a group CH$_2$ is replaced with a carbocyclic ring having 3 to 5 C atoms, very preferably selected from the group consisting of cyclopropylalkyl, cyclobutylalkyl, cyclopentylalkyl and cyclopentenylalkyl.

Herein, an alkoxy radical is straight-chain or branched and contains 1 to 15 C atoms. It is preferably straight-chain and has, unless indicated otherwise, 1, 2, 3, 4, 5, 6 or 7 C atoms and is accordingly preferably methoxy, ethoxy, n-propoxy, n-butoxy, n-pentoxy, n-hexoxy or n-heptoxy.

Herein, an alkenyl radical is preferably an alkenyl radical having 2 to 15 C atoms, which is straight-chain or branched and contains at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl. If the two C atoms of the C—C double bond are substituted, the alkenyl radical can be in the form of E and/or Z isomer (trans/cis). In general, the respective E isomers are preferred. Of the alkenyl radicals, prop-2-enyl, but-2- and -3-enyl, and pent-3- and -4-enyl are particularly preferred.

Herein, alkynyl is taken to mean an alkynyl radical having 2 to 15 C atoms, which is straight-chain or branched and contains at least one C—C triple bond. 1- and 2-propynyl and 1-, 2- and 3-butynyl are preferred.

In case R$^F$ denotes a halogenated alkyl-, alkoxy-, alkenyl or alkenyloxy it can be branched or unbranched. Preferably it is unbranched, mono-poly or perfluorinated, more preferably perfluorinated and has 1, 2, 3, 4, 5, 6 or 7 C atoms, in case of alkenyl 2, 3, 4, 5, 6 or 7 C atoms.

$R^P$ preferably denotes CN, NCS, Cl, F, —$(CH_2)_n$—CH=$CF_2$, —$(CH_2)_n$—CH=CHF, —$(CH_2)_n$—CH=$Cl_2$, —$C_nF_{2n+1}$, —$(CF_2)_n$—$CF_2H$, —$(CH_2)_n$—$CF_3$, —$(CH_2)_n$—$CHF_2$, —$(CH_2)_nCH_2F$, —CH=$CF_2$, —$O(CH_2)_n$—CH=$CF_2$, —$O(CH_2)_nCHCl_2$, —$OC_nF_{2n+1}$, —$O(CF_2)_n$—$CF_2H$, —$O(CH_2)_nCF_3$, —$O(CH_2)_n$—$CHF_2$, —$O(CF)_nCH_2F$, —OCF=$CF_2$, —$SC_nF_{2n+1}$, —$S(CF)_n$—$CF_3$, wherein n is an integer from 0 to 7.

The compounds of the general formula U are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for said reactions. Use can be made here of variants which are known per se, but are not mentioned here in greater detail.

If desired, the starting materials can also be formed in situ by not isolating them from the reaction mixture, but instead immediately converting them further into the compounds of the general formula U.

Preferred synthetic pathways towards compounds according to the invention are exemplified in the schemes below, and are further illustrated by means of the working examples.

Preferred intermediates are 5-bromo-1,3-difluoro-2-alkyl-benzenes which can be reacted to give compounds of the formula UN for example by cross coupling reactions commonly known as Suzuki, Stille, Sonogashira reactions, and the like. Preferred pathways are exemplified in schemes 1 and 2, in which the groups and parameters have the meanings defined in claim 1.

Scheme 1

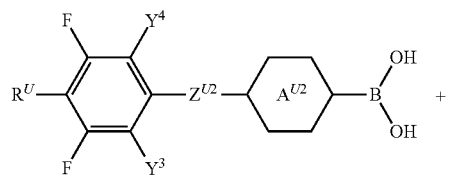

Scheme 2

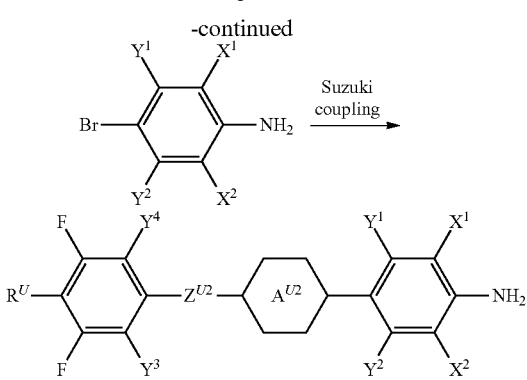

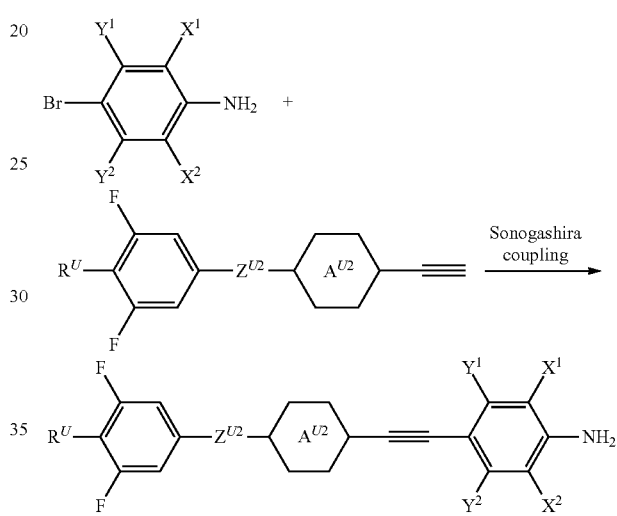

Preferred reagents for the process according to the invention for the transformation of compounds of the formula UN into compounds of the formula U (scheme 3) are carbon disulfide, thiophosgene, thiocarbonyl diimidazole, di-2-pyridyl thionocarbonate, bis(dimethylthiocarbamoyl) disulfide, dimethylthiocarbamoyl chloride and phenyl chlorothionoformate, very preferably thiophosgene.

Scheme 3

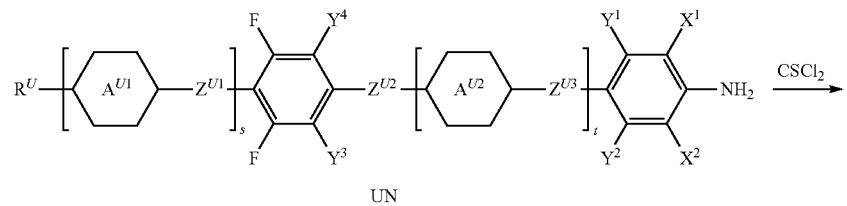

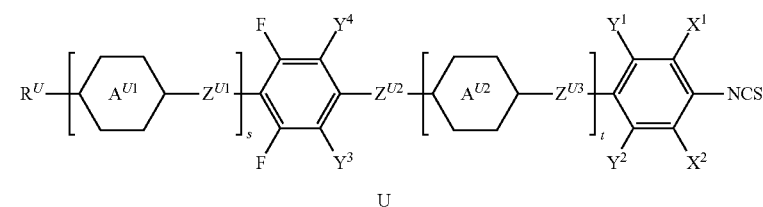

The described reactions should only be regarded as illustrative. The person skilled in the art can carry out corresponding variations of the syntheses described and also follow other suitable synthetic routes in order to obtain compounds of the formula U.

The compounds of formula U are preferably selected from the compounds in which the groups

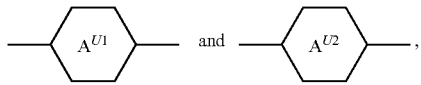

identically or differently, denote

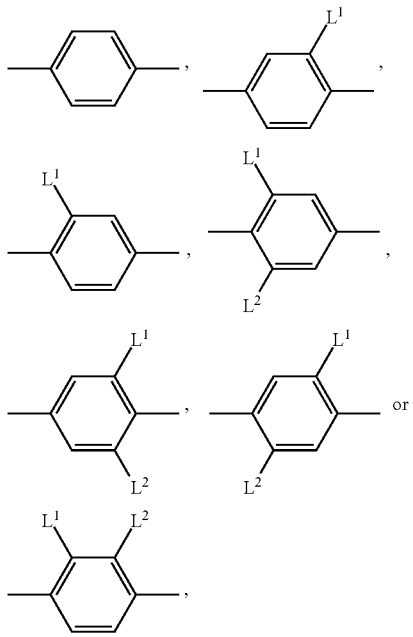

in which one or two CH-groups may be replaced by N, and wherein

alternatively denotes

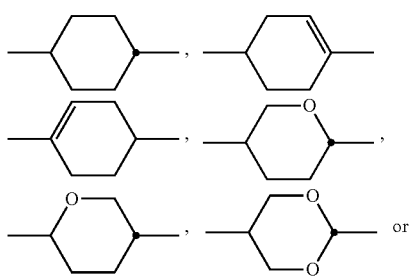

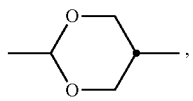

and

L$^1$ and L$^2$ identically or differently, denote F, Cl or straight chain or branched or cyclic alkyl or alkenyl each having up to 12 C atoms, and where the other groups and parameters have the meanings given above.

In a preferred embodiment of the present invention, the compounds of formula U are selected from the compounds of the formulae U-1 to U-20, very preferably from the compounds of the formulae U-1 to U13:

U-1
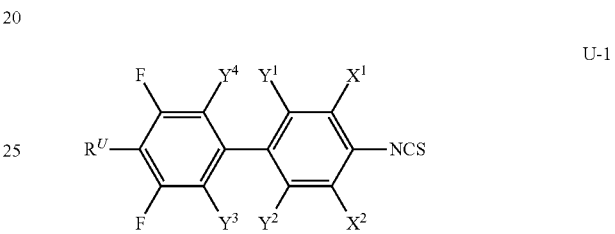

U-2
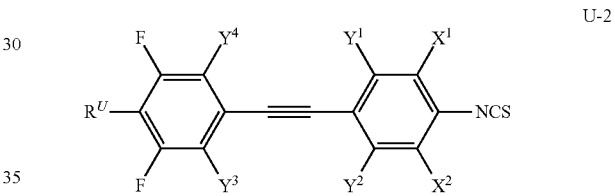

U-3
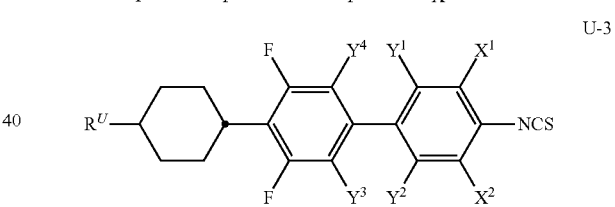

U-4
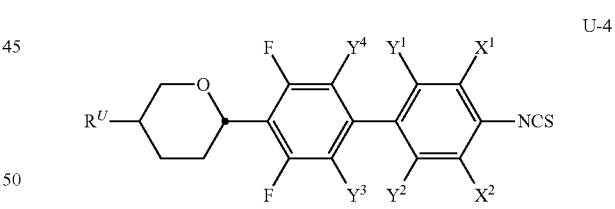

U-5
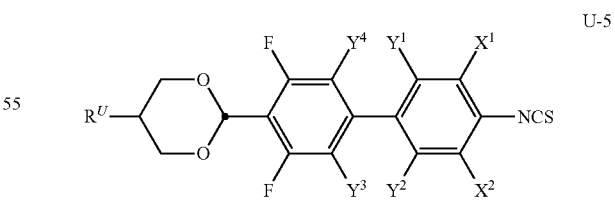

U-6
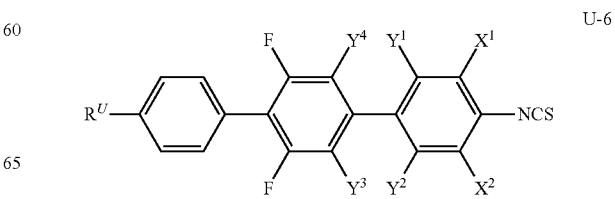

U-7
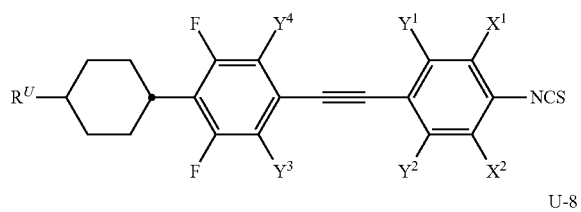

U-8
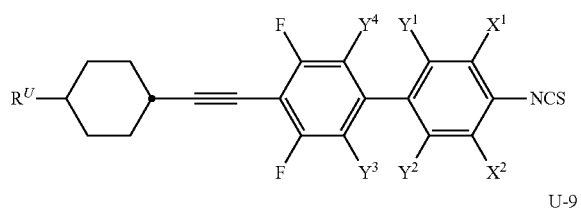

U-9
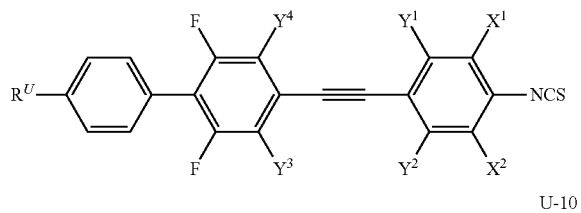

U-10
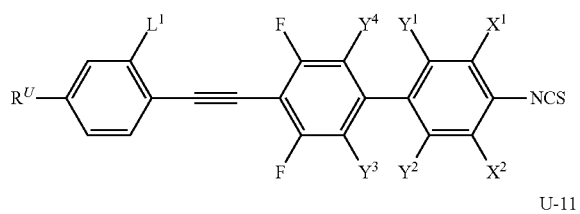

U-11
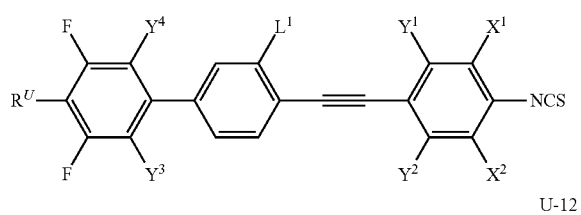

U-12
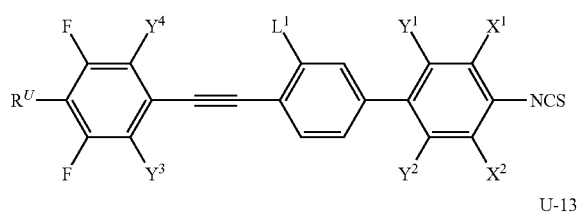

U-13
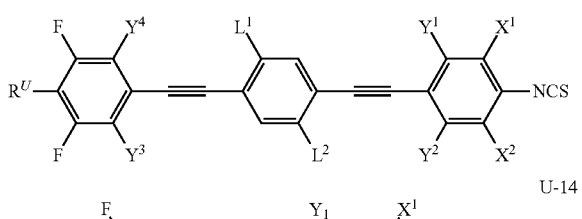

U-14
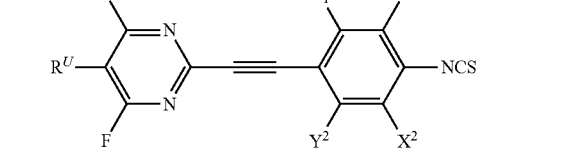

U-15
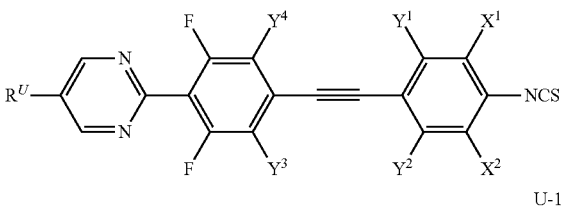

U-16
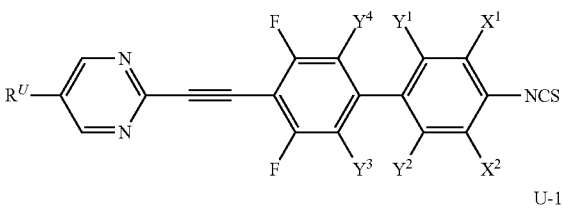

U-17
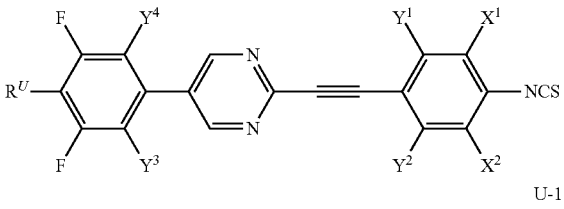

U-18
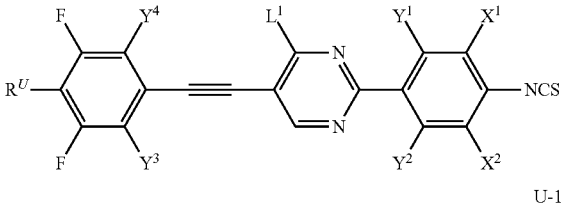

U-19
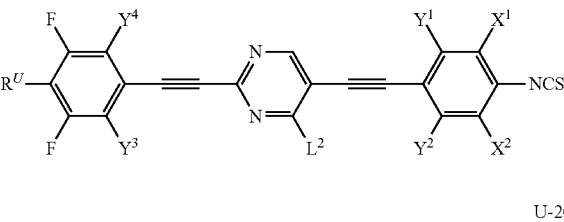

U-20
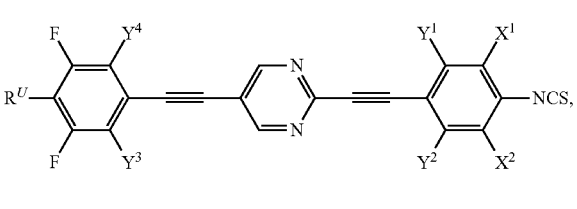

in which the occurring groups have the meanings indicated above for formula U and its subformulae and preferably $R^U$ denotes alkyl having 1 to 7 C atoms, $Y^1$, $Y^2$, $Y^3$, and $Y^4$, identically or differently, denote H, F, Cl, methyl, ethyl, n-propyl, isopropyl, cyclopropyl, cyclobutyl, cyclopentyl or cyclopentenyl, and more preferably $Y^1$ and $Y^2$ independently denote H or F, in particular H, and $Y^3$ and $Y^4$ very preferably denote H, and L and $L^2$, identically or differently, very preferably denote H, F, methyl or ethyl, in particular H.

According to one embodiment of the present invention there are provided compounds of formula U in which $R^U$ denotes H, alkyl or alkoxy having 1 to 12 C atoms, or alkenyl, alkenyloxy or alkoxyalkyl having 2 to 12 C atoms, in which one or more $CH_2$-groups may be replaced by

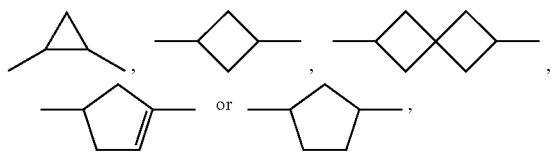

preferably alkyl having 1 to 12 C atoms.

According to another embodiment of the present invention there are provided compounds of formula U in which the group $R^U$ denotes $R^P$, where $R^P$ denotes halogen, CN, NCS, $R^F$, $R^F$—O— or $R^F$—S—, and wherein $R^F$ denotes fluorinated alkyl or fluorinated alkenyl having up to 9 C atoms, preferably $CF_3$ or $OCF_3$.

In a preferred embodiment of the present invention the medium comprises one or more compounds selected from the group of compounds of the formulae I, II and III,

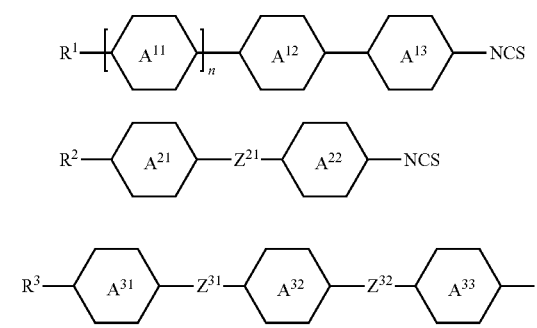

in which $R^1$ denotes H, unfluorinated alkyl or unfluorinated alkoxy having 1 to 17, preferably 3 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

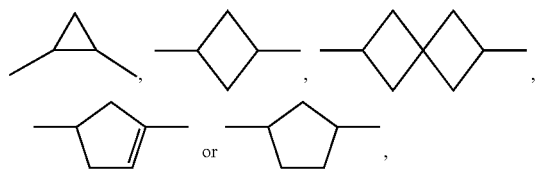

preferably unfluorinated alkyl or unfluorinated alkenyl, n is 0, 1 or 2,

to

on each occurrence, independently of one another, denote

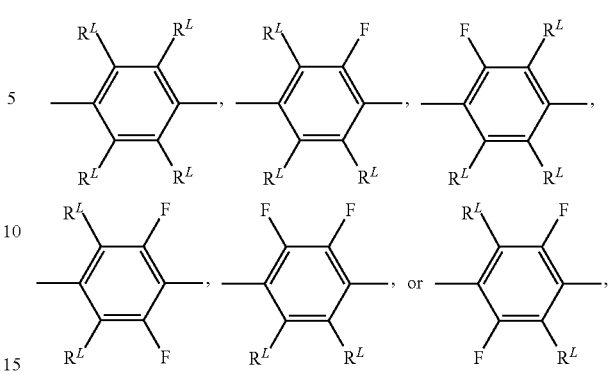

in which $R^L$, on each occurrence, identically or differently, denotes H or alkyl having 1 to 6 C atoms, preferably H, methyl or ethyl, particularly preferably H, and wherein

alternatively denotes

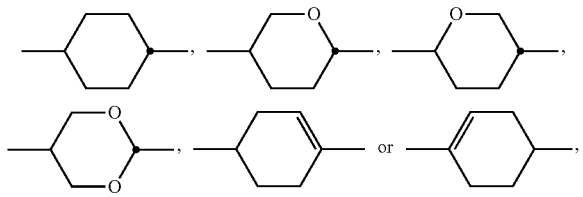

preferably

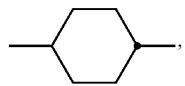

and in case n=2, one of

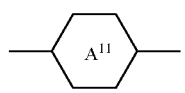

preferably denotes

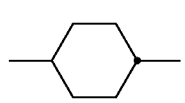

and the other preferably denotes

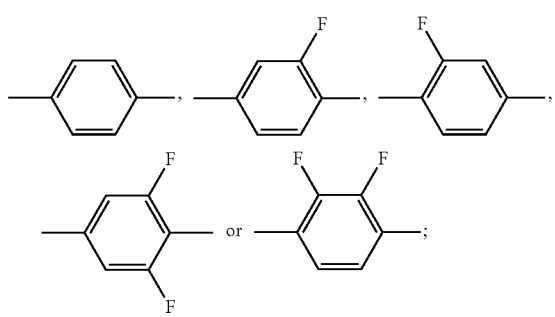

and
 preferably

to

independently of one another, denote

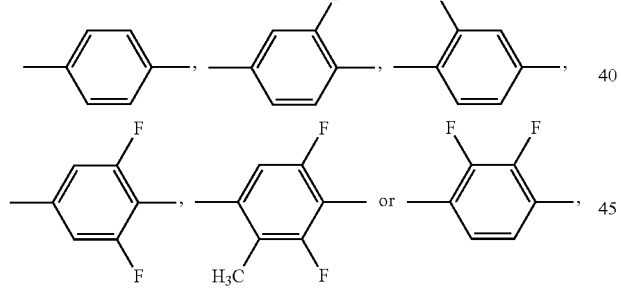

more preferably

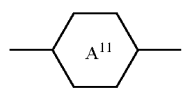

denotes

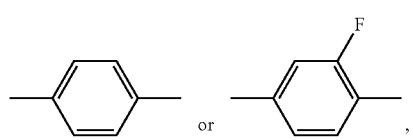

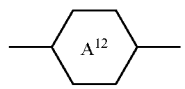

denotes

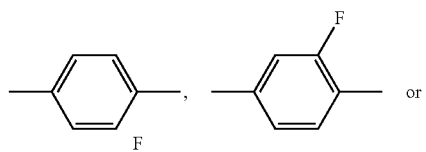

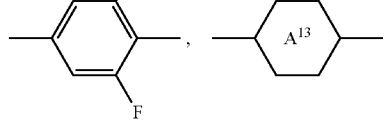

denotes

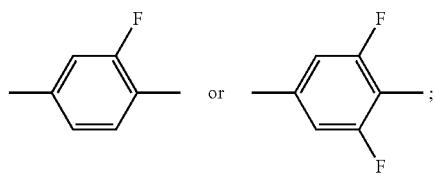

$R^2$ denotes H, unfluorinated alkyl or unfluorinated alkoxy having 1 to 17, preferably 3 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

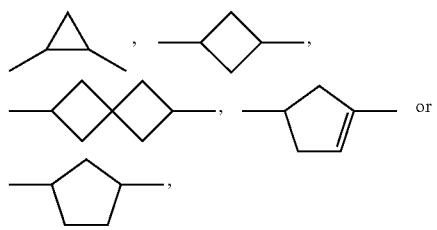

preferably unfluorinated alkyl or unfluorinated alkenyl, $Z^{21}$ denotes trans-CH=CH—, trans-CF=CF— or —C≡C—, preferably —C≡C— or trans-CH=CH—, and

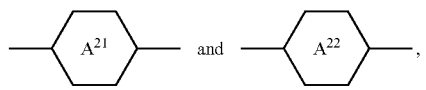

independently of one another, denote

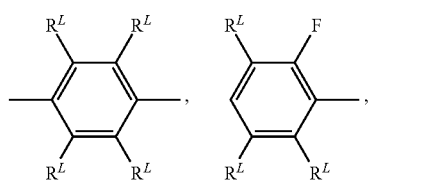

-continued

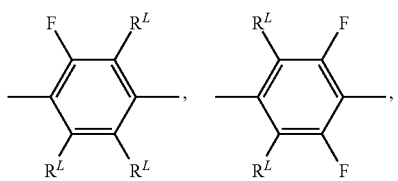

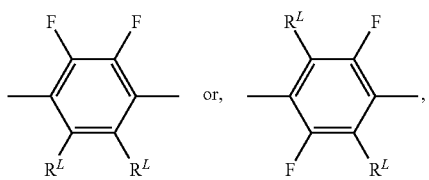

in which $R^L$, on each occurrence, identically or differently, denotes H or alkyl having 1 to 6 C atoms, preferably H, methyl or ethyl, particularly preferably H, and wherein

alternatively denotes

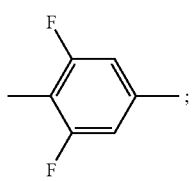

preferably

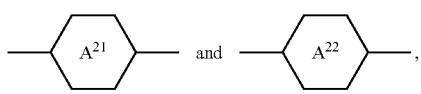

independently of one another, denote

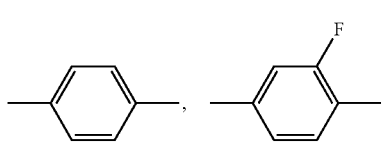

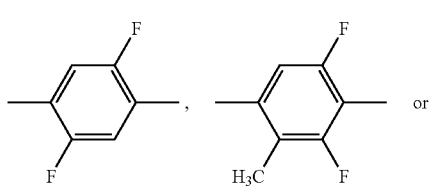

-continued

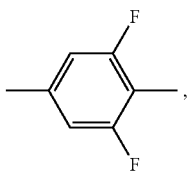

preferably denotes

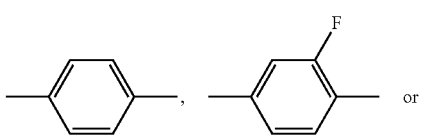

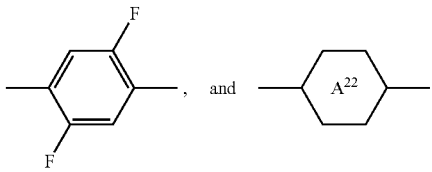

preferably denotes

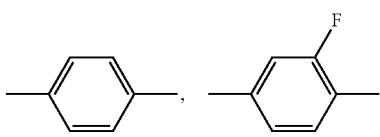

more preferably

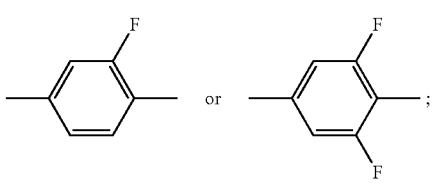

$R^3$ denotes H, unfluorinated alkyl or unfluorinated alkoxy having 1 to 17, preferably 3 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

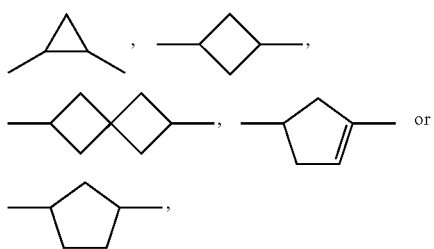

preferably unfluorinated alkyl or unfluorinated alkenyl, one of $Z^{31}$ and $Z^{32}$, preferably $Z^{32}$; denotes trans-CH=CH—, trans-CF=CF— or —C≡C— and the other one, independently thereof, denotes —C≡C—, trans-CH=CH—, trans-CF=CF— or a single bond, preferably one of them, preferably $Z^{32}$; denotes —C≡C— or trans-CH=CH— and the other denotes a single bond, and

to

independently of one another, denote

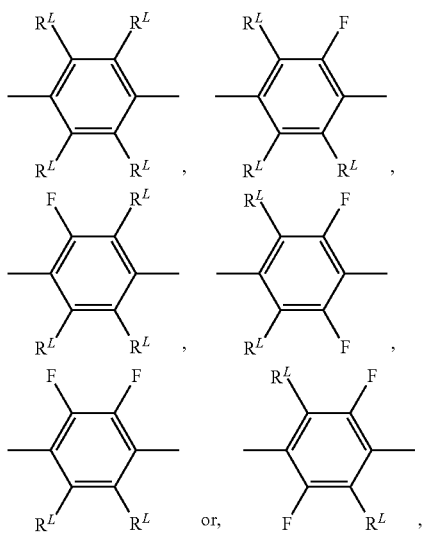

in which $R^L$, on each occurrence, identically or differently, denotes H or alkyl having 1 to 6 C atoms, preferably H, methyl or ethyl, particularly preferably H, and wherein

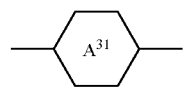

alternatively denotes

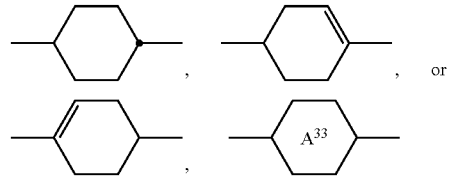

alternatively denotes

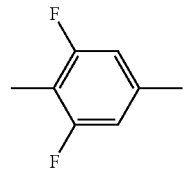

preferably

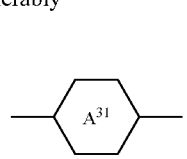

to

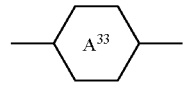

independently of one another, denote

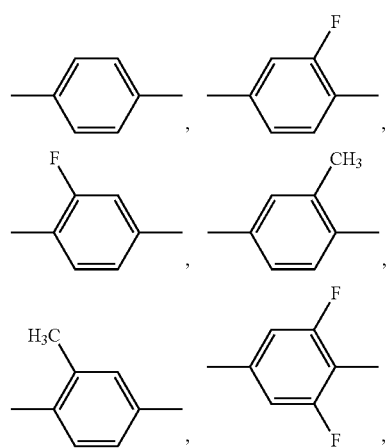

-continued

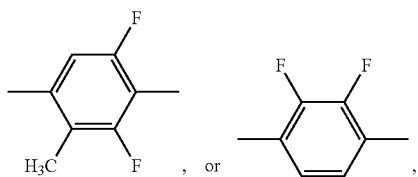, or more preferably

denotes

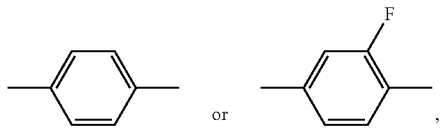

denotes

in particular

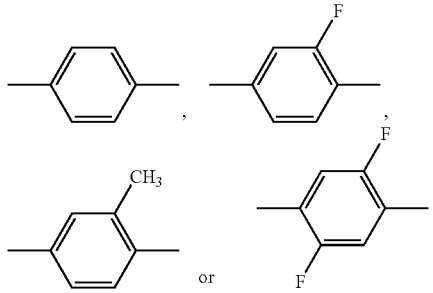

denotes

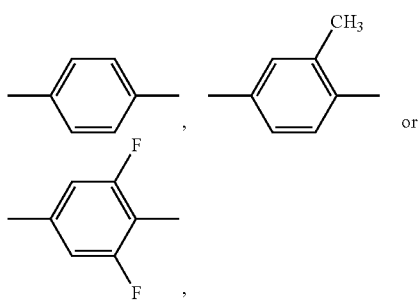,

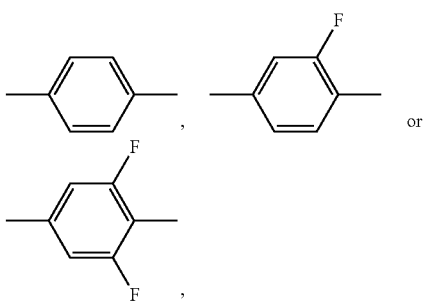

in particular

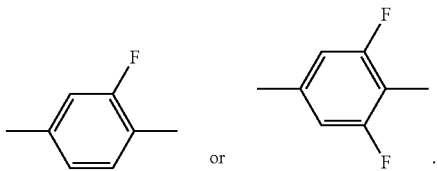.

In the compounds of the formulae I, II and III, $R^L$ preferably denotes H.

In another preferred embodiment, in the compounds of formulae I, II and III, one or two groups $R^L$, preferably one group $R^L$ is different from H.

In a preferred embodiment of the present invention, the compounds of formula I are selected from the group of compounds of the formulae I-1 to I-5:

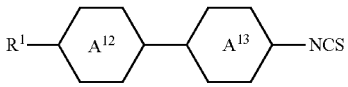  I-1

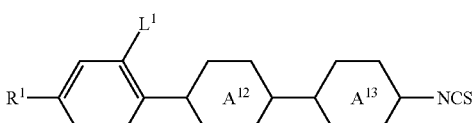  I-2

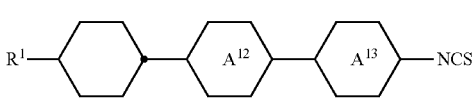  I-3

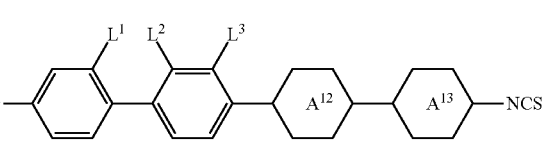  I-4

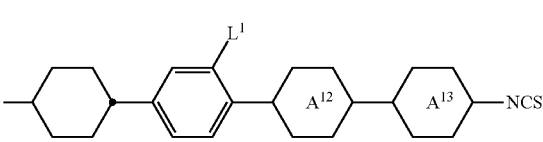  I-5 in which $L^1$, $L^2$ and $L^3$ on each occurrence, identically or differently, denote H or F, and the other groups have the respective meanings indicated above for formula I and preferably R¹ denotes unfluorinated alkyl having 1 to 7 C atoms or unfluorinated alkenyl having 2 to 7 C atoms.

The media preferably comprise one or more compounds of formula I-1, which are preferably selected from the group of the compounds of the formulae I-1a to I-1d, preferably of formula I-1b:

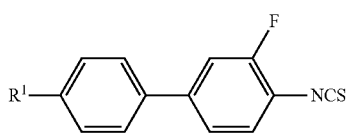
I-1a

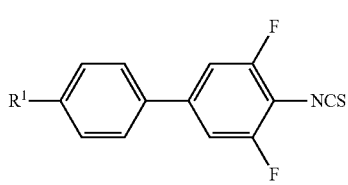
I-1b

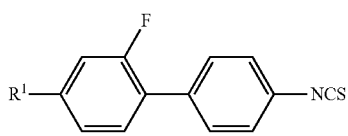
I-1c

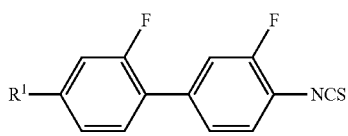
I-1d in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-2, which are preferably selected from the group of the compounds of the formulae I-2a to I-2e, preferably of formula I-2c:

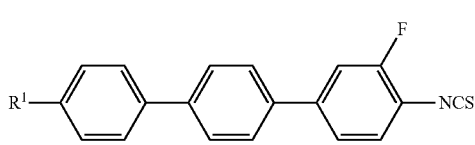
I-2a

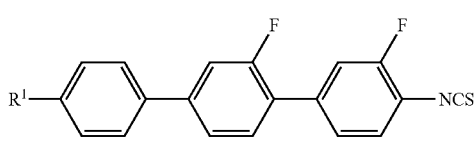
I-2b

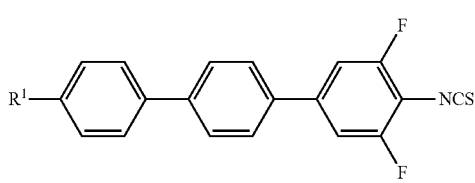
I-2c

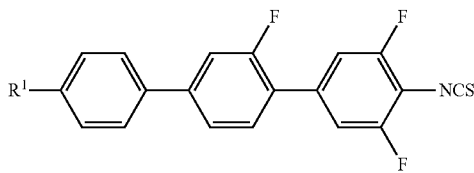
I-2d

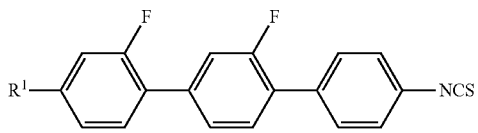
I-2e in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-3, which are preferably selected from the group of the compounds of the formulae I-3a to I-3d, particularly preferably of formula I-3b:

I-3a

I-3b

I-3c

I-3d in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-4, which are preferably selected from the group of the compounds of the formulae I-4a to I-4e, particularly preferably of formula I-4b:

I-4a

I-4b
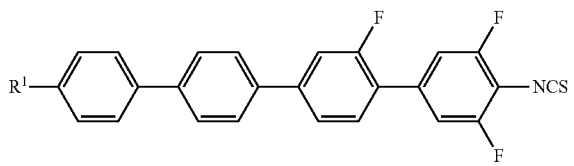

I-4c
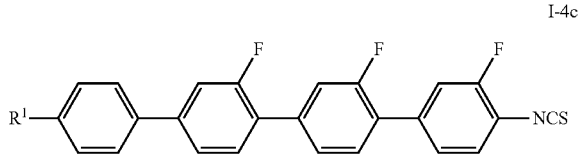

I-4d
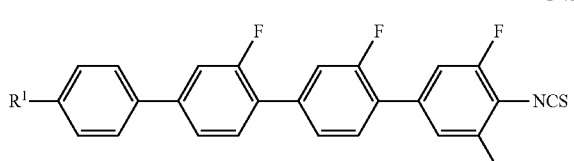

I-4e
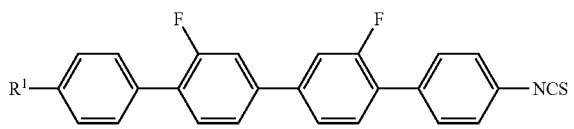

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula I-5, which are preferably selected from the group of the compounds of the formulae I-5a to I-5d, particularly preferably of formula I-5b:

I-5a
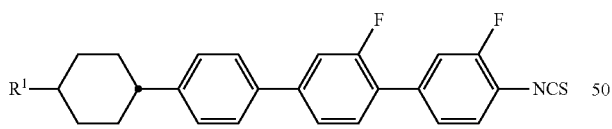

I-5b
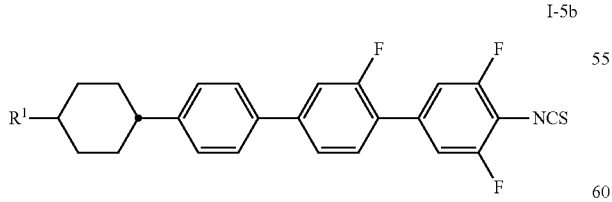

I-5c
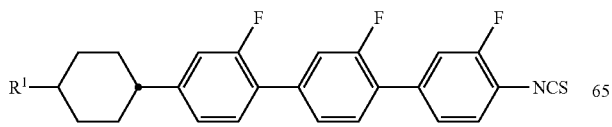

I-5d
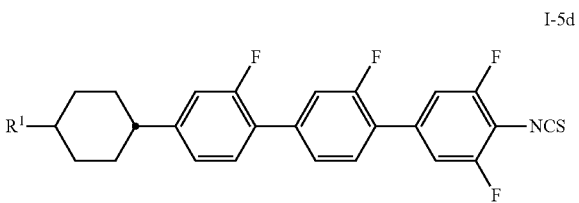

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula II, which are preferably selected from the group of the compounds of the formulae II-1 to II-3, preferably selected from the group of the compounds of the formulae II-1 and II-2:

II-1
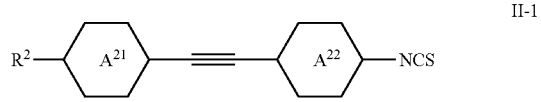

II-2
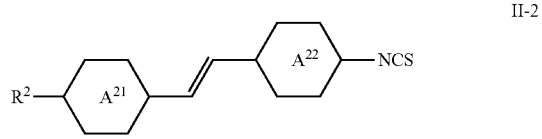

II-3
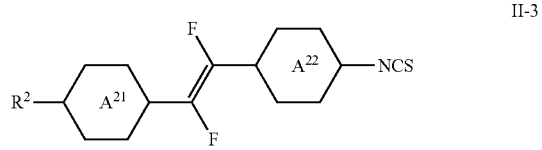

in which the occurring groups have the meanings given under formula II above and preferably $R^2$ denotes H, unfluorinated alkyl or alkoxy having 1 to 7 C atoms or unfluorinated alkenyl having 2 to 7 C atoms, and one of

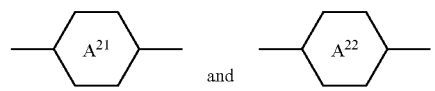

denotes

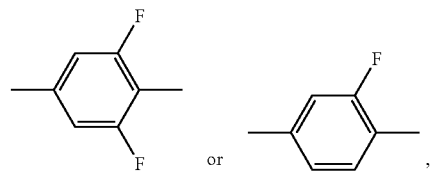

and the other, independently denotes

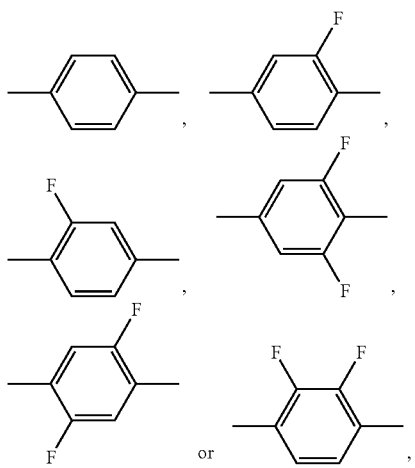

preferably

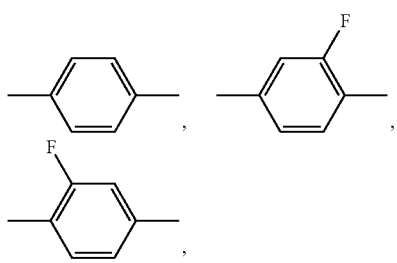

most preferably

and preferably
R² denotes $C_nH_{2n+1}$ or $CH_2=CH-(CH_2)_z$, and
n denotes an integer in the range from 1 to 15, preferably in the range from 1 to 7 and particularly preferably 1 to 5, and
z denotes 0, 1, 2, 3 or 4, preferably 0 or 2.

The compounds of formula II-1 are preferably selected from the group of the compounds of the formulae II-1a to II-1e:

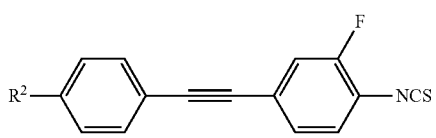
II-1a

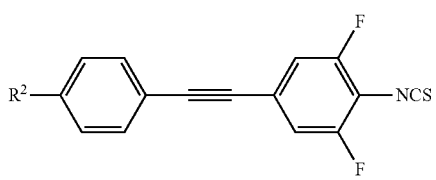
II-1b

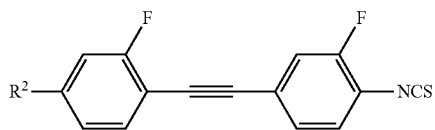
II-1c

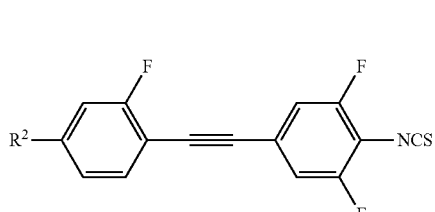
II-1d

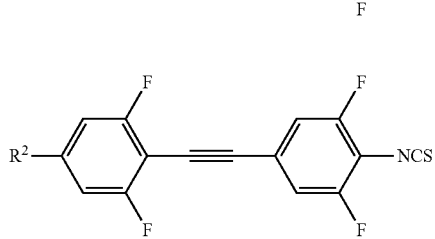
II-1e in which

R² has the meaning indicated above and preferably denotes $C_nH_{2n+1}$ or $CH_2=CH-(CH_2)_z$, and n independently of one another, denote an integer in the range from 1 to 15, preferably in the range from 1 to 7 and particularly preferably 1 to 5, and z denotes 0, 1, 2, 3 or 4, preferably 0 or 2.

The compounds of formula II-2 are preferably selected from the group of the compounds of the formulae II-2a and II-2b:

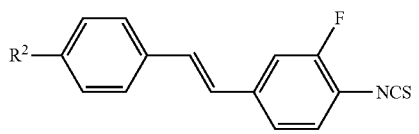
II-2a

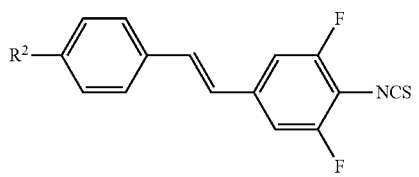
II-2b in which

R² has the meaning indicated above and preferably denotes $C_nH_{2n+1}$ or $CH_2=CH-(CH_2)_z$, n denotes an integer in the range from 1 to 15, preferably in the range from 1 to 7 and particularly preferably 1 to 5, and z denotes 0, 1, 2, 3 or 4, preferably 0 or 2.

The compounds of formula II-3 are preferably selected from the group of the compounds of the of formulae II-3a to II-3d:

II-3a
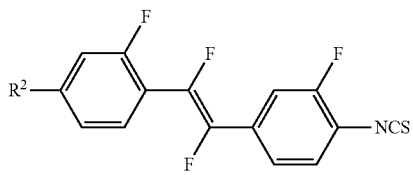

II-3b
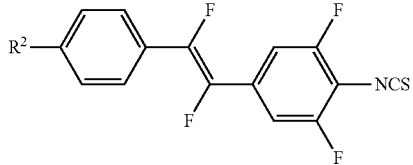

II-3c
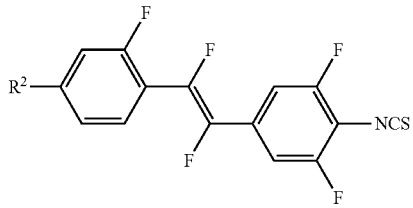

II-3d
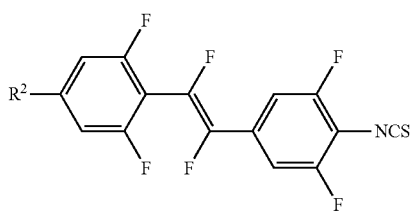

in which
R² has the meaning indicated above and preferably denotes $C_nH_{2n+1}$ or $CH_2$=CH—$(CH_2)_z$,
n denotes an integer in the range from 1 to 15, preferably in the range from 1 to 7 and particularly preferably 1 to 5, and
z denotes 0, 1, 2, 3 or 4, preferably 0 or 2.

The compounds of formula III are preferably selected from the group of the compounds of the formulae III-1 to III-6, more preferably of the formulae selected from the group of the compounds of the formulae III-1, III-2, III-3 and III-4, and particularly preferably of formula III-1:

III-1
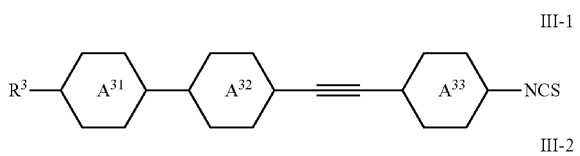

III-2
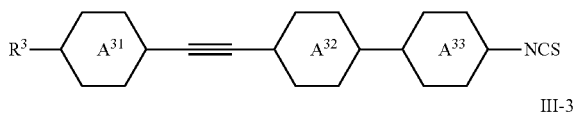

III-3
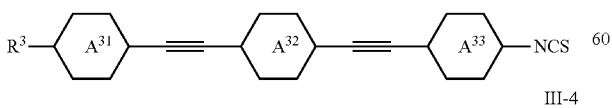

III-4
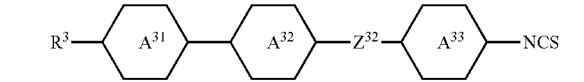

III-5
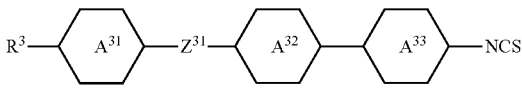

III-6
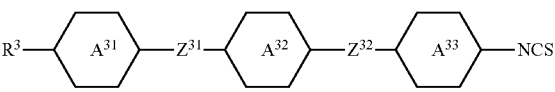

in which
$Z^{31}$ and $Z^{32}$ independently of one another denote trans-CH=CH— or trans-CF=CF—, preferably trans-CH=CH—, and in formula III-6 alternatively one of $Z^{31}$ and $Z^{32}$ may denote —C≡C— and the other groups have the meaning given above under formula III, and preferably R³ unfluorinated alkyl or alkoxy having 1 to 7 C atoms or unfluorinated alkenyl having 2 to 7 C atoms, and one of

to

preferably

denotes

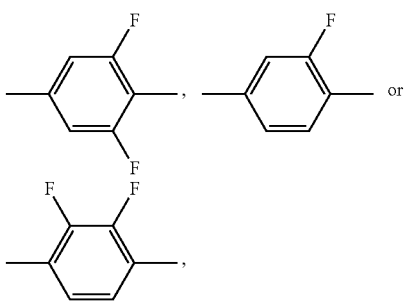

preferably

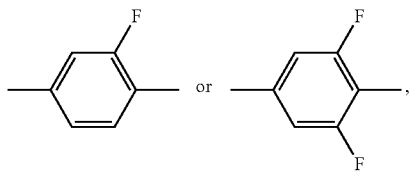

and the others, independently of one another, denote

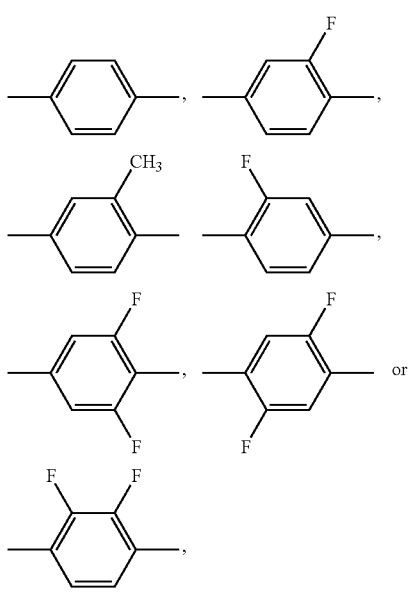

preferably

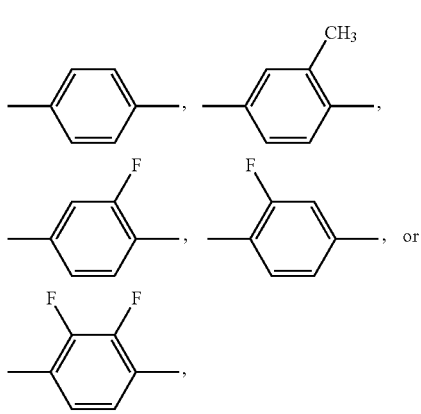

more preferably

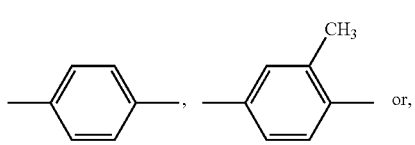

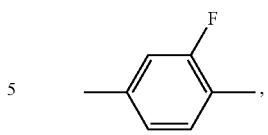

where

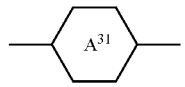

alternatively denotes

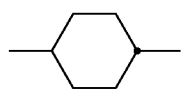

and preferably $R^3$ denotes $C_nH_{2n+1}$ or $CH_2=CH-(CH_2)_z$, n denotes an integer in the range from 1 to 15, preferably in the range from 1 to 7 and particularly preferably 1 to 5, and z denotes 0, 1, 2, 3 or 4, preferably 0 or 2.

The compounds of formula III-1 are preferably selected from the group of the compounds of the formulae III-1a to III-1l, more preferably selected from the group of the compounds of the formulae III-1b, III-1f, III-1g and III-1i

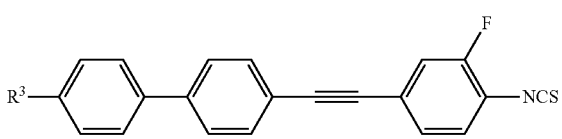

III-1a

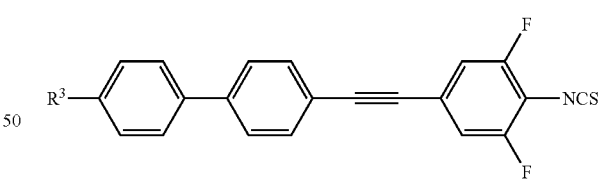

III-1b

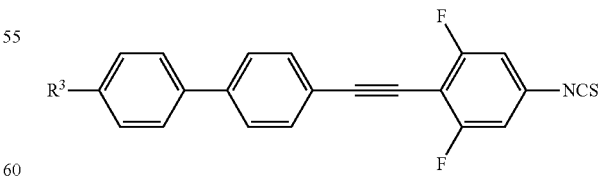

III-1c

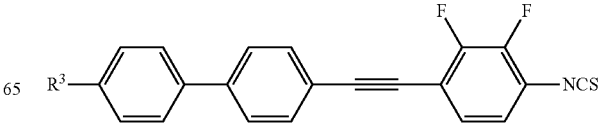

III-1d

-continued

III-1e
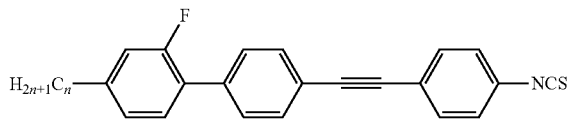

III-1f
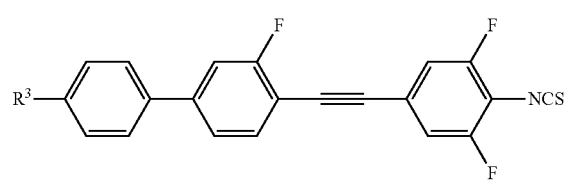

III-1g
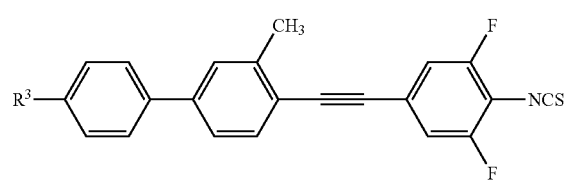

III-1h
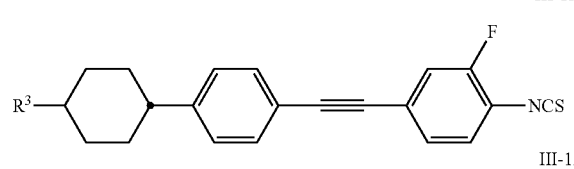

III-1i
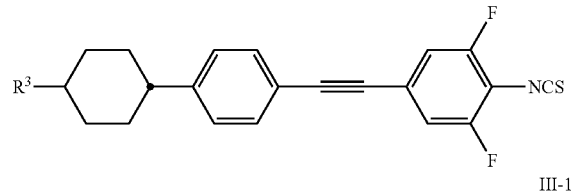

III-1j
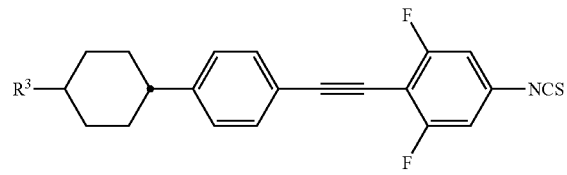

III-1k
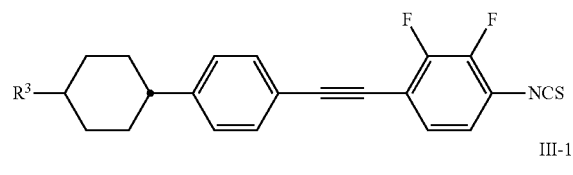

III-1l
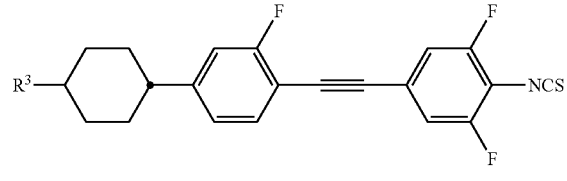

in which
R³ has the meaning indicated above and preferably denotes $C_nH_{2n+1}$ or $CH_2=CH-(CH_2)_z$,
n denotes an integer in the range from 1 to 15, preferably in the range from 1 to 7 and particularly preferably 1 to 5, and
z denotes 0, 1, 2, 3 or 4, preferably 0 or 2.

The compounds of formula III-2 are preferably compounds of formula III-2a to III-2l, very preferably III-2b and/or III-2j:

III-2a

III-2b
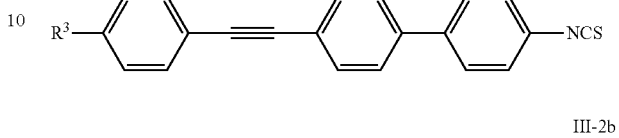

III-2c
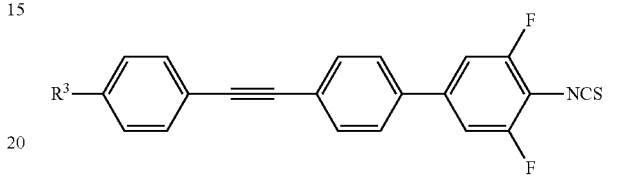

III-2d
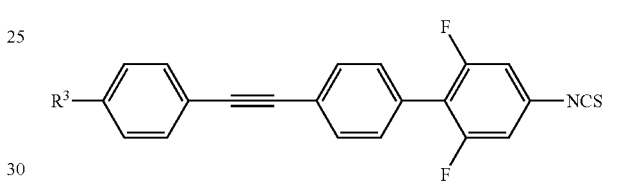

III-2e
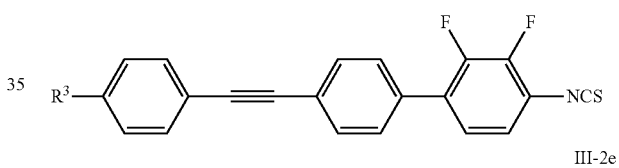

III-2f
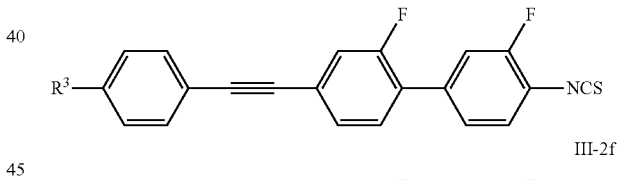

III-2g
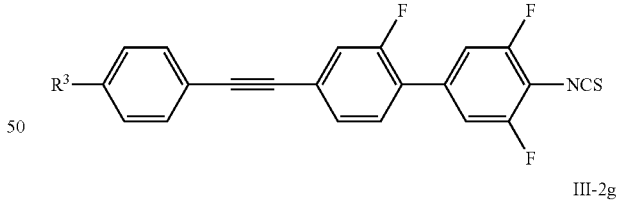

III-2h
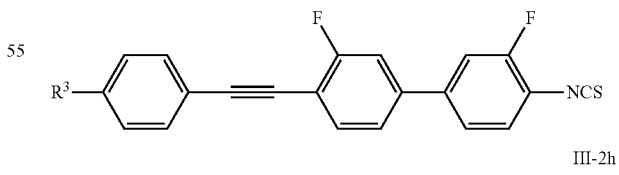

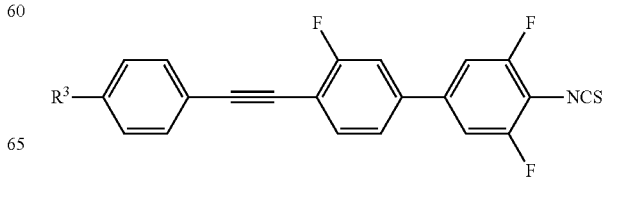

III-2i
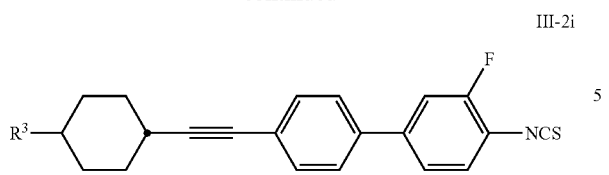

III-2j
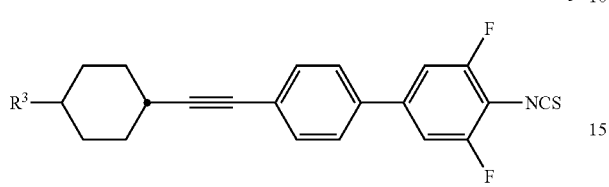

III-2k
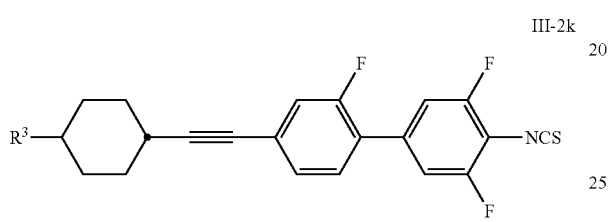

III-2l
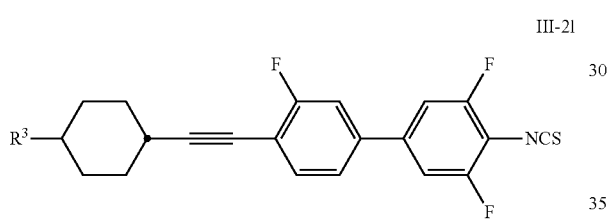

$R^3$ has the meaning indicated above and preferably denotes $C_nH_{2n+1}$ or $CH_2=CH-(CH_2)_z$, n denotes an integer in the range from 1 to 15, preferably in the range from 1 to 7 and particularly preferably 1 to 5, and z denotes 0, 1, 2, 3 or 4, preferably 0 or 2.

The compounds of formula III-5 are preferably selected from the compounds of formula III-5a:

III-5a
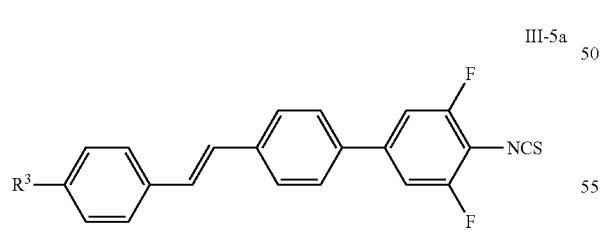

$R^3$ has the meaning indicated above for formula III-5 and preferably denotes $C_nH_{2n+1}$, in which n denotes an integer in the range from 1 to 7, preferably in the range from 1 to 5.

In a preferred embodiment, the media according to the invention comprise one or more compounds selected from the group of compounds of the formulae IIA-1-1 to IIA-1-12, very preferably IIA-1-1 or IIA-1-2:

IIA-1-1
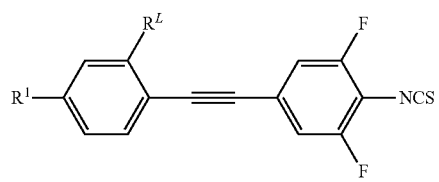

IIA-1-2
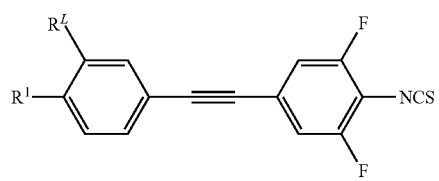

IIA-1-3
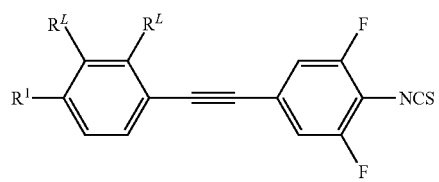

IIA-1-4
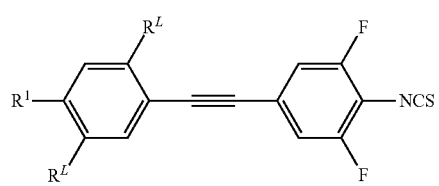

IIA-1-5
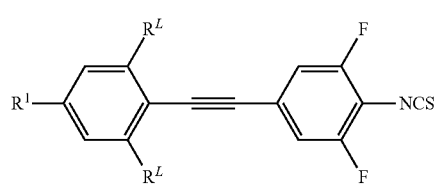

IIA-1-6
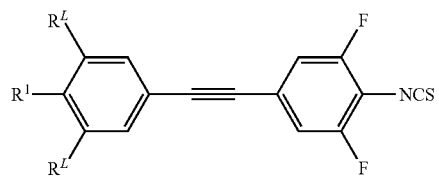

IIA-1-7
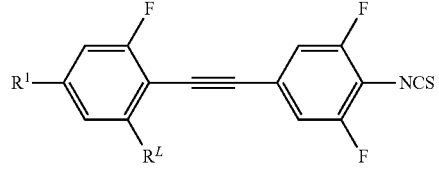

IIA-1-8
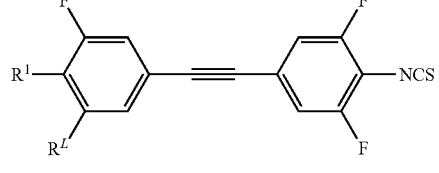

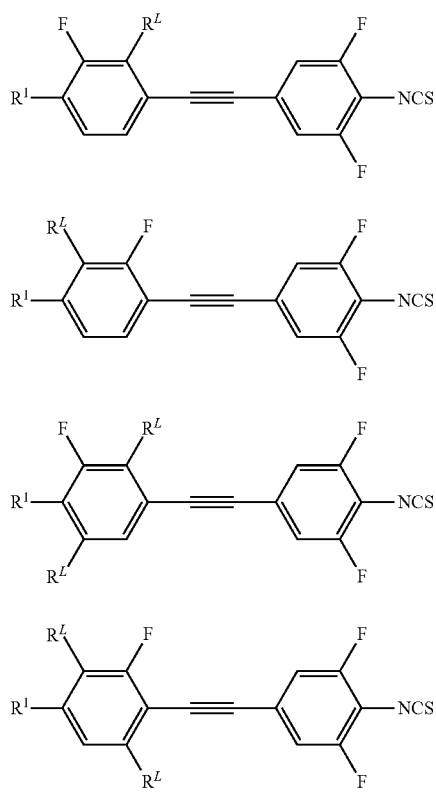

in which

R¹ denotes alkyl or alkenyl having up to 7 C atoms, preferably ethyl, n-propyl, n-butyl or n-pentyl, n-hexyl, R$^L$ on each occurrence, the same or differently, denotes alkyl or alkenyl having 1 to 5 C atoms, or cycloalkyl or cycloalkenyl each having 3 to 6 C atoms, preferably methyl, ethyl, n-propyl, n-butyl, isopropyl, cyclopropyl, cyclobutyl, cyclopentyl or cyclopent-1-enyl, very preferably ethyl, and from which the compounds of formula II-1 are excluded.

Additionally, the liquid-crystalline media according to the present invention in a certain embodiment, which may be the same or different from the previous preferred embodiments preferably comprise one or more compounds of formula IV,

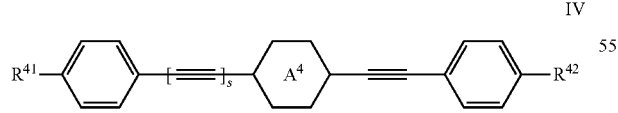

IV in which

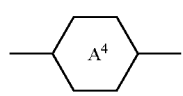

denotes

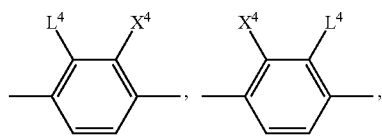

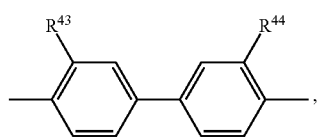

 or

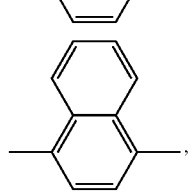

s is 0 or 1, preferably 1, and
preferably

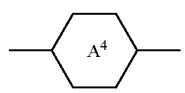

denotes

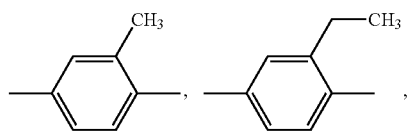

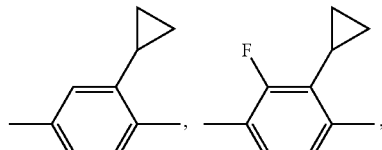

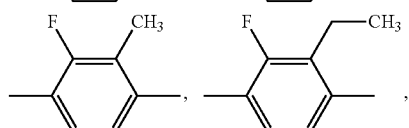

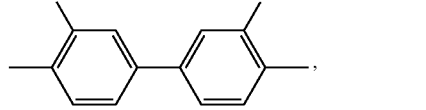

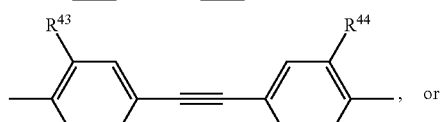 or

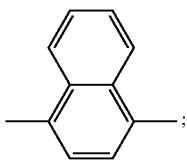

particularly preferably

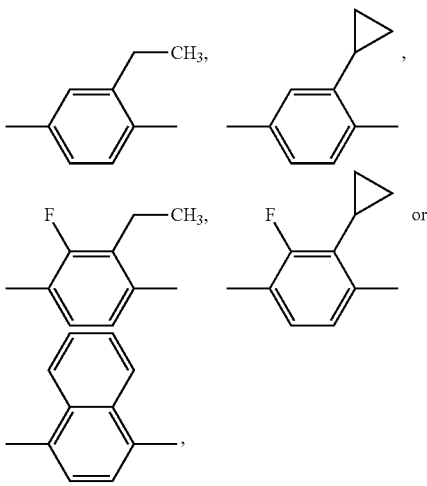

L$^4$ denotes H or alkyl having 1 to 6 C atoms, cycloalkyl having 3 to 6 C atoms or cycloalkenyl having 4 to 6 C atoms, preferably CH$_3$, C$_2$H$_5$, n-C$_3$H$_7$, i-C$_3$H$_7$, cyclopropyl, cyclobutyl, cyclohexyl, cyclopent-1-enyl or cyclohex-1-enyl, and particularly preferably CH$_3$, C$_2$H$_5$, cyclopropyl or cyclobutyl, X$^4$ denotes H, alkyl having 1 to 3 C atoms or halogen, preferably H, F or Cl, more preferably H or F and very particularly preferably F, R$^{41}$ to R$^{44}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of R$^{43}$ and R$^{44}$ or both also denote H, preferably R$^{41}$ and R$^{42}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably R$^{41}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably R$^{42}$ denotes unfluorinated alkyl or unfluorinated alkoxy, each having 1 to 7 C atoms, and preferably R$^{43}$ and R$^{44}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of R$^{43}$ and R$^{44}$ denotes n-alkyl, particularly preferably methyl, ethyl or n-propyl, and the other denotes H or n-alkyl, particularly preferably H, methyl, ethyl or n-propyl.

In a preferred embodiment of the present invention, the liquid-crystal medium additionally comprises one or more compounds selected from the group of compounds of the formulae V, VI, VII, VIII and IX:

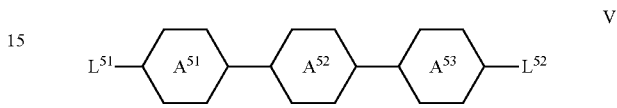

V

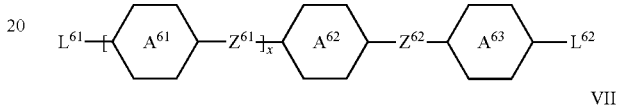

VI

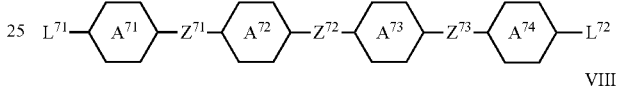

VII

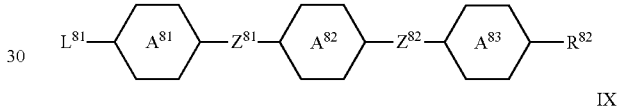

VIII

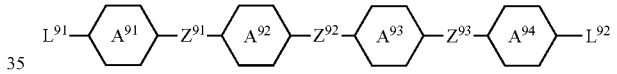

IX in which

L$^{51}$ denotes R$^{51}$ or X$^{51}$,

L$^{52}$ denotes R$^{52}$ or X$^{52}$,

R$^{51}$ and R$^{52}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, X$^{51}$ and X$^{52}$, independently of one another, denote H, F, Cl, —CN, SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl, and

to

, independently of one another, denote

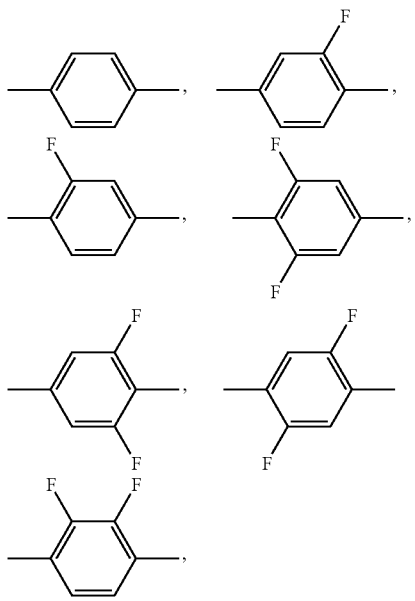

preferably

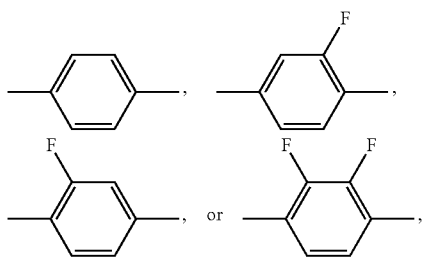

L$^{61}$ denotes R$^{61}$ and, in the case where Z$^{61}$ and/or Z$^{62}$ denote trans-CH=CH— or trans-CF=CF—, alternatively also denotes X$^{61}$, L$^{62}$ denotes R$^{62}$ and, in the case where Z$^{61}$ and/or Z$^{62}$ denote trans-CH=CH— or trans-CF=CF—, alternatively also denotes X$^{62}$, R$^{61}$ and R$^{62}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, X$^{61}$ and X$^{62}$, independently of one another, denote F or Cl, —CN, SF$_5$, fluorinated alkyl or alkoxy having 1 to 7 C atoms or fluorinated alkenyl, alkenyloxy or alkoxyalkyl having 2 to 7 C atoms, one of Z$^{61}$ and Z$^{62}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

to independently of one another, denote

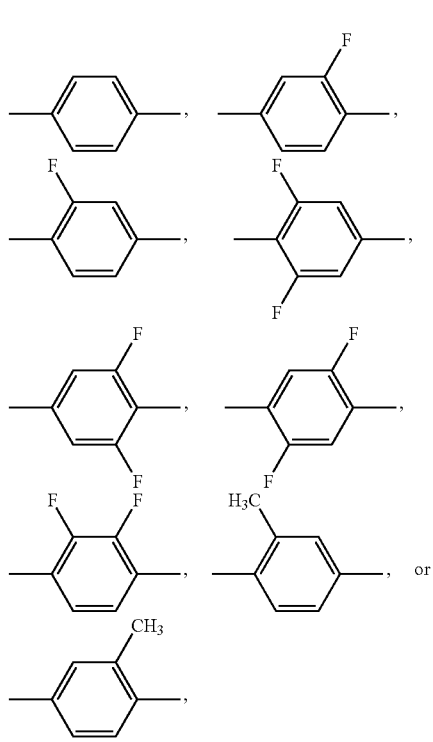

preferably

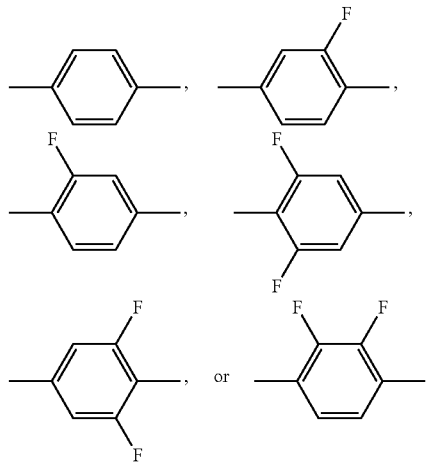

and x denotes 0 or 1;

$L^{71}$ denotes $R^{71}$ or $X^{71}$, $L^{72}$ denotes $R^{72}$ or $X^{72}$, $R^{71}$ and $R^{72}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{71}$ and $X^{72}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{71}$ to $Z^{73}$, independently of one another, denote trans-CH=CH—, trans-CF=CF—, —C≡C— or a single bond, preferably one or more of them denote a single bond, particularly preferably all denote a single bond and

to

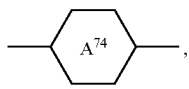

independently of one another, denote

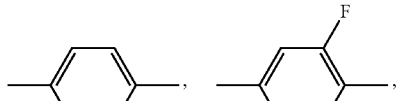

or

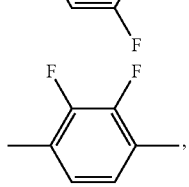

preferably

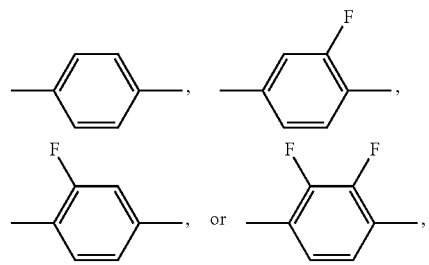

$R^{81}$ and $R^{82}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl, one of $Z^{81}$ and $Z^{82}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

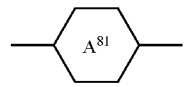

denotes

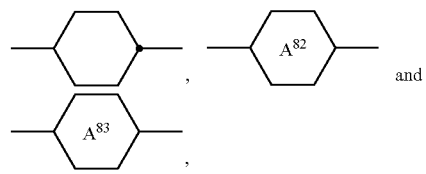

independently of one another, denote

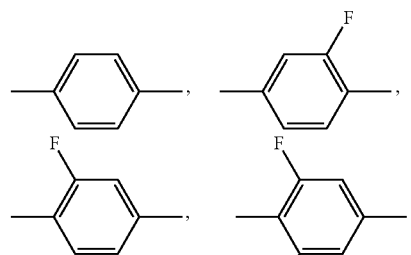

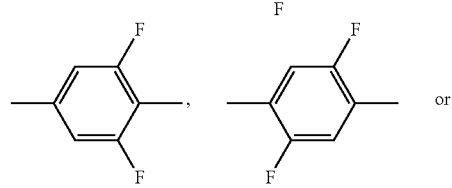

or

-continued

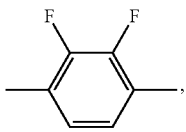

$L^{91}$ denotes $R^{91}$ or $X^{91}$,
$L^{92}$ denotes $R^{92}$ or $X^{92}$,
$R^{91}$ and $R^{92}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl,
$X^{91}$ and $X^{92}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and
$Z^{91}$ to $Z^{93}$, independently of one another, denote trans-CH=CH—, trans-CF=CF—, —C≡C— or a single bond, preferably one or more of them denotes a single bond, and particularly preferably all denote a single bond,

denotes

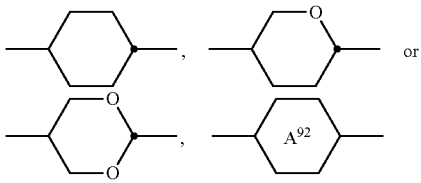

to

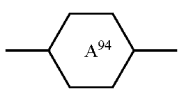

independently of one another, denote

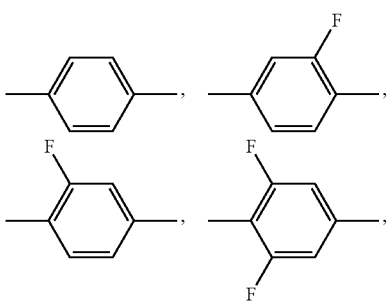

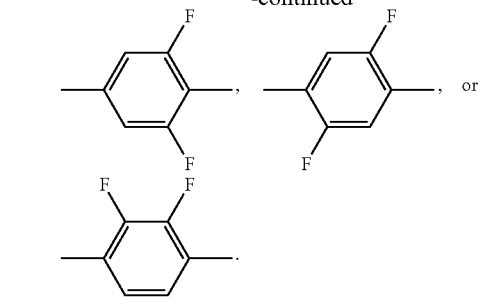

In a preferred embodiment of the present invention, the liquid-crystal medium comprises one or more compounds of the formula V, preferably selected from the group of the compounds of the formulae V-1 to V-3, preferably of the formulae V-1 and/or V-2 and/or V-3, preferably of the formulae V-1 and V-2:

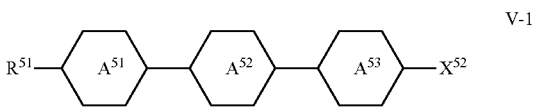

V-1

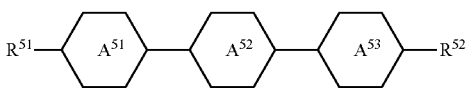

V-2

V-3 in which the occurring groups have the respective meanings indicated above for formula V and preferably $R^{51}$ denotes unfluorinated alkyl having 1 to 7 C atoms or unfluorinated alkenyl having 2 to 7 C atoms, $R^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —OCF$_3$, —CF$_3$, —CN or —SF$_5$, preferably F, Cl, —OCF$_3$ or —CN.

The compounds of the formula V-1 are preferably selected from the group of the compounds of the formulae V-1a to V-1d, preferably V-1c and V-1d:

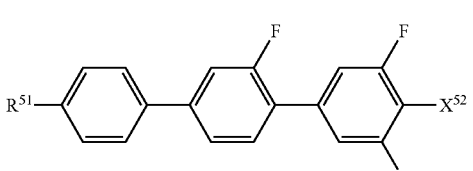

V-1a

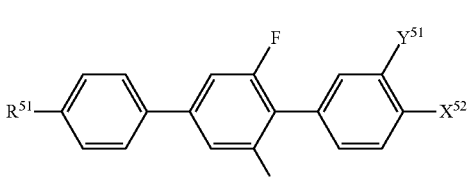

V-1b

-continued

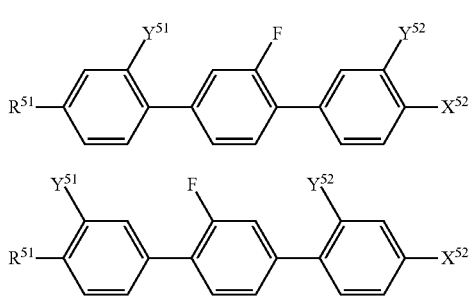

V-1c

V-1d in which the parameters have the respective meanings indicated above for formula V-1 and in which
$Y^{51}$ and $Y^{52}$, in each case independently of one another, denote H or F, and preferably
$R^{51}$ denotes alkyl or alkenyl, and
$X^{51}$ denotes F, Cl or —OCF$_3$.

The compounds of the formula V-2 are preferably selected from the group of the compounds of the formulae V-2a to V-2e and/or from the group of the compounds of the formulae V-2f and V-2g:

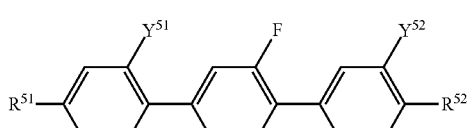

V-2a

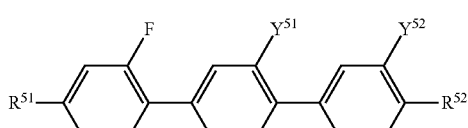

V-2b

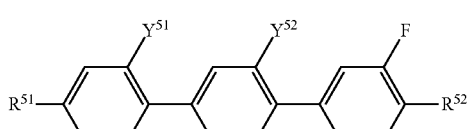

V-2c

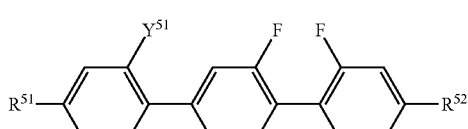

V-2d

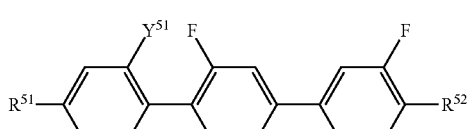

V-2e

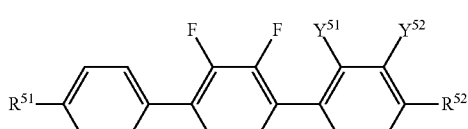

V-2f

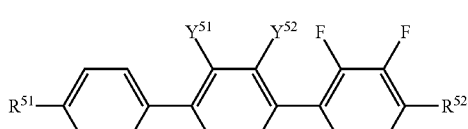

V-2g where in each case the compounds of the formula V-2a are excluded from the compounds of the formulae V-2b and V-2c, the compounds of the formula V-2b are excluded from the compounds of the formula V-2c and the compounds of the formula V-2f are excluded from the compounds of the formula V-2g, and in which the parameters have the respective meanings indicated above for formula V-1 and in which
$Y^{51}$ and $Y^{52}$, in each case independently of one another, denote H or F, and preferably
$Y^{51}$ and $Y^{52}$ denotes H and the other denotes H or F, preferably likewise denotes H.

The compounds of the formula V-3 are preferably compounds of the formula V-3a:

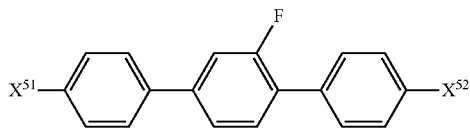

V-3a in which the parameters have the respective meanings indicated above for formula V-1 and in which preferably
$X^{51}$ denotes F, Cl, preferably F,
$X^{52}$ denotes F, Cl or —OCF$_3$, preferably —OCF$_3$.

The compounds of the formula V-1a are preferably selected from the group of the compounds of the formulae V-1a-1 and V-1a-2:

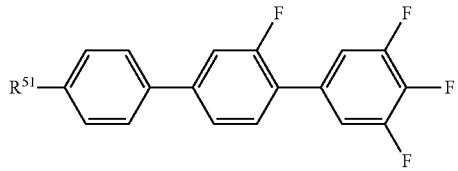

V-1a-1

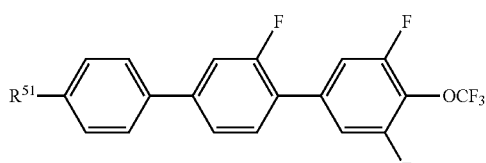

V-1a-2 in which
$R^{51}$ has the meaning indicated above and preferably denotes $C_nH_{2n+1}$, in which
n denotes an integer in the range from 1 to 7, preferably in the range from 1 to 5 and particularly preferably 3 or 4.

The compounds of the formula V-1b are preferably compounds of the formula V-1 b-1:

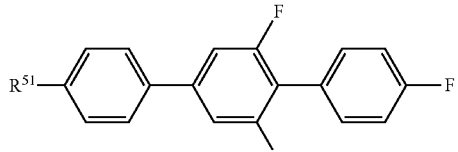

V-1b-1 in which

R$^{51}$ has the meaning indicated above and preferably denotes C$_n$H$_{2n+1}$, in which n denotes an integer in the range from 1 to 15, preferably in the range from 1 to 7 and particularly preferably 1 to 5.

The compounds of the formula V-1c are preferably selected from the group of the compounds of the formulae V-1c-1 to V-1c-4, particularly preferably selected from the group of the compounds of the formulae V-1c-1 and V-1c-2:

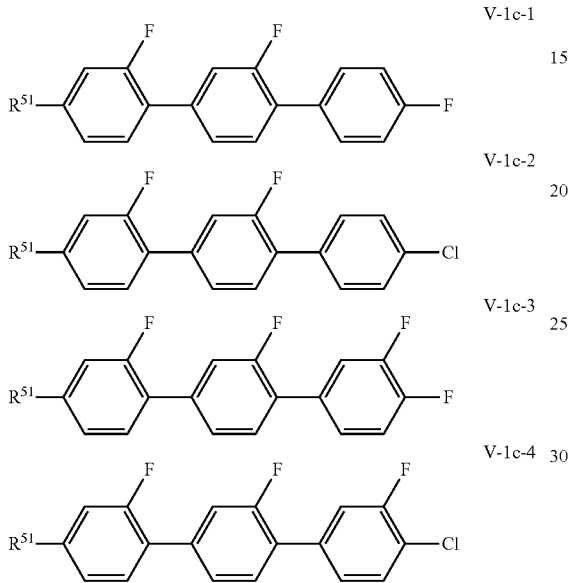

in which

R$^{51}$ has the meaning indicated above and preferably denotes C$_n$H$_{2n+1}$, in which n denotes an integer in the range from 1 to 15, preferably in the range from 1 to 7 and particularly preferably 1 to 5.

The compounds of the formula V-1d are preferably selected from the group of the compounds of the formulae V-1d-1 and V-1d-2, particularly preferably the compound of the formula V-1d-2:

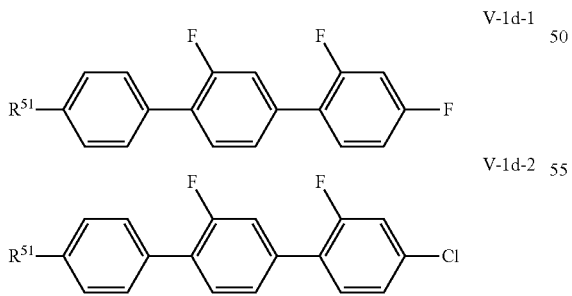

in which

R$^{51}$ has the meaning indicated above and preferably denotes C$_n$H$_{2n+1}$, in which n denotes an integer in the range from 1 to 15, preferably in the range from 1 to 7 and particularly preferably 1 to 5.

The compounds of the formula V-2a are preferably selected from the group of the compounds of the formulae V-2a-1 and V-2a-2, particularly preferably the compounds of the formula V-2a-1:

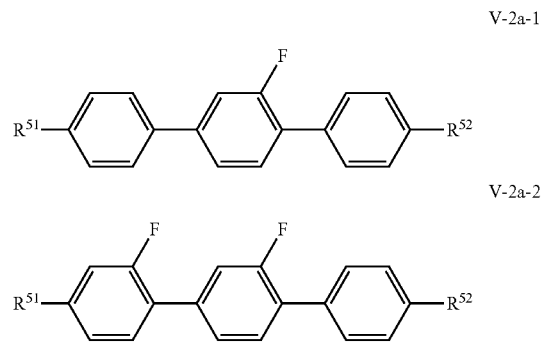

in which

R$^{51}$ has the meaning indicated above and preferably denotes C$_n$H$_{2n+1}$ or CH$_2$=CH—(CH$_2$)$^z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

Preferred combinations of (R$^{51}$ and R$^{52}$), in particular in the case of formula V-2a-1, are (C$_n$H$_{2n+1}$ and C$_m$H$_{2m+1}$), (C$_n$H$_{2n+1}$ and O—C$_m$H$_{2m+1}$), (CH$_2$=CH—(CH$_2$)$_z$ and C$_m$H$_{2m+1}$), (CH$_2$=CH—(CH$_2$)$_z$ and O—C$_m$H$_{2m+1}$) and (C$_n$H$_{2n+1}$ and (CH$_2$)$_z$—CH=CH$_2$).

Preferred compounds of the formula V-2b are the compounds of the formula V-2b-1:

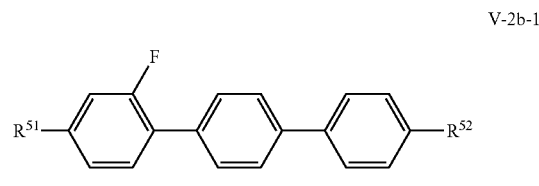

in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2c are the compounds of the formula V-2c-1:

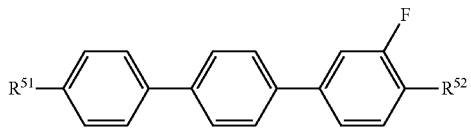

V-2c-1 in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2d are the compounds of the formula V-2d-1:

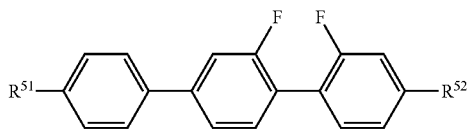

V-2d-1 in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2e are the compounds of the formula V-2e-1:

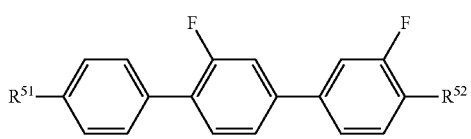

V-2e-1 in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and O—C$_m$H$_{2m+1}$).

Preferred compounds of the formula V-2f are the compounds of the formula V-2f-1:

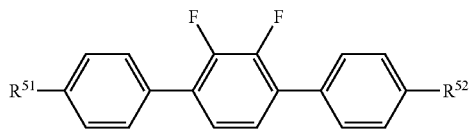

V-2f-1 in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

Preferred compounds of the formula V-2g are the compounds of the formula V-2g-1:

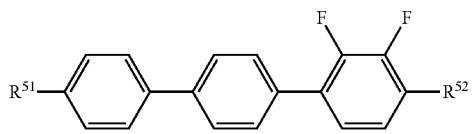

V-2g-1 in which
R$^{51}$ has the meaning indicated above and preferably denotes C$_n$H$_{2n+1}$ or CH$_2$=CH—(CH$_2$)$_z$, and
R$^{52}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and O—C$_m$H$_{2m+1}$).

The compounds of the formula VI are preferably selected from the group of the compounds of the formulae VI-1 to VI-5:

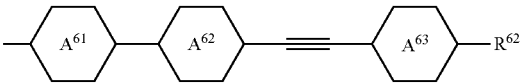

VI-1

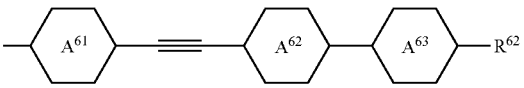

VI-2

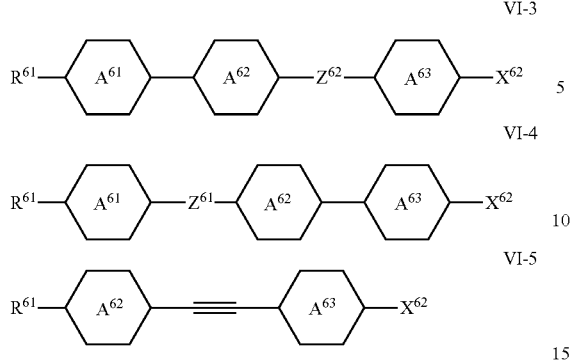

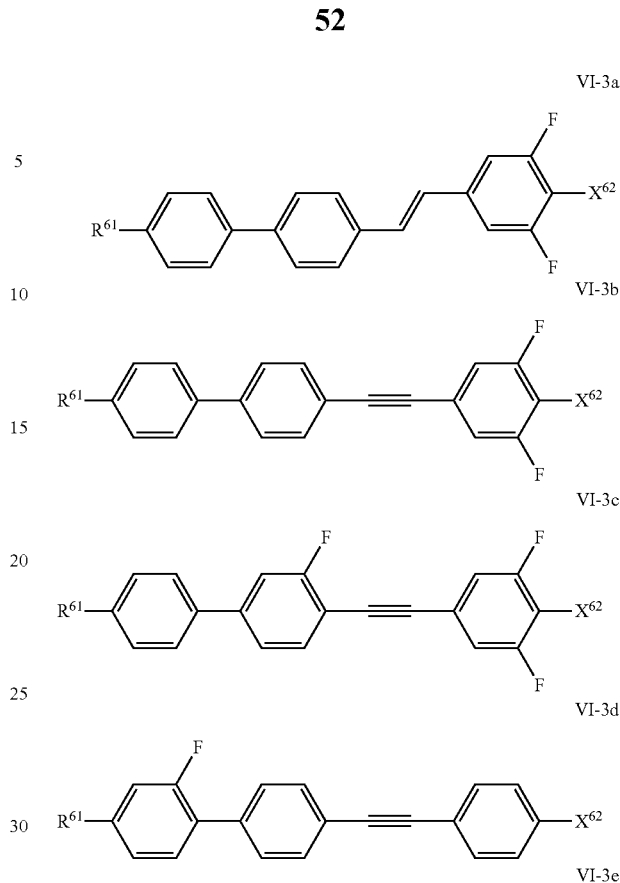

in which
Z$^{61}$ and Z$^{62}$ denote —C≡C—, trans-CH=CH— or trans-CF=CF—, preferably —C≡C— or trans-CH=CH—, and the other occurring groups and parameters have the meaning given above under formula VI,
and preferably
R$^{61}$ and R$^{62}$, independently of one another, denote H, unfluorinated alkyl or alkoxy having 1 to 7 C atoms or unfluorinated alkenyl having 2 to 7 C atoms,
X$^{62}$ denotes F, Cl, —OCF$_3$ or —CN, The compounds of the formula VI-1 are preferably selected from the group of the compounds of the formulae VI-1a and VI-1b, more preferably selected from compounds of the formula VI-1a:

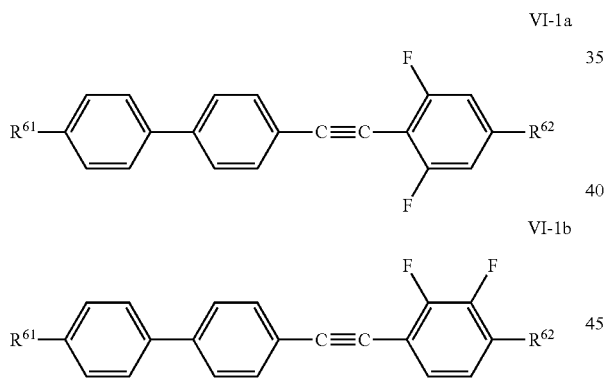

in which
R$^{61}$ has the meaning indicated above and preferably denotes C$_n$H$_{2n+1}$ or CH$_2$=CH—(CH$_2$)$_z$, and
R$^{62}$ has the meaning indicated above and preferably denotes C$_m$H$_{2m+1}$ or O—C$_m$H$_{2m+1}$ or (CH$_2$)$_z$—CH=CH$_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R$^{61}$ and R$^{62}$) here are, in particular, (C$_n$H$_{2n+1}$ and C$_m$H$_{2m+1}$) and (C$_n$H$_{2n+1}$ and O—C$_m$H$_{2m+1}$), in the case of formula VI-1a particularly preferably (C$_n$H$_{2n+1}$ and C$_m$H$_{2m+1}$) and in the case of formula VI-1b particularly preferably (C$_n$H$_{2n+1}$ and O—C$_m$H$_{2m+1}$).

The compounds of the formula VI-3 are preferably selected from the compounds of the formula VI-3a to VI-3e:

in which the parameters have the meaning given above under formula VI-3 and preferably
R$^{61}$ has the meaning indicated above and preferably denotes C$_n$H$_{2n+1}$, in which
n denotes an integer in the range from 1 to 7, preferably in the range from 1 to 5, and
X$^{62}$ denotes —F, —Cl, —OCF$_3$, or —CN.

The compounds of the formula VI-4 are preferably selected from compounds of the formulae VI-4a to VI-4e:

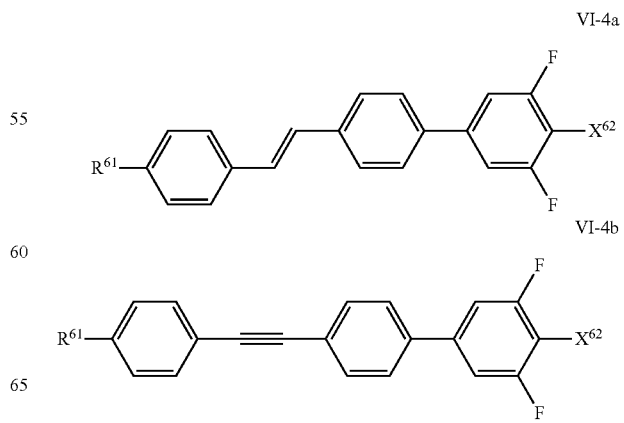

-continued

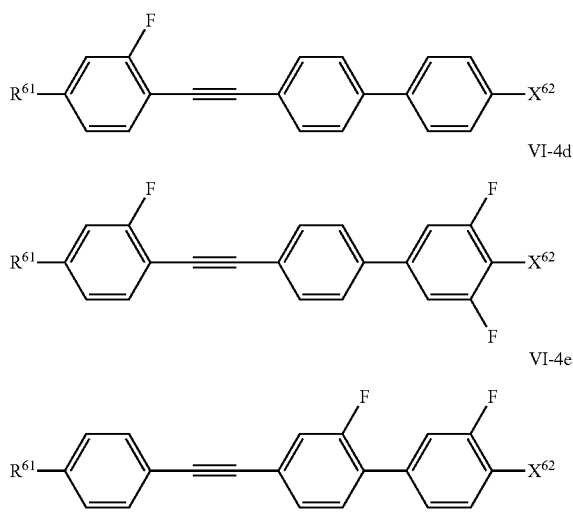

VI-4c

VI-4d

VI-4e in which the parameters have the meaning given above under formula VI-4 and preferably
  $R^{61}$ has the meaning indicated above and preferably denotes $C_nH_{2n+1}$, in which
  n denotes an integer in the range from 1 to 7, preferably in the range from 1 to 5, and
  $X^{62}$ denotes F, Cl, OCF$_3$, or —CN.

The compounds of the formula VI-5 are preferably selected from the compounds of the formulae VI-5a to VI-5d, preferably VI-5b:

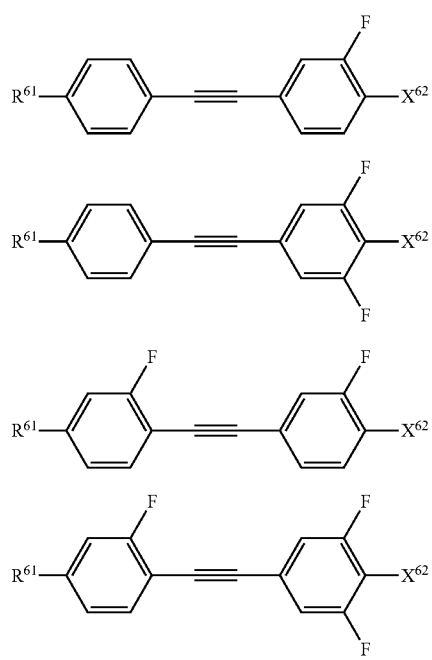

VI-5a

VI-5b

VI-5c

VI-5d in which the parameters have the meaning given above under formula VI-5 and preferably
  $R^{61}$ has the meaning indicated above and preferably denotes $C_nH_{2n+1}$, in which
  n denotes an integer in the range from 1 to 7, preferably in the range from 1 to 5, and
  $X^{62}$ denotes —F, —Cl, —OCF$_3$, or —CN, particularly preferably —OCF$_3$.

The compounds of the formula VII are preferably selected from the group of the compounds of the formulae VII-1 to VII-6:

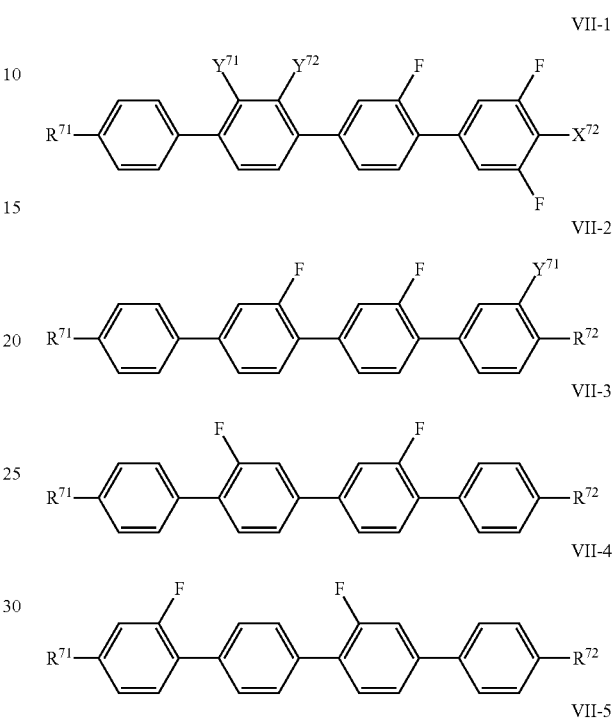

VII-1

VII-2

VII-3

VII-4

VII-5

VII-6

VII-7 where the compounds of the formula VII-5 are excluded from the compounds of the formula VII-6, and
in which the parameters have the respective meanings indicated above for formula VII,
$Y^{71}$, $Y^{72}$, $Y^{73}$ independently from one another, denote H or F,
and preferably
$R^{71}$ denotes unfluorinated alkyl or alkoxy, each having 1 to 7 C atoms, or unfluorinated alkenyl having 2 to 7 C atoms,
$R^{72}$ denotes unfluorinated alkyl or alkoxy, each having 1 to 7 C atoms, or unfluorinated alkenyl having 2 to 7 C atoms, $X^{72}$ denotes F, Cl; NCS or —OCF$_3$, preferably F or NCS, and particularly preferably $R^{71}$ has the meaning indicated above and preferably denotes $C_nH_{2n+1}$ or CH$_2$=CH—(CH$_2$)$_z$, and $R^{72}$ has the meaning indicated above and preferably denotes $C_mH_{2m+1}$ or O—$C_mH_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The compounds of the formula VII-1 are preferably selected from the group of the compounds of the formulae VII-1a to VII-1d:

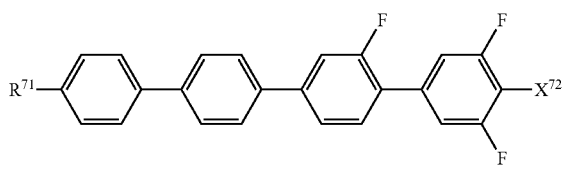

VII-1a

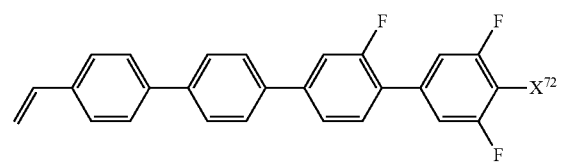

VII-1b

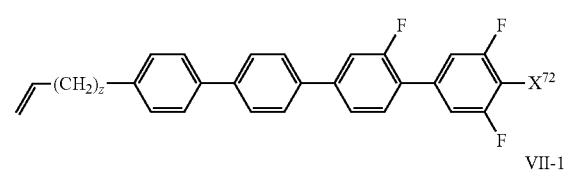

VII-1c

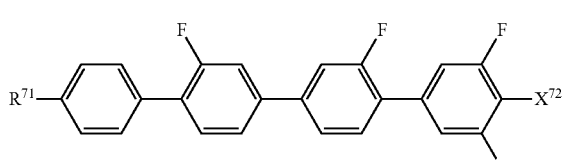

VII-1d in which $X^{72}$ has the meaning given above for formula VII-2 and $R^{71}$ has the meaning indicated above and preferably denotes $C_nH_{2n+1}$, in which n denotes 1 to 7, preferably 2 to 6, particularly preferably 2, 3 or 5, and z denotes 0, 1, 2, 3 or 4, preferably 0 or 2, and $X^{72}$ preferably denotes F.

The compounds of the formula VII-2 are preferably selected from the group of the compounds of the formulae VII-2a and VII-2b, particularly preferably of the formula VII-2a:

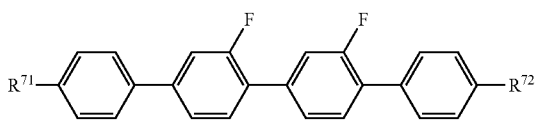

VII-2a

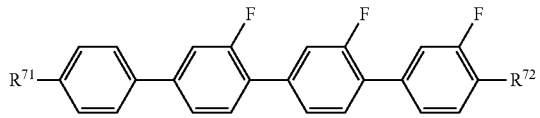

VII-2b in which $R^{71}$ has the meaning indicated above and preferably denotes $C_nH_{2n+1}$ or CH$_2$=CH—(CH$_2$)$_z$, and $R^{72}$ has the meaning indicated above and preferably denotes $C_mH_{2m+1}$ or O—$C_mH_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VII-3 are preferably compounds of the formula VII-3a:

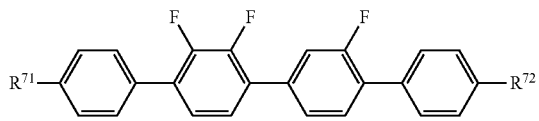

VII-3a in which $R^{71}$ has the meaning indicated above and preferably denotes $C_nH_{2n+1}$ or CH$_2$=CH—(CH$_2$)$_z$, and $R^{72}$ has the meaning indicated above and preferably denotes $C_mH_{2m+1}$ or O—$C_mH_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VII-4 are preferably compounds of the formula VII-4a:

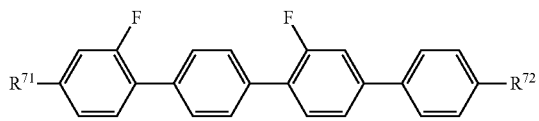

VII-4a in which $R^{71}$ has the meaning indicated above and preferably denotes $C_nH_{2n+1}$ or CH$_2$=CH—(CH$_2$)$_z$, and $R^{72}$ has the meaning indicated above and preferably denotes $C_mH_{2m+1}$ or O—$C_mH_{2m+1}$ or (CH$_2$)$_z$—CH=CH$_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VII-5 are preferably selected from the group of the compounds of the formulae VII-5a and VII-5b, more preferably of the formula VII-5a:

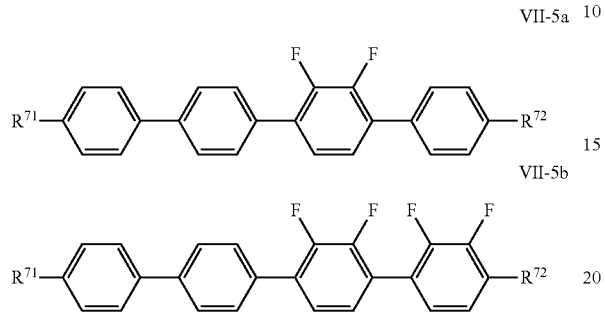

VII-5a

VII-5b in which
- $R^{71}$ has the meaning indicated above and preferably denotes $C_nH_{2n+1}$ or $CH_2$=CH—$(CH_2)_z$, and
- $R^{72}$ has the meaning indicated above and preferably denotes $C_mH_{2m+1}$ or O—$C_mH_{2m+1}$ or $(CH_2)_z$—CH=$CH_2$, and in which
- n and m, independently of one another, denote an integer in the range from 1 to 15, preferably in the range from 1 to 7 and particularly preferably 1 to 5, and
- z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VII-6 are preferably selected from the group of the compounds of the formulae VII-6a and VII-6b:

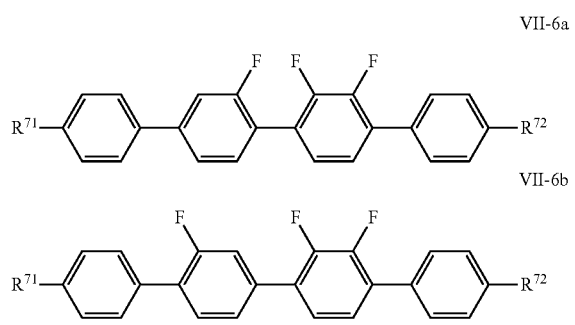

VII-6a

VII-6b in which
- $R^{71}$ has the meaning indicated above and preferably denotes $C_nH_{2n+1}$ or $CH_2$=CH—$(CH_2)_z$, and
- $R^{72}$ has the meaning indicated above and preferably denotes $C_mH_{2m+1}$ or O—$C_mH_{2m+1}$ or $(CH_2)_z$—CH=$CH_2$, and in which
- n and m, independently of one another, denote an integer in the range from 1 to 15, preferably in the range from 1 to 7 and particularly preferably 1 to 5, and
- z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

The compounds of the formula VII-7 are preferably selected from the group of the compounds of the formulae VII-7a to VII-7d:

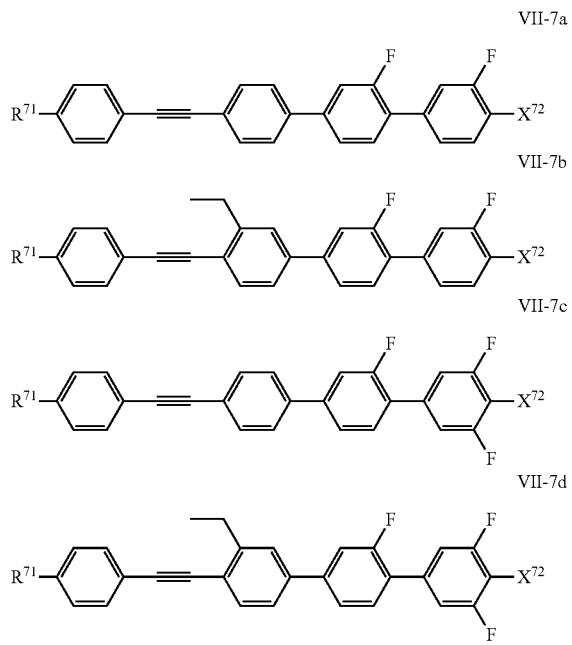

VII-7a

VII-7b

VII-7c

VII-7d in which
- $R^{71}$ has the meaning indicated above and preferably denotes $C_nH_{2n+1}$ or $CH_2$=CH—$(CH_2)_z$,
- $X^{72}$ denotes F, —$OCF_3$ or —NCS,
- n denotes an integer in the range from 1 to 15, preferably in the range from 1 to 7 and particularly preferably 1 to 5, and,
- z denotes 0, 1, 2, 3 or 4, preferably 0 or 2.

The compounds of the formula VIII are preferably selected from the group of the compounds of the formulae VIII-1 to VIII-3, more preferably these compounds of the formula VIII predominantly consist, even more preferably essentially consist and very particularly preferably completely consist thereof:

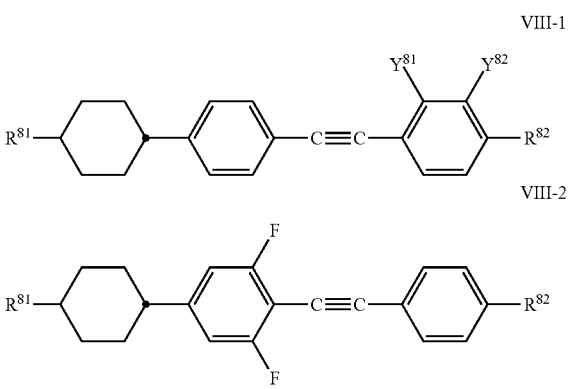

VIII-1

VIII-2

-continued

VIII-3

[chemical structure: cyclohexyl-phenyl-C≡C-difluorophenyl with R⁸¹ and R⁸² substituents]

in which
one of
Y⁸¹ and Y⁸² denotes H and the other denotes H or F, and
R⁸¹ has the meaning indicated above and preferably denotes $C_nH_{2n+1}$ or $CH_2=CH-(CH_2)_z$, and
R⁸² has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R⁸¹ and R⁸²) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VIII-1 are preferably selected from the group of the compounds of the formulae VIII-1a to VIII-1c:

VIII-1a

[chemical structure]

VIII-1b

[chemical structure with one F]

VIII-1c

[chemical structure with one F]

in which
R⁸¹ has the meaning indicated above and preferably denotes $C_nH_{2n+1}$ or $CH_2=CH-(CH_2)_z$, and
R⁸² has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R⁸¹ and R⁸²) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VIII-2 are preferably compounds of the formula VIII-2a:

VIII-2a

[chemical structure: cyclohexyl-difluorophenyl-C≡C-phenyl with R⁸¹ and R⁸²]

in which
R⁸¹ has the meaning indicated above and preferably denotes $C_nH_{2n+1}$ or $CH_2=CH-(CH_2)_z$, and
R⁸² has the meaning indicated above and preferably denotes $C_mH_{2m+1}$, or $O-C_mH_{2m+1}$ or $(CH_2)_z-CH=CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R⁸¹ and R⁸²) here are, in particular, ($C_nH_{2n+1}$ and $C_mH_{2m+1}$), ($C_nH_{2n+1}$ and $O-C_mH_{2m+1}$) and ($CH_2=CH-(CH_2)_z$ and $C_mH_{2m+1}$), particularly preferably ($C_nH_{2n+1}$ and $C_mH_{2m+1}$).

The compounds of the formula VIII-3 are preferably compounds of the formula VIII-3a:

VIII-3a

[chemical structure]

in which
R⁸¹ has the meaning indicated above and preferably denotes $C_nH_{2n+1}$ or $CH_2=CH-(CH_2)_z$, and
R⁸² has the meaning indicated above and preferably denotes $C_mH_{2m+1}$ or $O-C_mH_{2m+1}$ or $(CH_2)_z-CH=CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of (R⁸¹ and R⁸²) here are, in particular, ($C_nH_{2n+1}$ and $C_mH_{2m+1}$) and ($C_nH_{2n+1}$ and $O-C_mH_{2m+1}$).

The compounds of the formula IX are preferably selected from the group of the compounds of the formulae IX-1 to IX-3:

IX-1

[chemical structure: R⁹¹-A⁹¹-A⁹²-fluorophenyl-A⁹⁴-X⁹²]

IX-2

[chemical structure: R⁹¹-A⁹¹-A⁹²-A⁹³-A⁹⁴-R⁹²]

-continued

IX-3

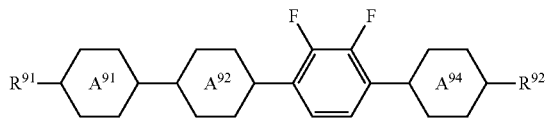

in which the parameters have the respective meaning indicated above under formula IX and preferably one of

to

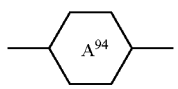

denotes

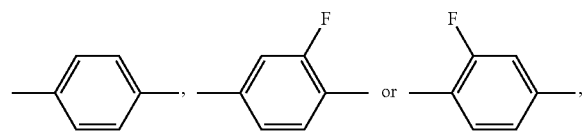

and
in which
$R^{91}$ has the meaning indicated above and preferably denotes $C_nH_{2n+1}$ or $CH_2$=CH—$(CH_2)_z$, and
$R^{92}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and O—$C_mH_{2m+1}$).

The compounds of the formula IX-1 are preferably selected from the group of the compounds of the formulae IX-1a to IX-1e:

IX-1a

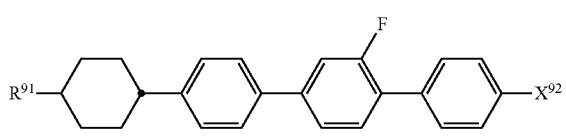

IX-1b

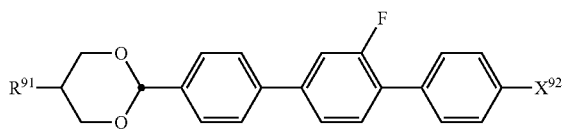

IX-1c

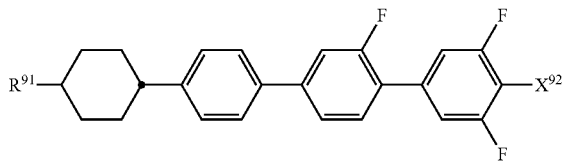

IX-1d

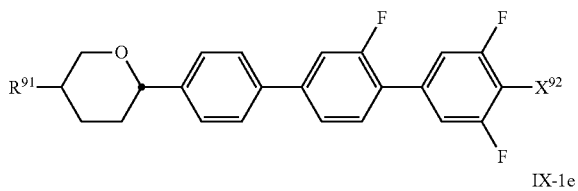

IX-1e

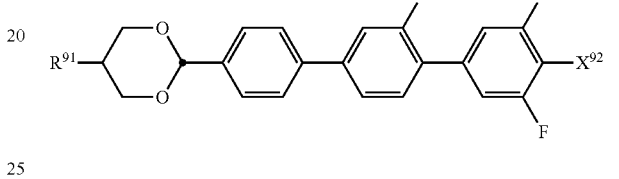

in which the parameters have the meaning given above and preferably
$R^{91}$ has the meaning indicated above and preferably denotes $C_nH_{2n+1}$, and
n denotes an integer in the range from 1 to 15, preferably in the range from 1 to 7 and particularly preferably 1 to 5, and
$X^{92}$ preferably denotes F or Cl.

The compounds of the formula IX-2 are preferably selected from the group of the compounds of the formulae IX-2a and IX-2b:

IX-2a

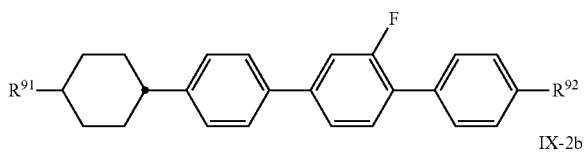

IX-2b

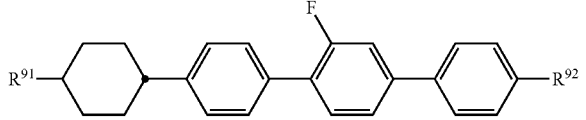

in which
$R^{91}$ has the meaning indicated above and preferably denotes $C_nH_{2n+1}$ or $CH_2$=CH—$(CH_2)_z$, and
$R^{92}$ has the meaning indicated above and preferably denotes $C_mH_{2m+1}$ or O—$C_mH_{2m+1}$ or $(CH_2)_z$—CH=$CH_2$, and in which
n and m, independently of one another, denote an integer in the range from 1 to 15, preferably in the range from 1 to 7 and particularly preferably 1 to 5, and
z denotes 0, 1, 2, 3 or 4, preferably 0 or 2.

The preferred combination of ($R^{91}$ and $R^{92}$) here is, in particular, ($C_nH_{2n+1}$ and $C_mH_{2m+1}$).

The compounds of the formula IX-3 are preferably compounds of the formulae IX-3a and IX-3b:

IX-3a

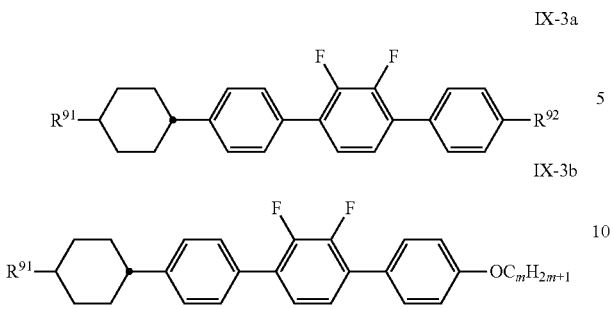

IX-3b in which

R⁹¹ has the meaning indicated above and preferably denotes $C_nH_{2n+1}$ or $CH_2=CH—(CH_2)_z$, and R⁹² has the meaning indicated above and preferably denotes $C_mH_{2m+1}$ or $O—C_mH_{2m+1}$ or $(CH_2)_z—CH=CH_2$, and in which n and m, independently of one another, denote an integer in the range from 1 to 15, preferably in the range from 1 to 7 and particularly preferably 1 to 5, and z denotes 0, 1, 2, 3 or 4, preferably 0 or 2.

The preferred combinations of (R⁹¹ and R⁹²) here are, in particular, ($C_nH_{2n+1}$ and $C_mH_{2m+1}$) and ($C_nH_{2n+1}$ and $O—C_mH_{2m+1}$), particularly preferably ($C_nH_{2n+1}$ and $O—C_mH_{2m+1}$).

In a preferred embodiment of the present invention the medium comprises one or more compounds of formula X

X

in which

R¹⁰¹ denotes H, alkyl or alkoxy having 1 to 15, preferably 3 to 10, C atoms or unfluorinated alkenyl, unfluorinated alkenyloxy or unfluorinated alkoxyalkyl having 2 to 15, preferably 3 to 10, C atoms, preferably alkyl or alkenyl, X¹⁰¹ denotes H, F, Cl, —CN, SF₅, NCS, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F, Cl or NCS, particularly preferably NCS, Y¹⁰¹ denotes methyl, ethyl or Cl, Y¹⁰² denotes H, methyl, ethyl, F or Cl, preferably H or F, Z¹⁰¹, Z¹⁰² identically or differently, denote a single bond, —CH=CH—, —CF=CF— or —C≡C—,

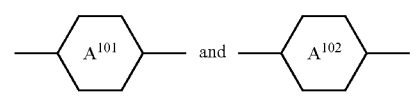

independently of one another, denote

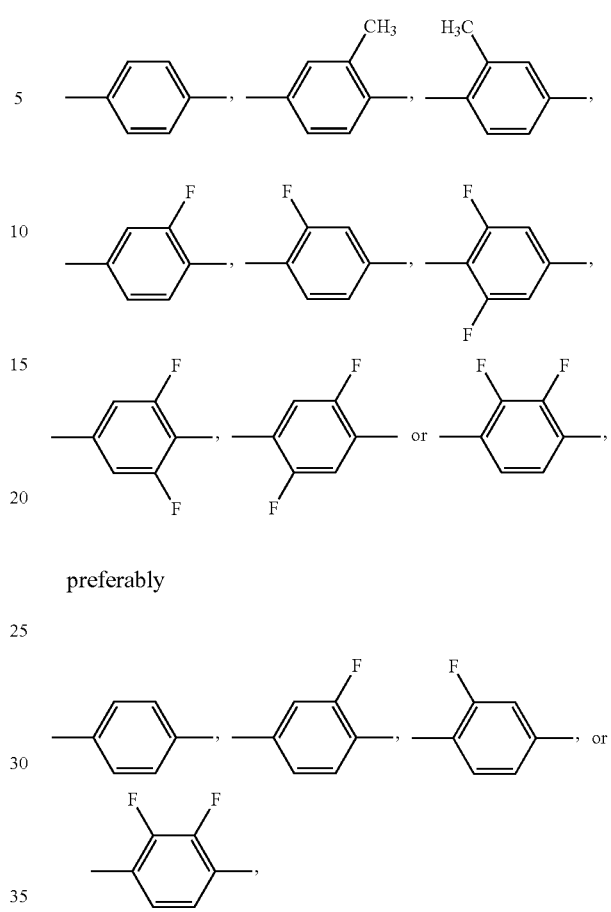

preferably and where

alternatively denotes and n is 0 or 1.

Preferably, the compounds of formula X are selected from the sub-formulae X-1 and X-2

X-1

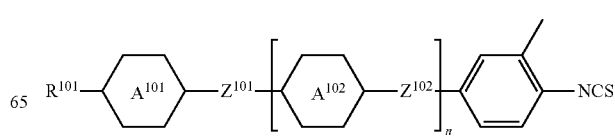

X-2

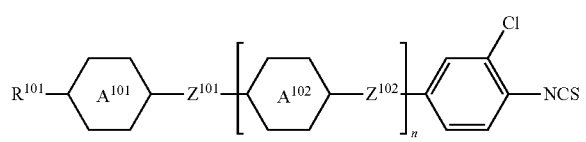

in which the occurring groups and parameters have the meanings given above for formula X.

Particularly preferably, the media according to the invention comprise one or more compounds selected from the group of compounds of the formulae X-1-1 to X-1-9

X-1-1

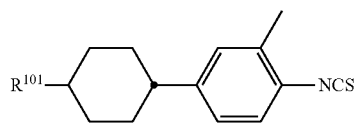

X-1-2

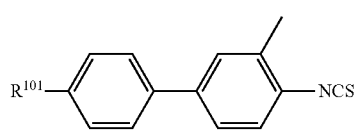

X-1-6

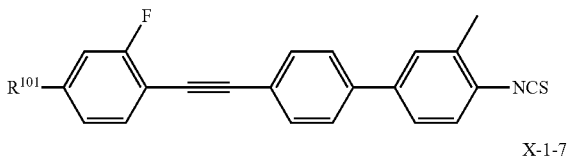

X-1-7

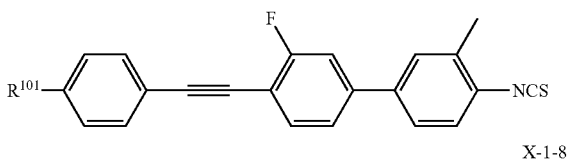

X-1-8

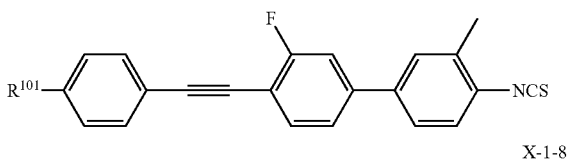

X-1-9

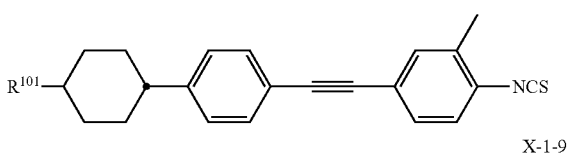

In a preferred embodiment, the medium according to the invention comprises one or more compounds of formula XI

XI

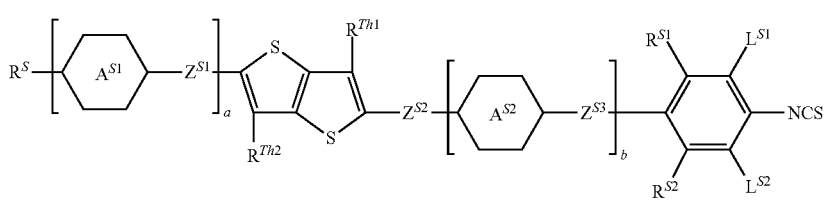

X-1-3

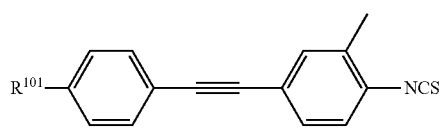

X-1-4

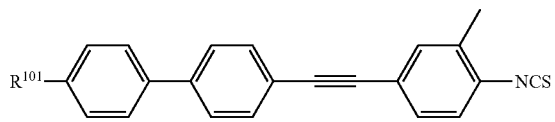

X-1-5

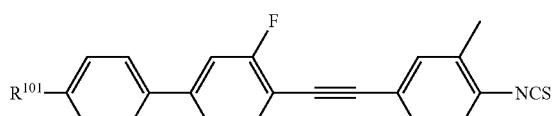

in which
$R^S$ denotes H, alkyl or alkoxy having 1 to 12 C atoms, or alkenyl, alkenyloxy or alkoxyalkyl having 2 to 12 C atoms, in which one or more $CH_2$-groups may be replaced by

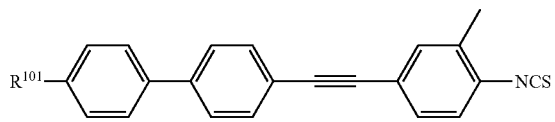

and in which one or more H atoms may be replaced by F,

—⟨$A^{S1}$⟩— and —⟨$A^{S2}$⟩—, on each occurrence, independently of one another, denote

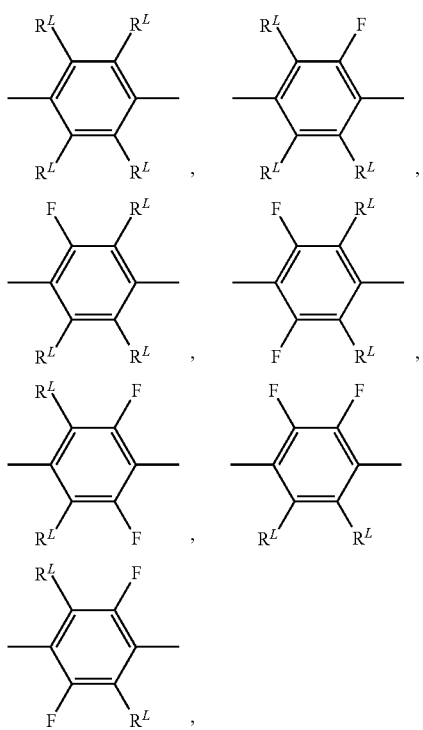

in which $R^L$, on each occurrence identically or differently, denotes H, Cl or straight chain, branched or cyclic alkyl having 1 to 6 C atoms, $L^{S1}$, $L^{S2}$ identically or differently, denote H, Cl or F, $R^{S1}$, $R^{S2}$, identically or differently, denote H, alkyl or alkenyl, having up to 6 C atoms, or cyclopropyl, cyclobutyl, cyclopentenyl, or cyclopentyl, $R^{Th1}$, $R^{Th2}$ identically or differently, denote H, alkyl or alkenyl or alkoxy, having up to 6 C atoms, or cyclopropyl, cyclobutyl, cyclopentenyl or cyclopentyl, $Z^{S1}$, $Z^{S2}$, $Z^{S3}$ identically or differently, denote —CH=CH—, —CH=CF—, —CF=CH—, —CF=CF—, —C≡C—, or a single bond, a, b identically or differently, are 0 or 1.

Preferably, the compounds of formula XI are selected from the group of compounds of the formulae XI-1 to XI-24:

XI-1
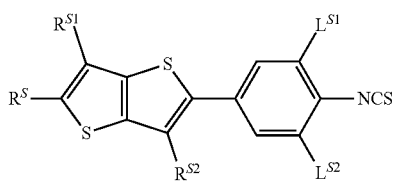

XI-2
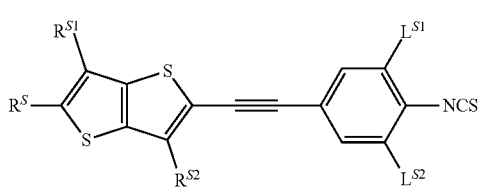

XI-3
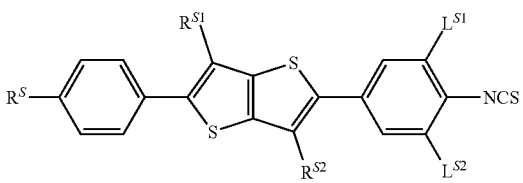

XI-4
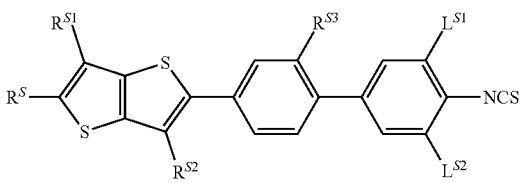

XI-5
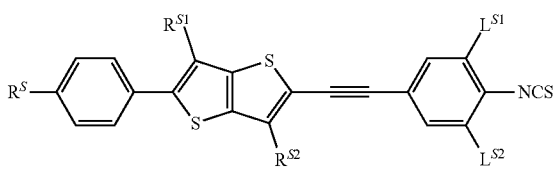

XI-6
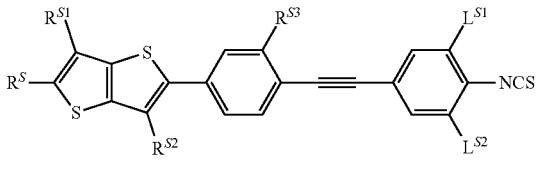

XI-7
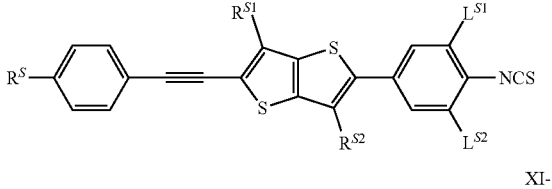

XI-8
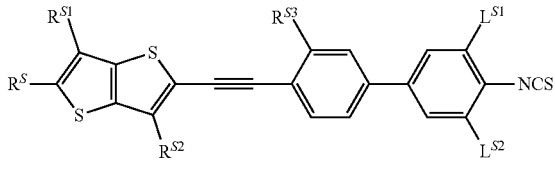

XI-9
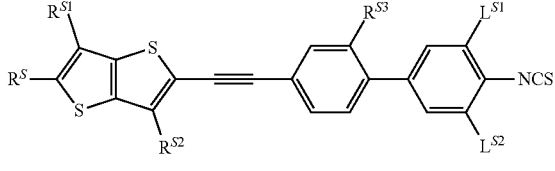

XI-10
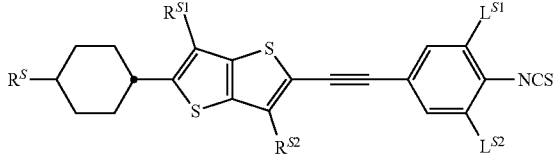

-continued
XI-11
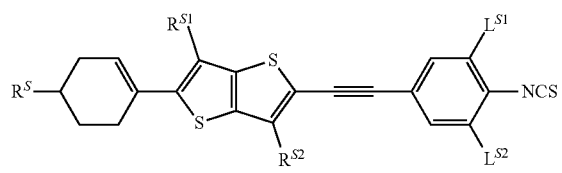
XI-12
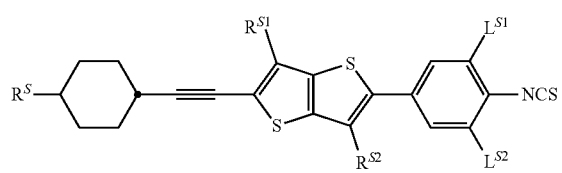
XI-13
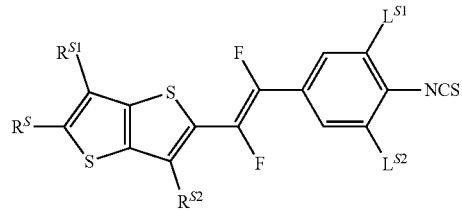
XI-14
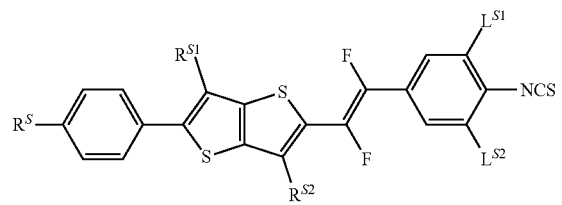
XI-15
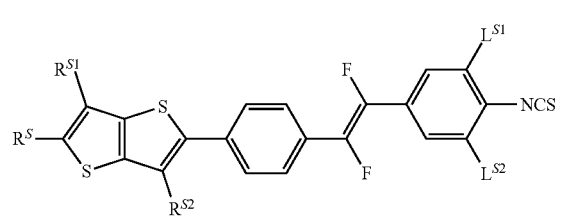
XI-16
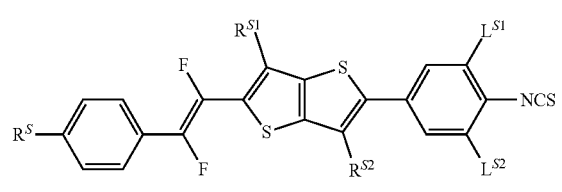
XI-17
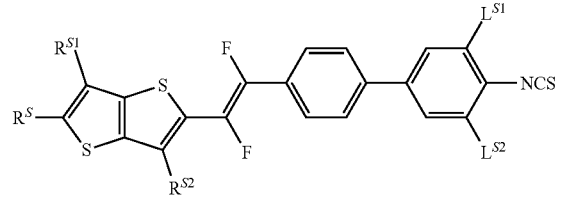
XI-18
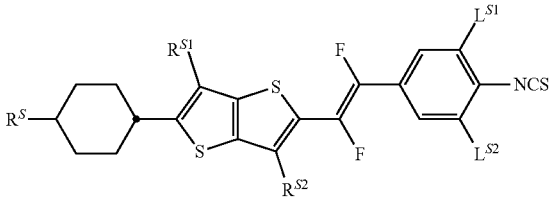
XI-19
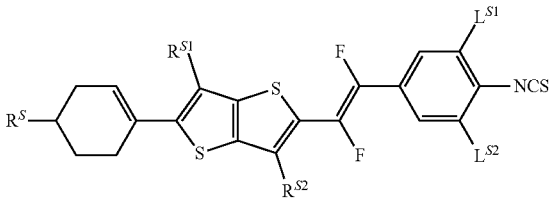
XI-20
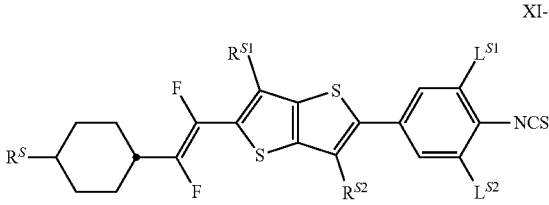
XI-21
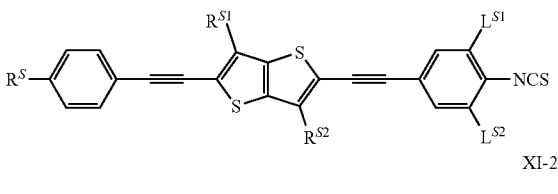
XI-22
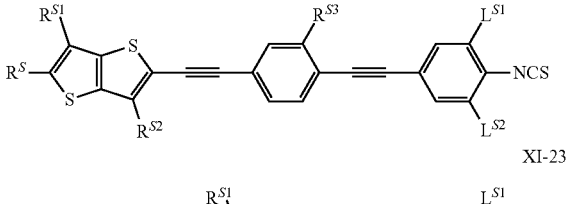
XI-23
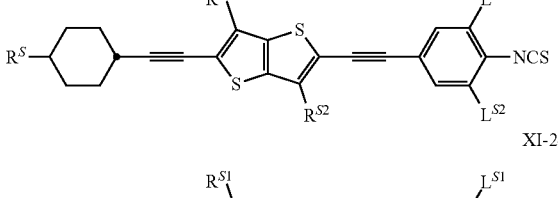
XI-24
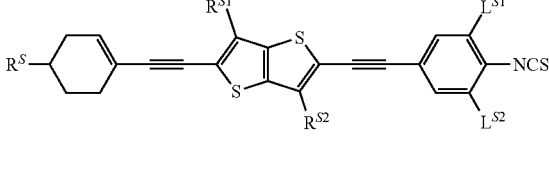
in which the occurring groups have the meanings given above for formula XI and preferably
$R^S$ denotes alkyl or alkenyl having 2 to 6 C atoms, in which one or more CH$_2$-groups may be replaced by
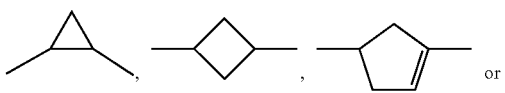
, , or -continued

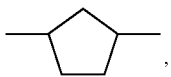

$R^{S1}$ and $R^{S2}$ identically or differently, denote H or alkyl having 1 to 6 C atoms, preferably H, $R^{S3}$ denotes H, F or alkyl, having up to 6 C atoms, or cyclopropyl, preferably H, F or ethyl, very preferably H, $L^{S1}$ and $L^{S2}$ identically or differently, denote H or F, preferably F.

In a preferred embodiment, the medium comprises one or more compounds of formula XII

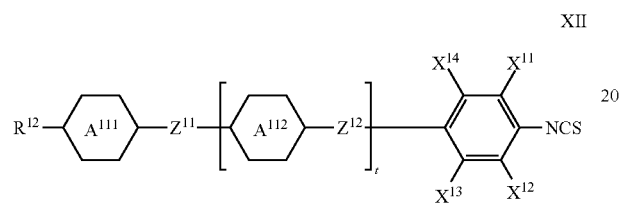

XII in which $R^{12}$ denotes H, alkyl or alkoxy having 1 to 12 C atoms, or alkenyl, alkenyloxy or alkoxyalkyl having 2 to 12 C atoms, in which one or more CH$_2$-groups may be replaced by

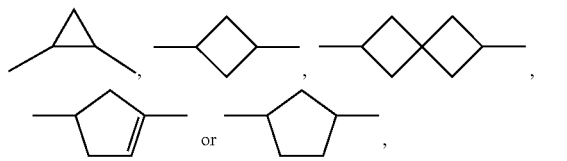

or a group $R^P$, $R^P$ denotes halogen, CN, NCS, $R^F$, $R^F$—O— or $R^F$—S—, wherein $R^F$ denotes fluorinated alkyl or fluorinated alkenyl having up to 9 C atoms, $Z^{11}$, $Z^{12}$ identically or differently, denote —CH=CH—, —CF=CF—, —CH=CF—, —CF=CH—, —C≡C— or a single bond, preferably —C≡C— or a single bond, $X1^1$, $X1^2$, $X1^3$ and $X1^4$ identically or differently, denote Cl or F, preferably F, t is 0 or 1, and

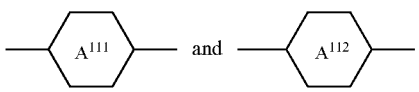

denote a radical selected from the following groups:

a) the group consisting of 1,4-phenylene, 1,4-naphthylene, and 2,6-naphthylene, in which one or two CH groups may be replaced by N and in which one or more H atoms may be replaced by L, wherein tetrafluoro-1,4-phenylene is excluded, b) the group consisting of trans-1,4-cyclohexylene, 1,4-cyclohexenylene, bicyclo[1.1.1]pentane-1,3-diyl, 4,4'-bicyclohexylene, bicyclo[2.2.2]octane-1,4-diyl, spiro[3.3]heptane-2,6-diyl, in which one or more non-adjacent CH$_2$ groups may be replaced by —O— and/or —S— and in which one or more H atoms may be replaced by F, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms.

The compounds of formula XII are preferably selected from the group of compounds of the sub-formulae XII-1 to XII-11

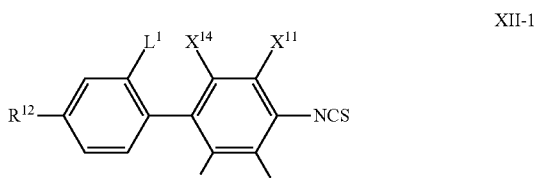

XII-1

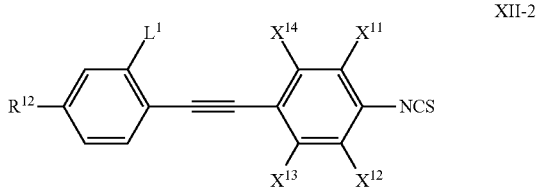

XII-2

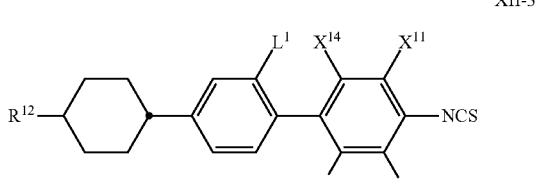

XII-3

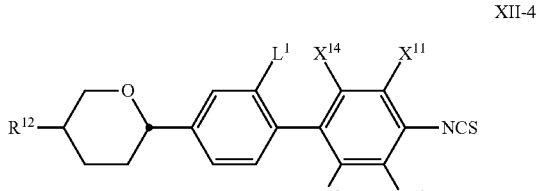

XII-4

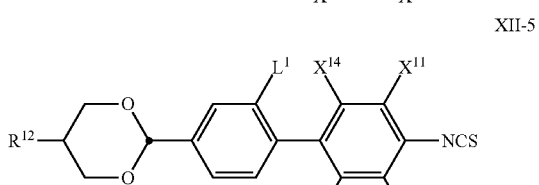

XII-5

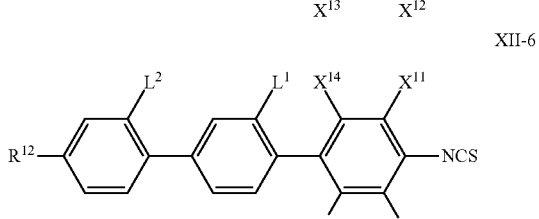

XII-6

-continued

XII-7
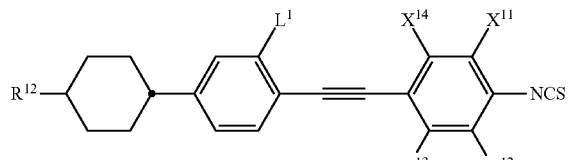

XII-8
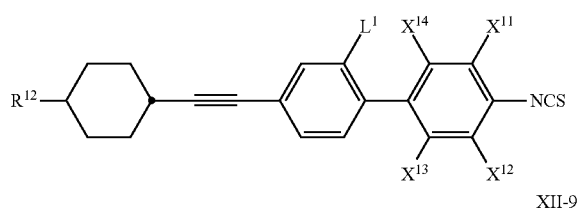

XII-9
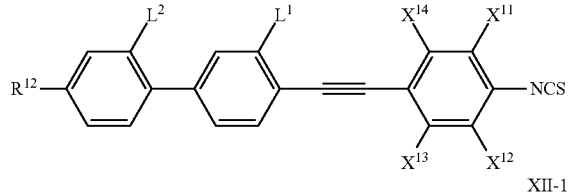

XII-10
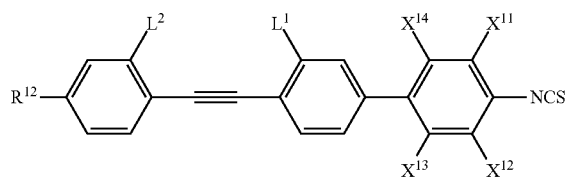

XII-11
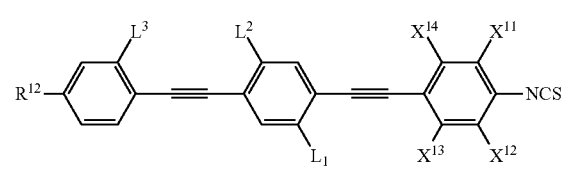

in which
L$^1$, L$^2$ and L$^3$ identically or differently, denote H, F, Cl, methyl, ethyl, n-propyl, isopropyl, cyclopropyl, cyclobutyl, cyclopentyl or cyclopentenyl, and
R$^T$, X$^{11}$, X$^{12}$, X$^{13}$ and X$^{14}$ have the meanings given above, very preferably RT denotes alkyl having 1 to 7 C atoms and X$^{11}$, X$^{12}$, X$^{13}$ and X$^{14}$ denote F.

In a preferred embodiment, the medium according to the invention comprises one or more compounds of formula T T
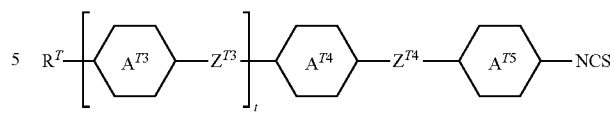

in which
R$^T$ denotes halogen, CN, NCS, R$^F$, R$^F$—O— or R$^F$—S—, wherein
R$^F$ denotes fluorinated alkyl or fluorinated alkenyl having up to 12 C atoms,

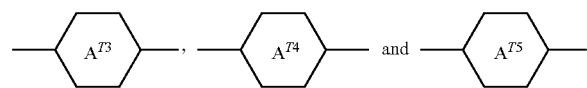

on each occurrence, independently of one another, denote

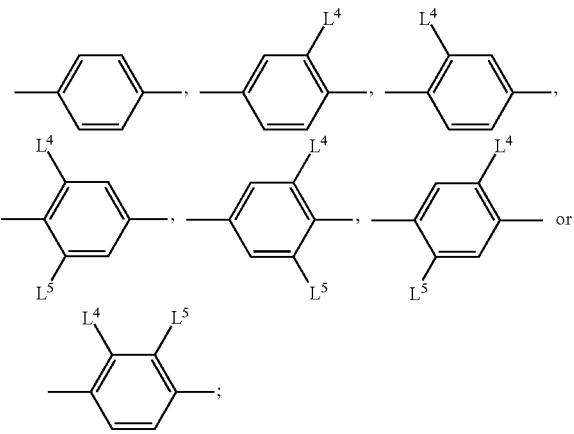

L$^4$ and L$^5$ identically or differently, denote F, Cl or straight chain or branched or cyclic alkyl or alkenyl each having up to 12 C atoms;
Z$^{T3}$, Z$^{T4}$ identically or differently, denote —CH═CH—, —CF═CF—, —CH═CF—, —CF═CH—, —C≡C— or a single bond, and
t is 0 or 1.

In a preferred embodiment, the liquid crystalline media according to the invention comprise one or more compounds selected from the group of compounds of the formulae T-1a to T-3b below:

T-1a
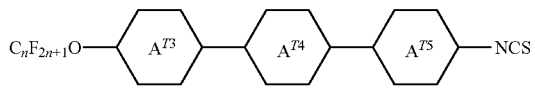

T-1b
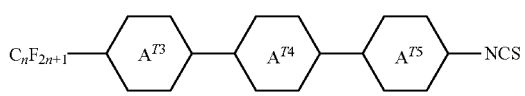

T-2a
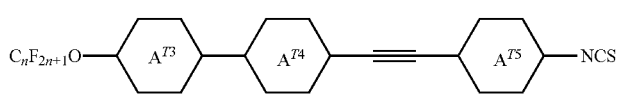

T-2b
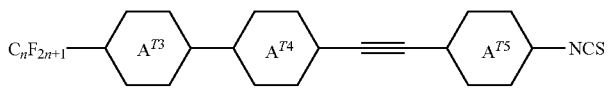

T-3a
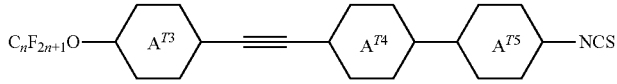

T-3b
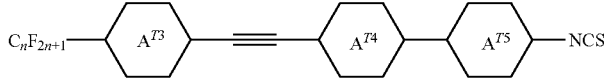

T-4a
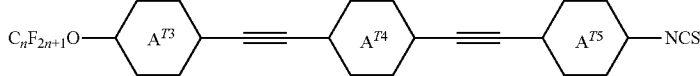

T-4b
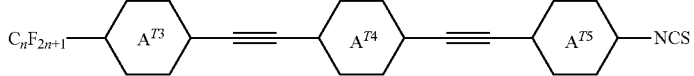

in which

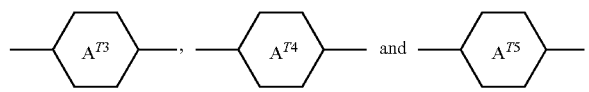

have the meanings given above and n is 1, 2, 3, 4, 5, 6 or 7, preferably 1, 2, 3 or 4, particularly preferably 1.

In a particularly preferred embodiment of the present invention the media comprise one or more compounds selected from the compounds of the formulae T-1a and T-2a.

Preferred compounds of formula T-1a are selected from the group of compounds of the following sub-formulae:

T-1a-1
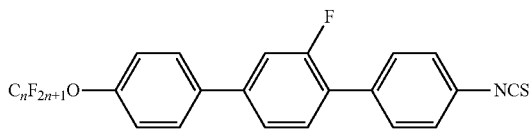

T-1a-2
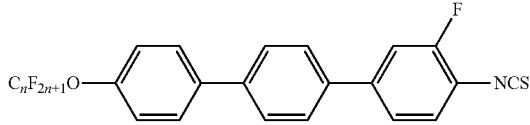

T-1a-3
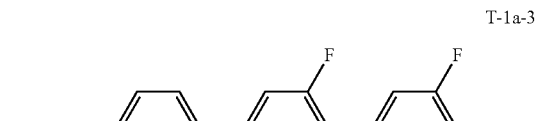

T-1a-4
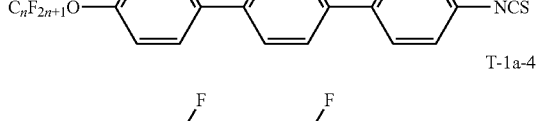

T-1a-5
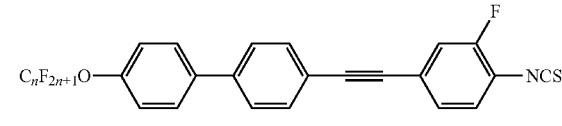

T-1a-6
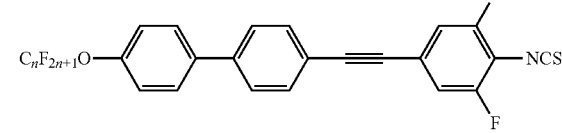

in which n is 1, 2, 3 or 4, preferably 1.

Preferred compounds of formula T-2a are selected from the group of compounds of the following sub-formulae:

T-2a-1

T-2a-2

T-2a-3
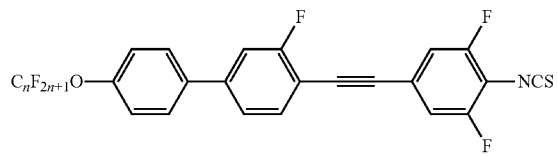

T-2a-4
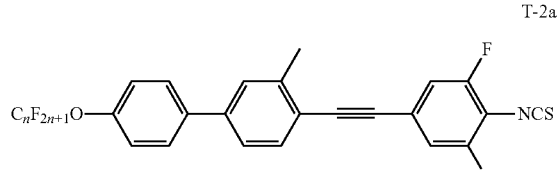

T-2a-5
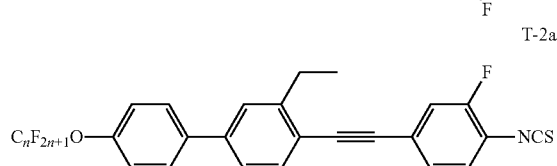

T-2a-6
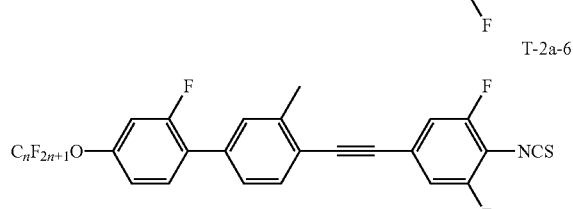

in which n is 1, 2, 3 or 4, preferably 1.

Very preferably, the medium according to the invention comprises one or more compounds of formula T-1a-5.

In an embodiment, the medium according to the invention comprises one or more compounds of formula I, II, III, IV, V, VI, VII, VIII, IX, X in which the radical $R^1$, $R^2$, $R^3$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$, $R^{101}$, $R^{102}$ and $R^S$, respectively, is a cyclic alkyl group.

Very preferred compounds comprising a cyclic alkyl group are selected from the compounds of the formulae Cy-1 to Cy-14

Cy-1
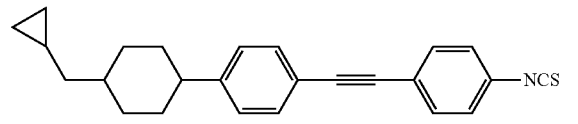

Cy-2
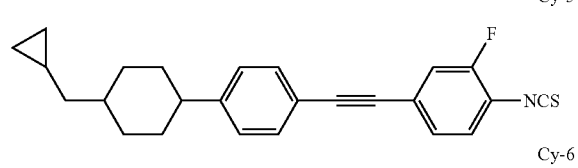

Cy-3
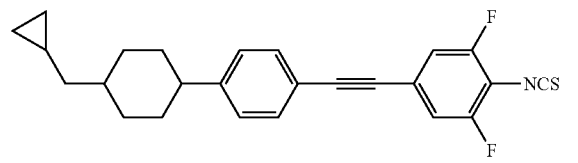

Cy-4

Cy-5
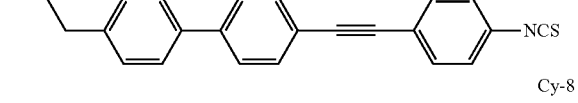

Cy-6
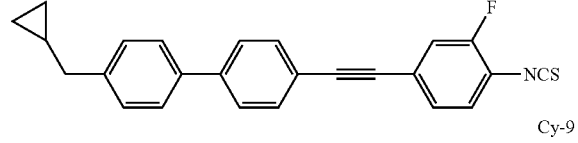

Cy-7
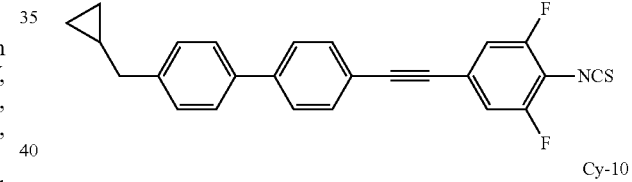

Cy-8
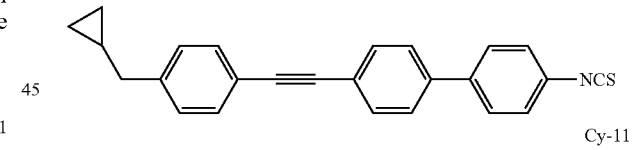

Cy-9
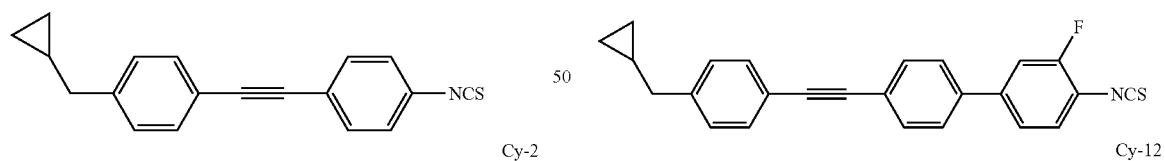

Cy-10
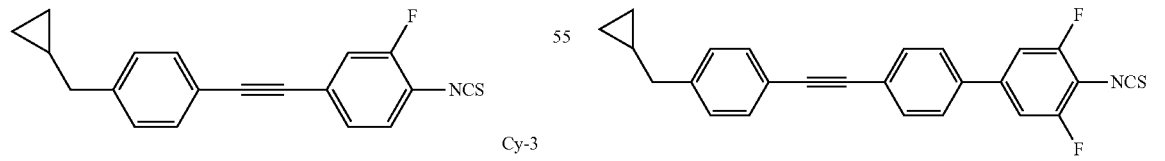

Cy-11

Cy-12

Cy-13
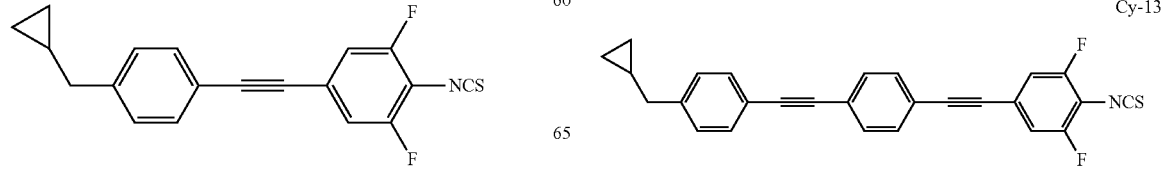

-continued

Cy-14

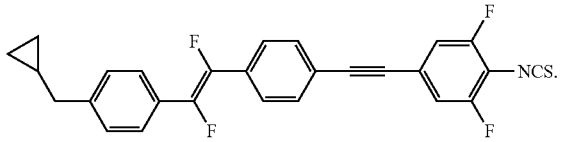

The media according to the present invention comprise one or more chiral dopants. Preferably these chiral dopants have an absolute value of the helical twisting power (HTP) in the range of from 1 μm$^{-1}$ to 150 μm$^{-1}$, preferably in the range of from 10 μm$^{-1}$ to 100 μm$^{-1}$. In case the media comprise two or more chiral dopants, these may have opposite signs of their HTP-values. This condition is preferred for some specific embodiments, as it allows to compensate the chirality of the respective compounds to some degree and, thus, may be used to compensate various temperature dependent properties of the resulting media in the devices. Generally, however, it is preferred that most, preferably all of the chiral compounds present in the media according to the present invention have the same sign of their HTP-values.

Preferably the chiral dopants present in the media according to the instant application are mesogenic compounds and most preferably they exhibit a mesophase on their own.

In a preferred embodiment of the present invention, the medium comprises two or more chiral compounds which all have the same algebraic sign of the HTP.

The temperature dependence of the HTP of the individual compounds may be high or low. The temperature dependence of the pitch of the medium can be compensated by mixing compounds having different temperature dependencies of the HTP in corresponding ratios.

For the optically active component, a multitude of chiral dopants, some of which are commercially available, is available to the person skilled in the art, such as, for example, cholesteryl nonanoate, R- and S-811, R- and S-1011, R- and S-2011, R- and S-3011, R- and S-4011, or CB15 (all Merck KGaA, Darmstadt).

Particularly suitable dopants are compounds which contain one or more chiral groups and one or more mesogenic groups, or one or more aromatic or alicyclic groups which form a mesogenic group with the chiral group.

Suitable chiral groups are, for example, chiral branched hydrocarbon radicals, chiral ethane diols, binaphthols or dioxolanes, furthermore mono- or polyvalent chiral groups selected from the group consisting of sugar derivatives, sugar alcohols, sugar acids, lactic acids, chiral substituted glycols, steroid derivatives, terpene derivatives, amino acids or sequences of a few, preferably 1-5, amino acids.

Preferred chiral groups are sugar derivatives, such as glucose, mannose, galactose, fructose, arabinose and dextrose; sugar alcohols, such as, for example, sorbitol, mannitol, iditol, galactitol or anhydro derivatives thereof, in particular dianhydrohexitols, such as dianhydrosorbide (1,4:3,6-dianhydro-D-sorbide, isosorbide), dianhydromannitol (isosorbitol) or dianhydroiditol (isoiditol); sugar acids, such as, for example, gluconic acid, gulonic acid and ketogulonic acid; chiral substituted glycol radicals, such as, for example, mono- or oligoethylene or propylene glycols, in which one or more CH$_2$ groups are substituted by alkyl or alkoxy; amino acids, such as, for example, alanine, valine, phenylglycine or phenylalanine, or sequences of from 1 to 5 of these amino acids; steroid derivatives, such as, for example, cholesteryl or cholic acid radicals; terpene derivatives, such as, for example, menthyl, neomenthyl, campheyl, pineyl, terpineyl, isolongifolyl, fenchyl, carreyl, myrthenyl, nopyl, geraniyl, linaloyl, neryl, citronellyl or dihydrocitronellyl.

The media according to the present invention preferably comprise chiral dopants which are selected from the group of known chiral dopants. Suitable chiral groups and mesogenic chiral compounds are described, for example, in DE 34 25 503, DE 35 34 777, DE 35 34 778, DE 35 34 779 and DE 35 34 780, DE 43 42 280, EP 01 038 941 and DE 195 41 820. Examples are also compounds listed in Table F below.

Chiral compounds preferably used according to the present invention are selected from the group consisting of the formulae shown below.

Particular preference is given to chiral dopants selected from the group consisting of compounds of the following formulae A-I to A-III and A-Ch:

A-I

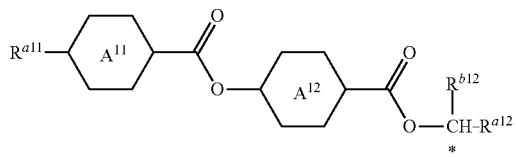

A-II

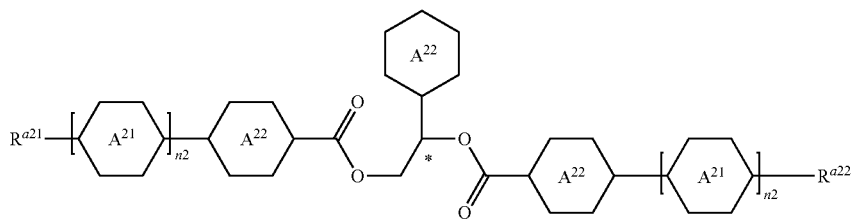

A-III

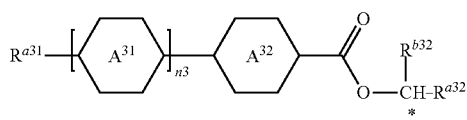

-continued

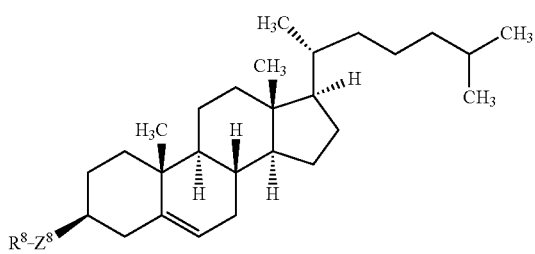

in which $R^{a11}$, $R^{a12}$ and $R^{b12}$, independently of one another, denote alkyl having 1 to 15 C atoms, in which, in addition, one or more non-adjacent CH$_2$ groups may each be replaced, independently of one another, by —C(R$^z$)=C(R$^z$)—, —C≡C—, —O—, —S—, —CO—, —CO—O—, —O—CO— or —O—CO—O— in such a way that O and/or S atoms are not linked directly to one another, and in which, in addition, one or more H atoms may each be replaced by F, Cl, Br, I or CN, preferably alkyl, more preferably n-alkyl, with the proviso that $R^{a12}$ is different from $R^{b12}$ $R^{a21}$ and $R^{a22}$, independently of one another, denote alkyl having 1 to 15 C atoms, in which, in addition, one or more non-adjacent CH$_2$ groups may each be replaced, independently of one another, by —C(R$^z$)=C(R$^z$)—, —C≡C—, —O—, —S—, —CO—, —O—CO—, —O—CO— or —O—CO—O— in such a way that O and/or S atoms are not linked directly to one another, and in which, in addition, one or more H atoms may be replaced by F, Cl, Br, I or CN, preferably both are alkyl, more preferably n-alkyl, $R^{a31}$, $R^{a32}$ and $R^{b32}$, independently of one another, denote straight-chain or branched alkyl having 1 to 15 C atoms, in which, in addition, one or more non-adjacent CH$_2$ groups may each be replaced, independently of one another, by —C(R$^z$)=C(R$^z$)—, —C≡C—, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN, preferably alkyl, more preferably n-alkyl, with the proviso that $R^{a32}$ is different from $R^{b32}$;

$R^z$ denotes H, CH$_3$, F, Cl, or CN, preferably H or F, $R^8$ has one of the meanings of $R^{a11}$ given above, preferably alkyl, more preferably n-alkyl having 1 to 15 C atoms, $Z^8$ denotes —C(O)O—, CH$_2$O, CF$_2$O or a single bond, preferably —C(O)O—, $A^{11}$ is defined as $A^{12}$ below, or alternatively denotes

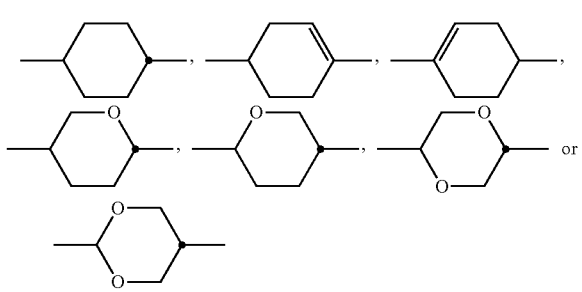

A-Ch $A^{12}$ denotes

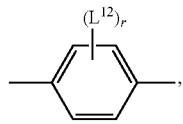

preferably

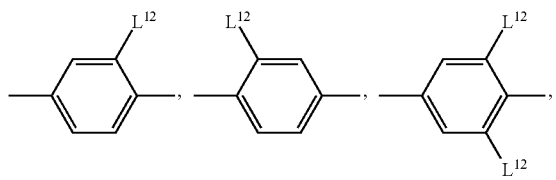

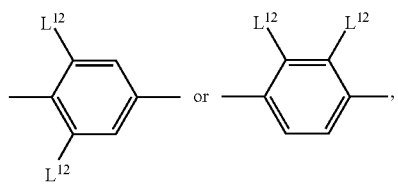

in which $L^{12}$ on each occurrence, independently of one another, denotes halogen, CN, or alkyl, alkenyl, alkoxy or alkenyloxy having up to 12 C atoms and in which one or more H atoms are optionally replaced with halogen, preferably methyl, ethyl, Cl or F, particularly preferably F, $A^{21}$ denotes

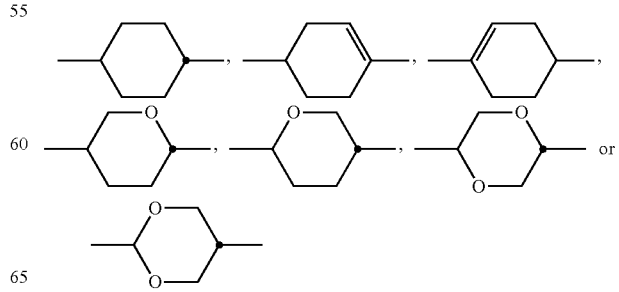

$A^{22}$ has the meanings given for $A^{12}$
$A^{31}$ has the meanings given for $A^{11}$, or alternatively denotes

$A^{32}$ has the meanings given for $A^{12}$.

n2 on each occurrence, identically or differently, is 0, 1 or 2, and n3 is 1, 2 or 3, and r is 0, 1, 2, 3 or 4.

Particular preference is given to dopants selected from the group consisting of the compounds of the following formulae:

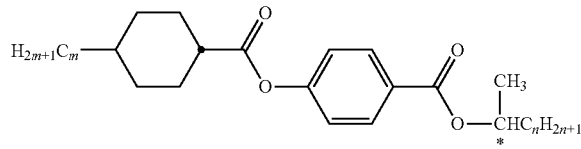
A-I-1

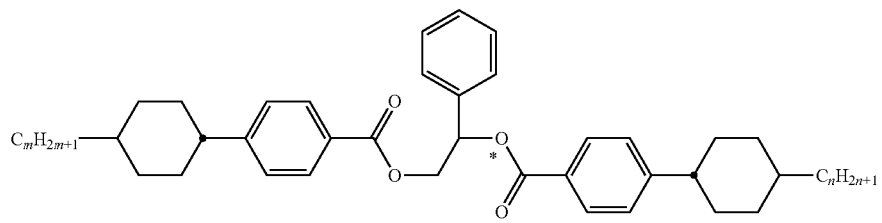
A-II-1

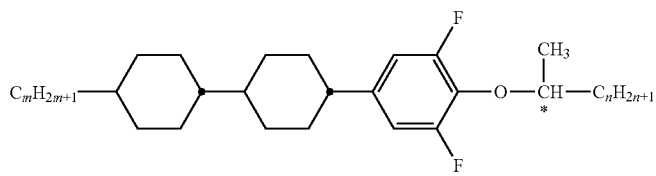
A-III-1

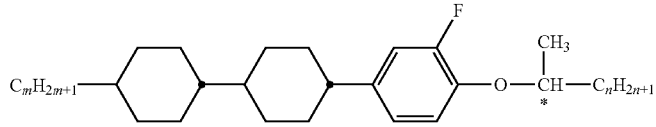
A-III-2

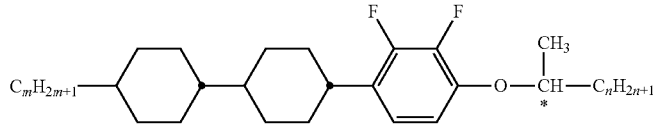
A-III-3

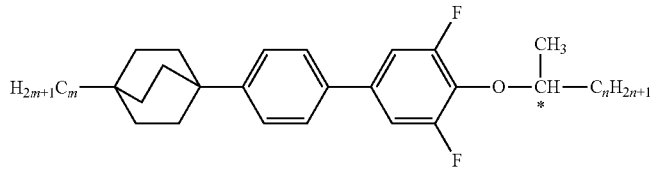
A-III-4

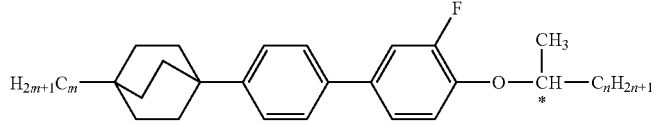
A-III-5

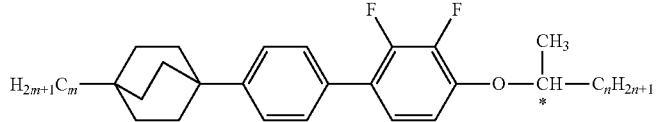
A-III-6

-continued

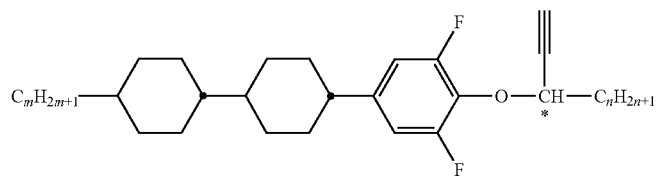

A-III-7

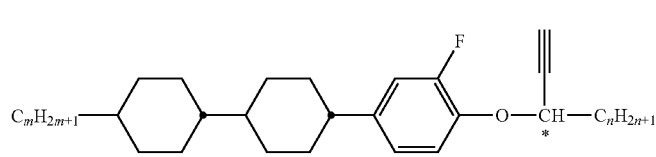

A-III-8

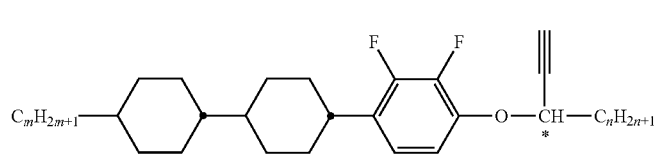

A-III-9 in which m is, on each occurrence, identically or differently, an integer from 1 to 9 and n is, on each occurrence, identically or differently, an integer from 2 to 9.

Particularly preferred compounds of formula A are compounds of formula A-III. Further preferred dopants are derivatives of the isosorbide, isomannitol or isoiditol of the following formula A-IV:

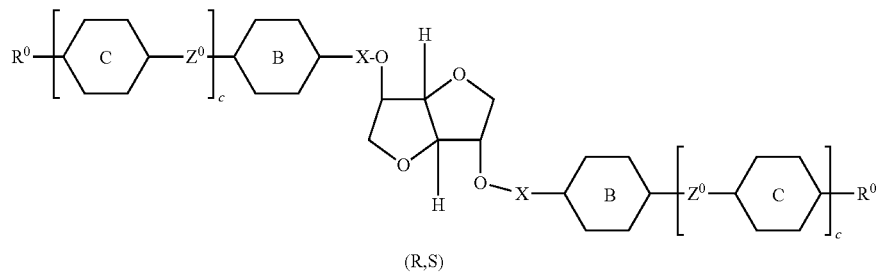

A-IV in which the group

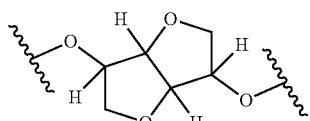

is

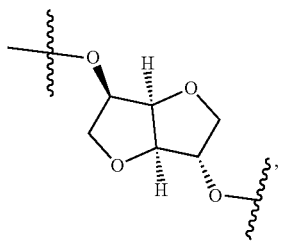
(dianhydrosorbitol)

-continued

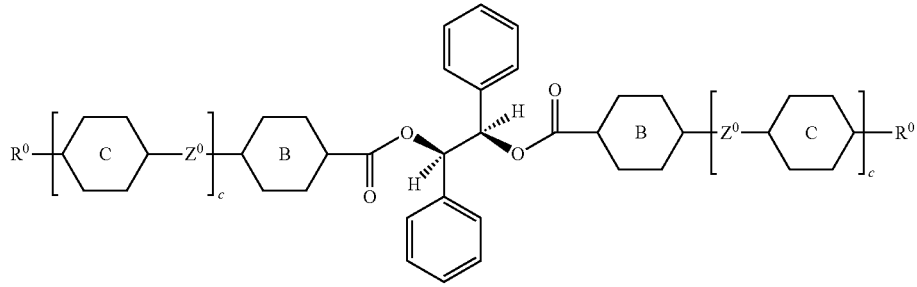
(dianhydromannitol)

, or

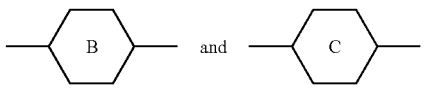
(dianhydroiditol)

preferably dianhydrosorbitol,
and chiral ethane diols, such as, for example, diphenylethanediol (hydrobenzoin), in particular mesogenic hydrobenzoin derivatives of the following formula A-V:

A-V including the (S,S) enantiomers, which are not shown,
in which

— B — and — C — are each, independently of one another, 1,4-phenylene, which may also be mono-, di- or trisubstituted by L, or 1,4-cyclohexylene, L is H, F, Cl, CN or optionally halogenated alkyl, alkoxy, alkylcarbonyl, alkoxycarbonyl or alkoxycarbonyloxy having 1-7 carbon atoms, c is 0 or 1, X is $CH_2$ or —C(O)—, $Z^0$ is —COO—, —OCO—, —$CH_2CH_2$— or a single bond, and $R^0$ is alkyl, alkoxy, alkylcarbonyl, alkoxycarbonyl or alkylcarbonyloxy having 1-12 carbon atoms.

Examples of Compounds of Formula IV are
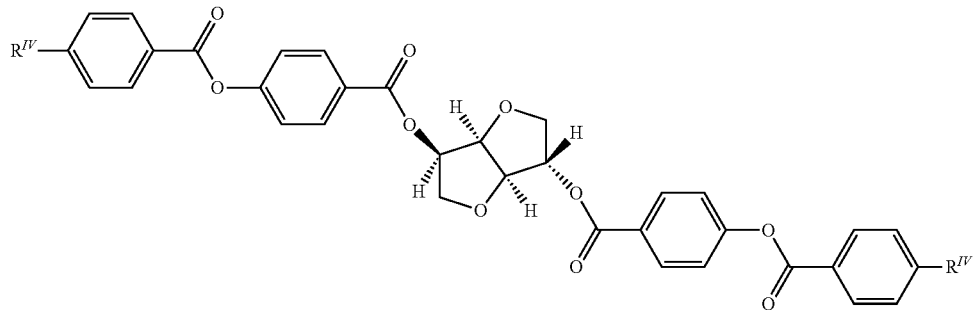
A-IV-1
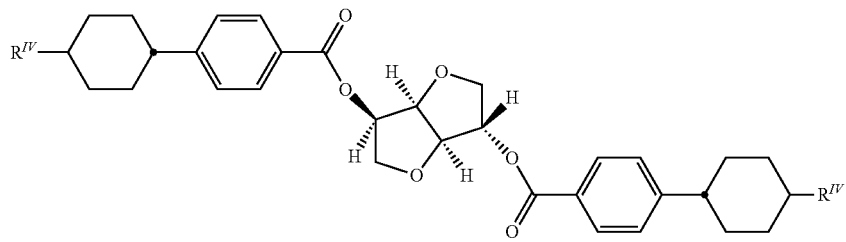
A-IV-2
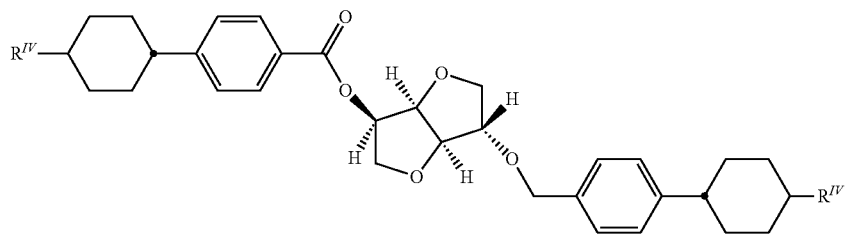
A-IV-3
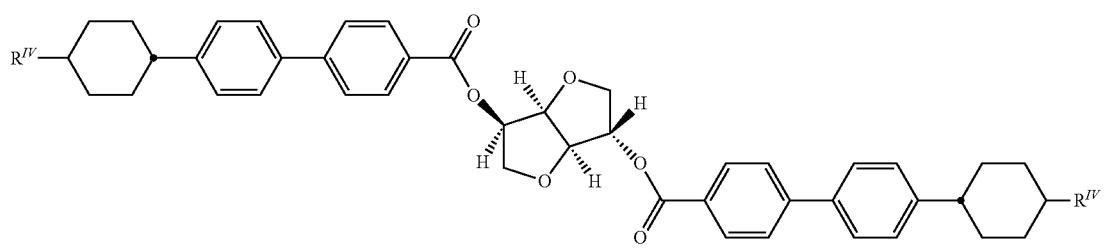
A-IV-4
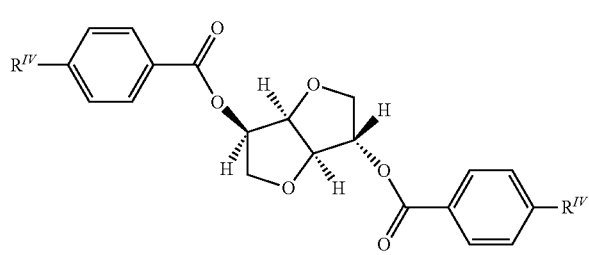
A-IV-5
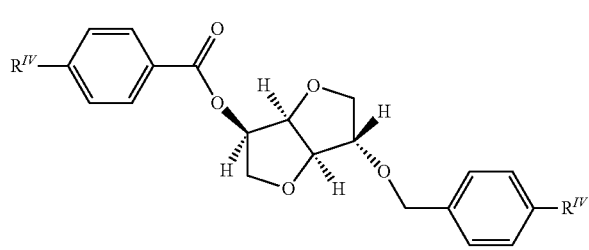
A-IV-6

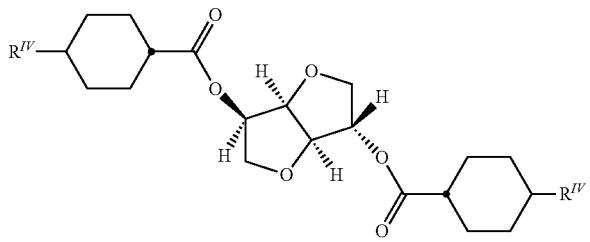

A-IV-7

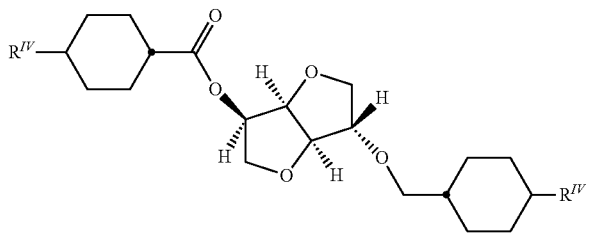

AIV-8

The compounds of the formula A-IV are described in WO 98/00428. The compounds of the formula A-V are described in GB-A-2,328,207.

Very particularly preferred dopants are chiral binaphthyl derivatives, as described in WO 02/94805, chiral binaphthol acetal derivatives, as described in WO 02/34739, chiral TADDOL derivatives, as described in WO 02/06265, and chiral dopants having at least one fluorinated bridging group and a terminal or central chiral group, as described in WO 02/06196 and WO 02/06195.

Particular preference is given to chiral compounds of the formula A-VI

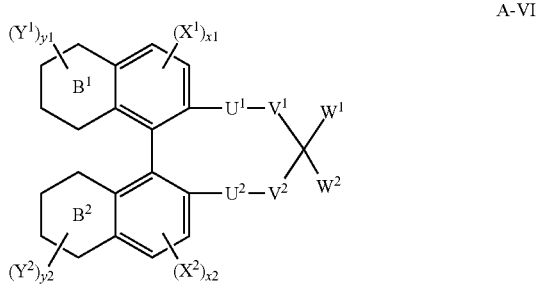

A-VI in which
$X^1$, $X^2$, $Y^1$ and $Y^2$ are each, independently of one another, F, Cl, Br, I, CN, SCN, SF$_5$, straight-chain or branched alkyl having from 1 to 25 carbon atoms, which is unsubstituted or monosubstituted or polysubstituted by F, Cl, Br, I or CN and in which, in addition, one or more non-adjacent CH$_2$ groups may each, independently of one another, be replaced by —O—, —S—, —NH—, NR$^x$—, —CO—, —COO—, —OCO—, —OCOO—, —S—CO—, —CO—S—, —CH=CH— or —C≡C— in such a way that O and/or S atoms are not bonded directly to one another, a polymerisable group or cycloalkyl or aryl having up to 20 carbon atoms, which may optionally be monosubstituted or polysubstituted by halogen, preferably F, or by a polymerisable group,
$x^1$ and $x^2$ are each, independently of one another, 0, 1 or 2,
$y^1$ and $y^2$ are each, independently of one another, 0, 1, 2, 3 or 4,
$B^1$ and $B^2$ are each, independently of one another, an aromatic or partially or fully saturated aliphatic six-membered ring in which one or more CH groups may each be replaced by N and one or more non-adjacent CH$_2$ groups may each be replaced by O or S,
$W^1$ and $W^2$ are each, independently of one another, —$Z^1$-$A^1$-($Z^2$-$A^2$)$_m$-R, and one of the two is alternatively $R^1$ or $A^3$, but both are not simultaneously H, or
$X_n^y$ is

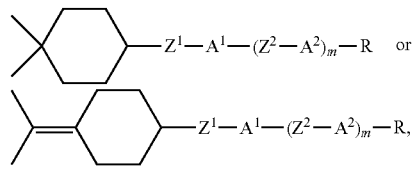

$U^1$ and $U^2$ are each, independently of one another, CH$_2$, O, S, CO or CS,
$V^1$ and $V^2$ are each, independently of one another, (CH$_2$)$_n$, in which from one to four non-adjacent CH$_2$ groups may each be replaced by O or S, and one of $V^1$ and $V^2$ and, in the case where $\chi^c$ is

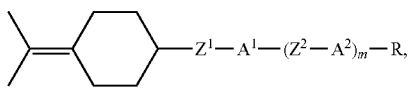

both are a single bond,
n is 1, 2 or 3
$Z^1$ and $Z^2$ are each, independently of one another, —O—, —S—, —CO—, —COO—, —OCO—, —O—COO—, —CO—NR$^x$—, —NR$^x$—CO—, —O—CH$_2$—, —CH$_2$—O—, —S—CH$_2$—, —CH$_2$—S—, —CF$_2$—O—, —O—CF$_2$—, —CF$_2$—S—, —S—CF$_2$—, —CH$_2$—CH$_2$—, —CF$_2$—CH$_2$—, —CH$_2$—CF$_2$—, —CF$_2$—CF$_2$—, —CH=N—, —N=CH—, —N=N—, —CH=CH—, —CF=CH—, —CH=CF—, —CF=CF—, —C≡C—, a combination of two of these groups, where no two O and/or S and/or N atoms are bonded directly to one another, preferably —CH=CH—COO—, or —COO—CH=CH—, or a single bond,
$R^x$ denotes alkyl having 1 to 6 C atoms,
$A^1$, $A^2$ and $A^3$ are each, independently of one another, 1,4-phenylene, in which one or two non-adjacent CH groups may each be replaced by N, 1,4-cyclohexylene, in which one or two non-adjacent CH$_2$ groups may each be replaced by O or S, 1,3-dioxolane-4,5-diyl, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where each of these groups may be monosubstituted or polysubstituted by L, and in addition $A^1$ can be a single bond,
L is a halogen atom, preferably F, CN, NO$_2$, alkyl, alkoxy, alkylcarbonyl, alkoxycarbonyl or alkoxycarbonyloxy having 1-7 carbon atoms, in which one or more H atoms may each be replaced by F or Cl,
m is in each case, independently, 0, 1, 2 or 3, and
R and $R^1$ are each, independently of one another, H, F, Cl, Br, I, CN, SCN, SF$_5$, straight-chain or branched alkyl having from 1 or 3 to 25 carbon atoms respectively, which may optionally be monosubstituted or polysubstituted by F, Cl, Br, I or CN, and in which one or more non-adjacent CH$_2$ groups may each be replaced by —O—, —S—, —NH—, —NR$^0$—, —CO—, —COO—, —OCO—, —O—COO—, —S—CO—, —CO—S—, —CH=CH— or —C≡C—, where no two O and/or S atoms are bonded directly to one another, or a polymerisable group.

Particular preference is given to chiral binaphthyl derivatives of the formula A-VI-1

A-VI-1

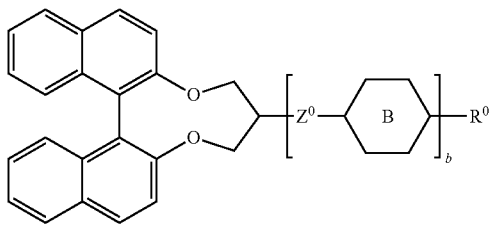

in which ring B, $R^0$ and $Z^0$ are as defined for the formulae A-IV and A-V, and b is 0, 1, or 2, in particular those selected from the following formulae A-VI-1a to A-VI-1c:

A-VI-1a

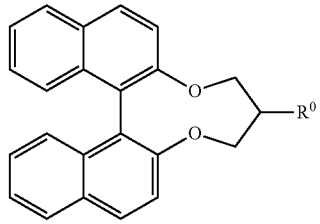

A-VI-1b

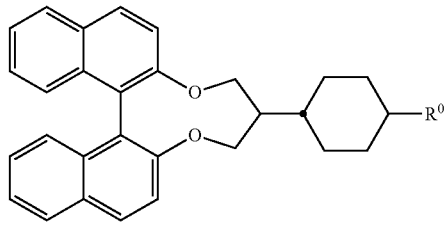

A-VI-1c

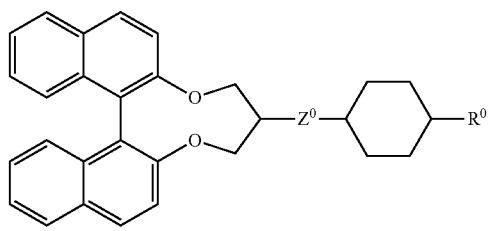

in which ring B, $R^0$, and $Z^0$ are as defined for the formula A-VI-1, and $R^0$ as defined for formula A-IV or H or alkyl having from 1 to 4 carbon atoms, and b is 0, 1 or 2, and $Z^0$ is, in particular, —OC(O)— or a single bond.

The concentration of the one or more chiral dopant(s), in the LC medium is preferably in the range from 0.001% to 20%, preferably from 0.05% to 5%, more preferably from 0.1% to 2%, and, most preferably from 0.5% to 1.5%. These preferred concentration ranges apply in particular to the chiral dopant S-4011 or R-4011 (both from Merck KGaA) and for chiral dopants having the same or a similar HTP. For Chiral dopants having either a higher or a lower absolute value of the HTP compared to S-4011 these preferred concentrations have to be decreased, respectively increased proportionally according to the ratio of their HTP values relatively to that of S-4011.

The pitch p of the LC media or host mixtures according to the invention is preferably in the range of from 5 to 50 μm, more preferably from 8 to 30 μm and particularly preferably from 10 to 20 μm.

Preferably, the media according to the invention, comprise a stabilizer selected from the group of compounds of the formulae ST-1 to ST-18.

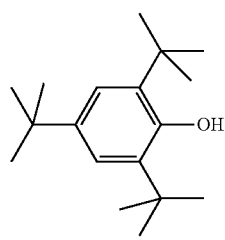
ST-1
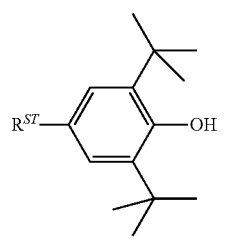
ST-2
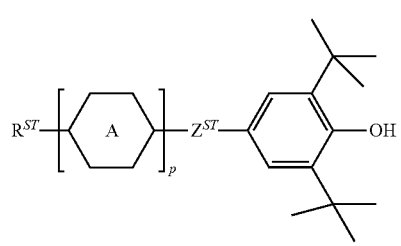
ST-3
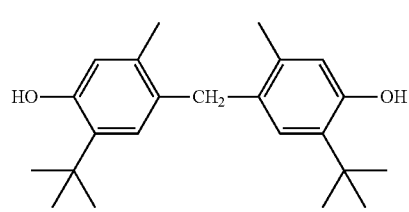
ST-4
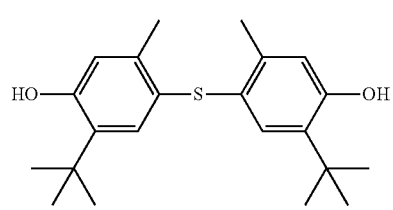
ST-5
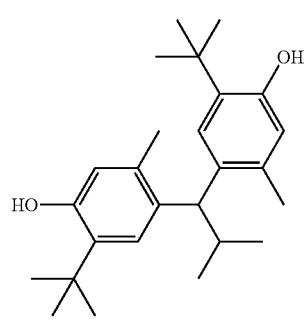
ST-6

ST-7
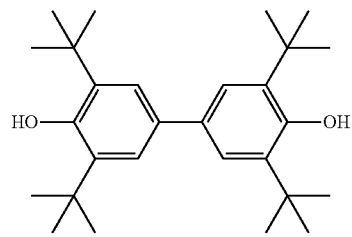
ST-8
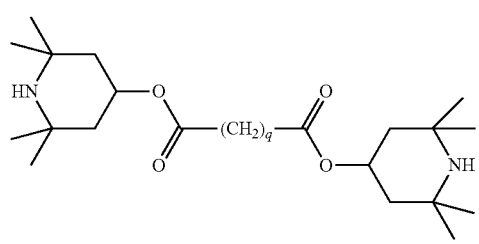
ST-9
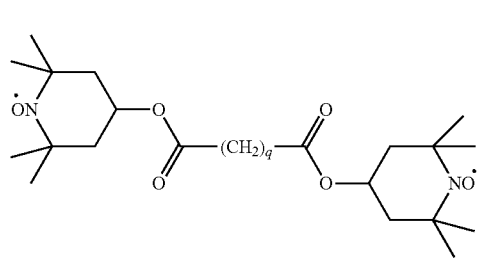
ST-10
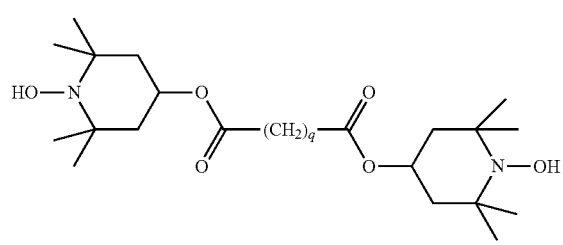
ST-11
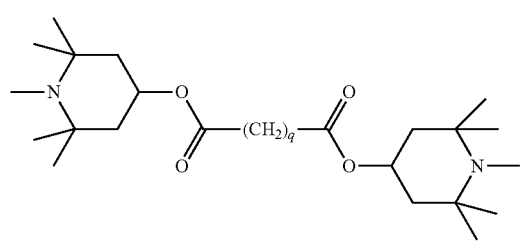

-continued
ST-12
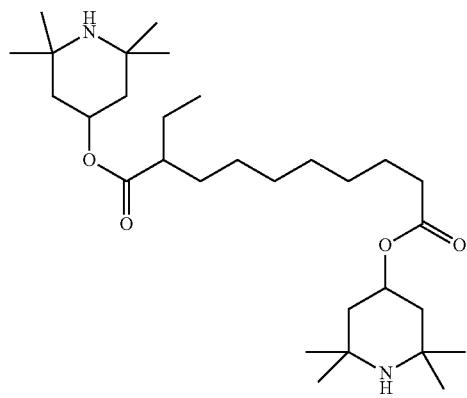
ST-13
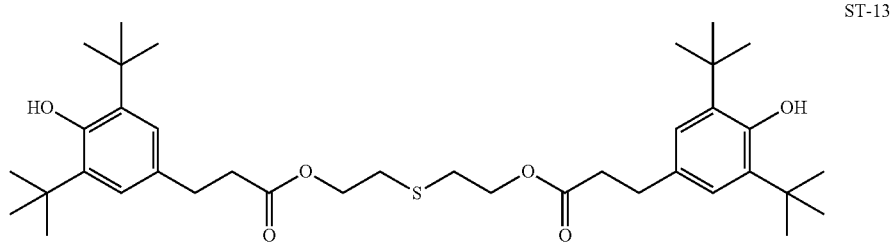
ST-14
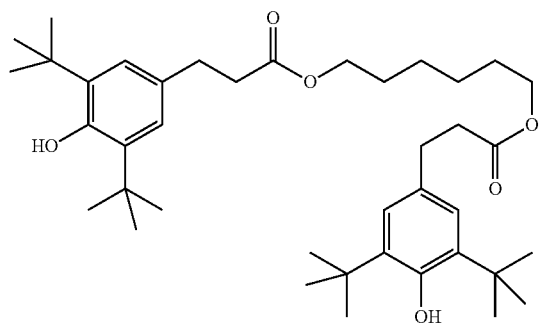
ST-15
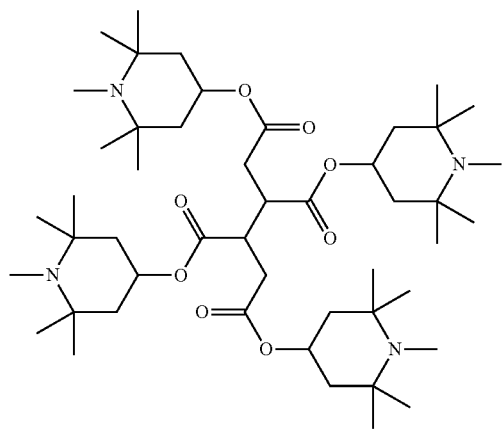

-continued

ST-16

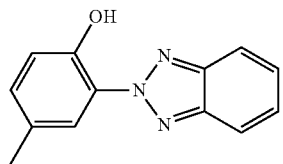

ST-17

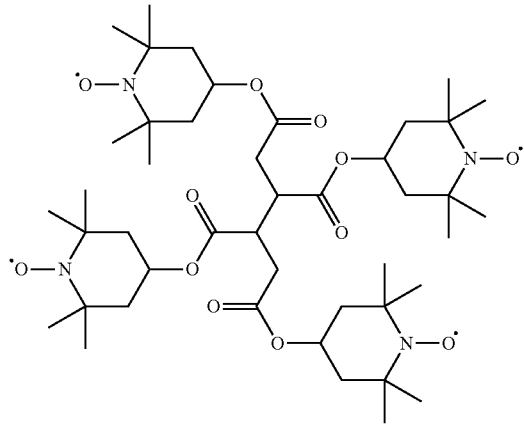

ST-18

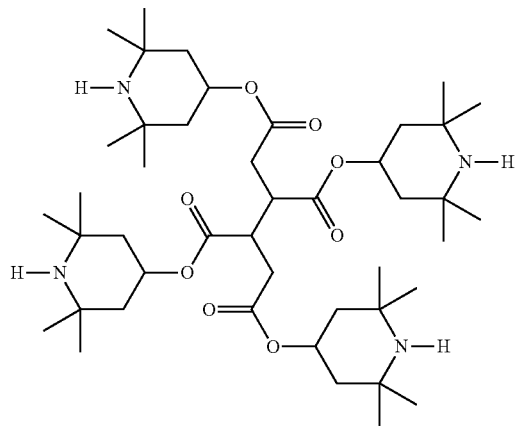

in which

R$^{ST}$ denotes H, an alkyl or alkoxy radical having 1 to 15 C atoms, where, in addition, one or more CH$_2$ groups in these radicals may each be replaced, independently of one another, by —C≡C—, —CF$_2$O—, —OCF$_2$—, —CH═CH—, —O—, —CO—O—, —O—CO— in such a way that O atoms are not linked directly to one another, and in which, in addition, one or more H atoms may be replaced by halogen,

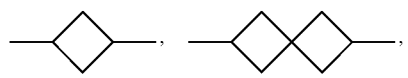

denotes

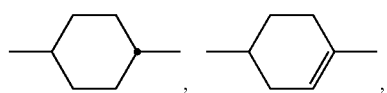

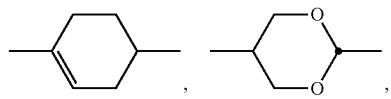

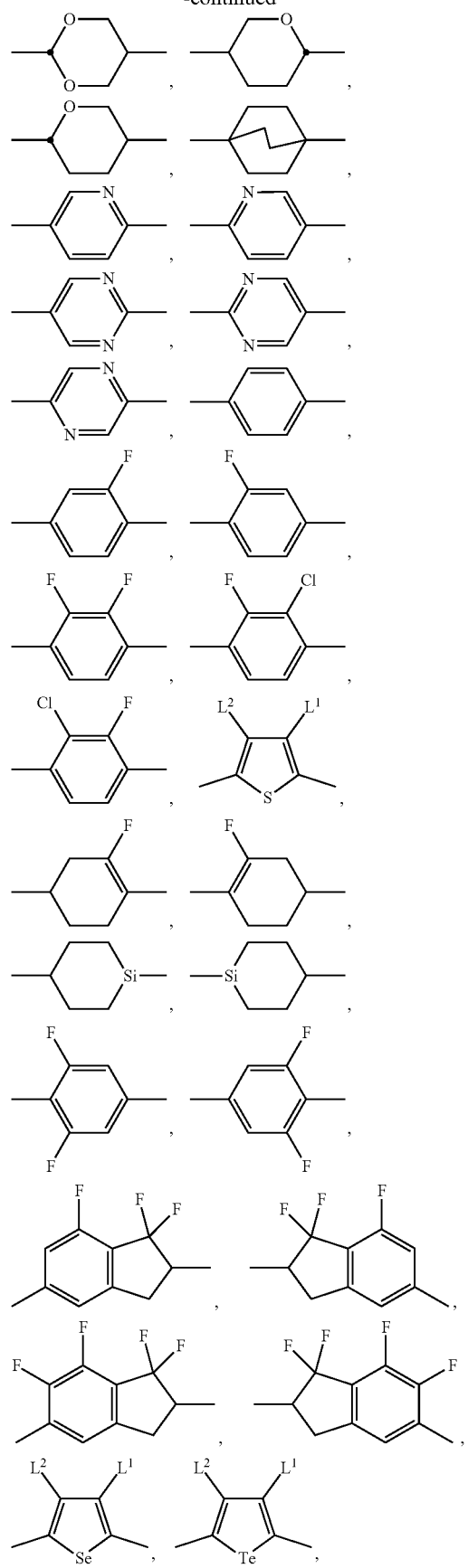
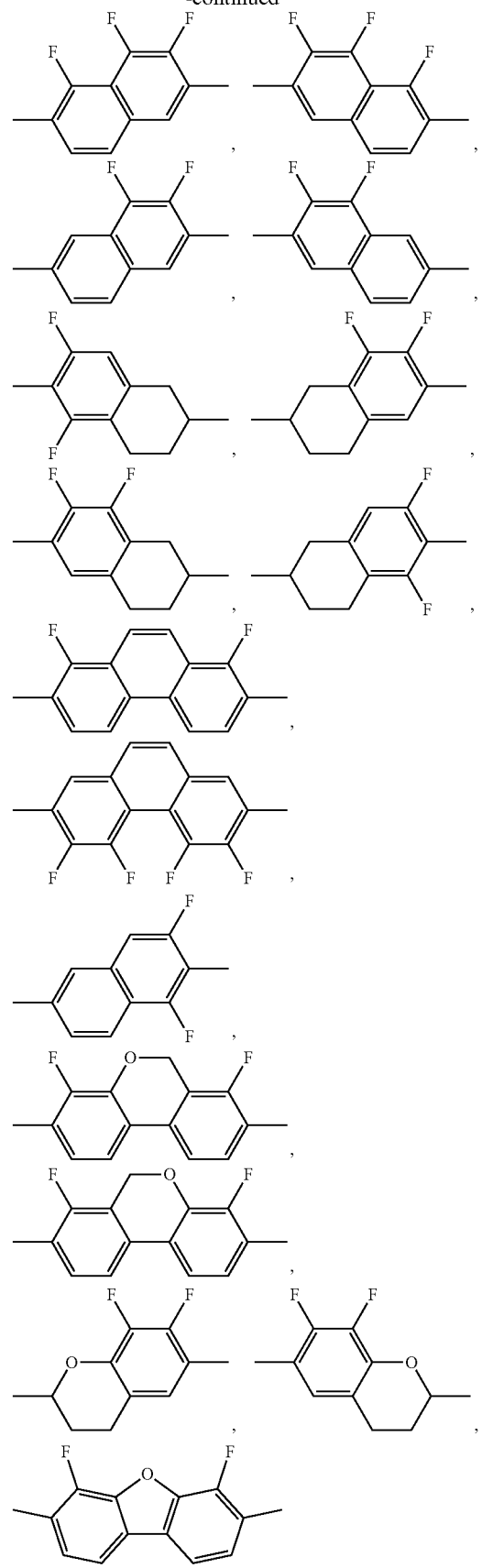

$Z^{ST}$ each, independently of one another, denote —CO—O—, —O—CO—, —CF$_2$O—, —OCF$_2$—, —CH$_2$O—, —OCH$_2$—, —CH$_2$—, —CH$_2$CH$_2$—, —(CH$_2$)$_4$—, —CH=CH—CH$_2$O—, —C$_2$F$_4$—, —CH$_2$CF$_2$—, —CF$_2$CH$_2$—, —CF=CF—, —CH=CF—, —CF=CH—, —CH=CH—, —C≡C— or a single bond, L$^1$ and L$^2$ each, independently of one another, denote F, Cl, CF$_3$ or CHF$_2$, p denotes 1 or 2, q denotes 1, 2, 3, 4, 5, 6, 7, 8, 9 or 10.

Of the compounds of the formula ST, special preference is given to the compounds of the formulae

ST-1

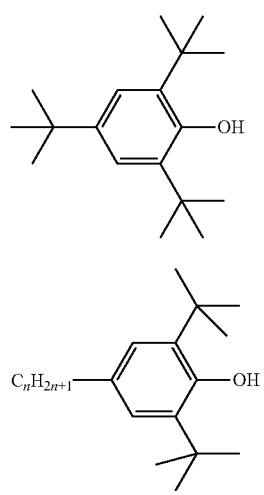

ST-2a

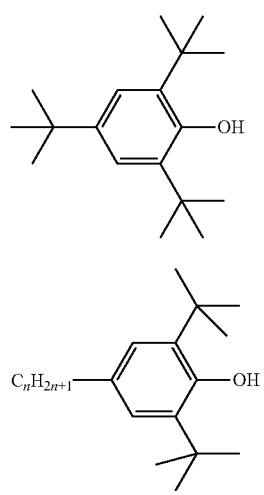

in which n=1, 2, 3, 4, 5, 6 or 7, preferably n=1 or 7

ST-3a

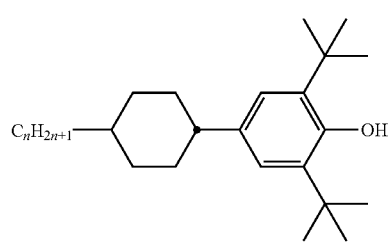

in which n=1, 2, 3, 4, 5, 6 or 7, preferably n=3

ST-3b

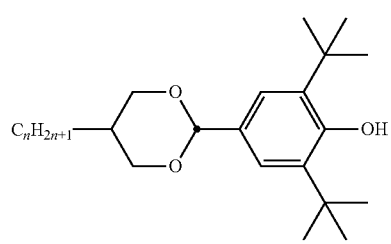

in which n=1, 2, 3, 4, 5, 6 or 7, preferably n=3

ST-8-1

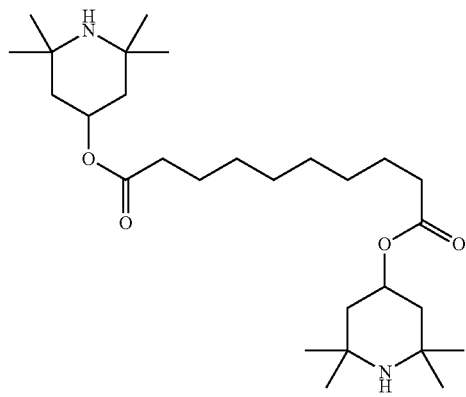

ST-9-1

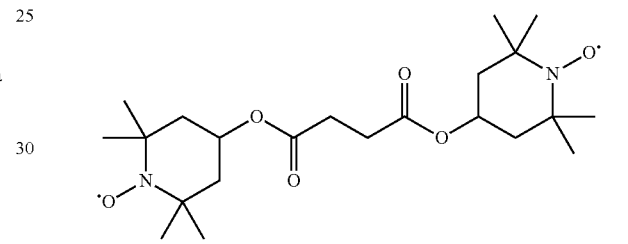

ST-12

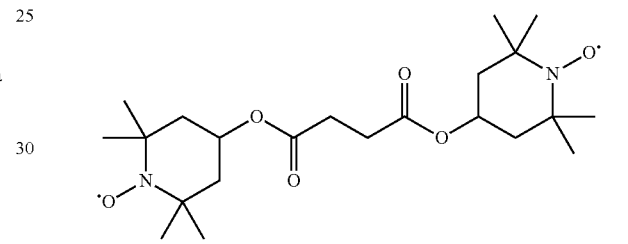

ST-16

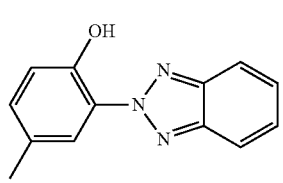

ST-17

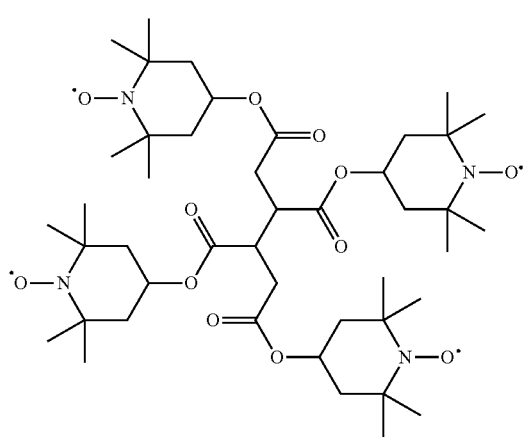

ST-18

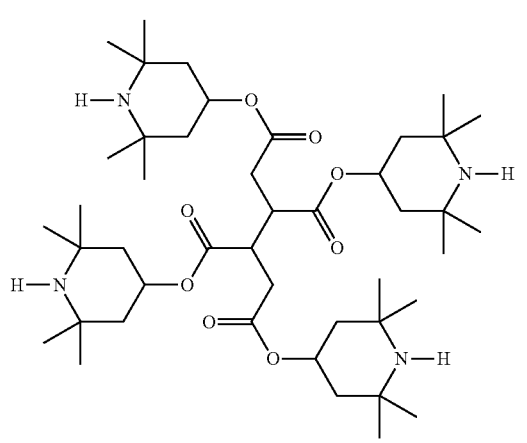

In the compounds of the formulae ST-3a and ST-3b, n preferably denotes 3. In the compounds of the formula ST-2a, n preferably denotes 7.

Very particularly preferred mixtures according to the invention comprise one or more stabilizers from the group of the compounds of the formulae ST-2a-1, ST-3a-1, ST-3b-1, ST-8-1, ST-9-1 and ST-12:

ST-2a-1

ST-3a-1

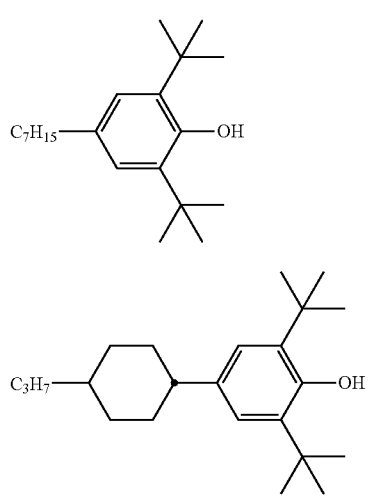

ST-3b-1

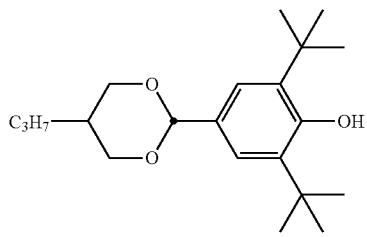

ST-8-1

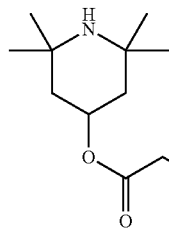

ST-9-1

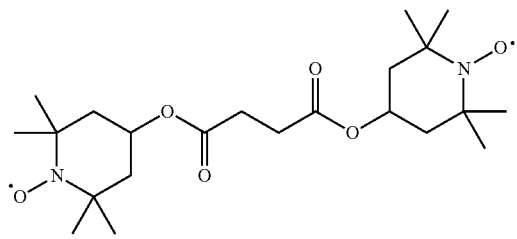

ST-12

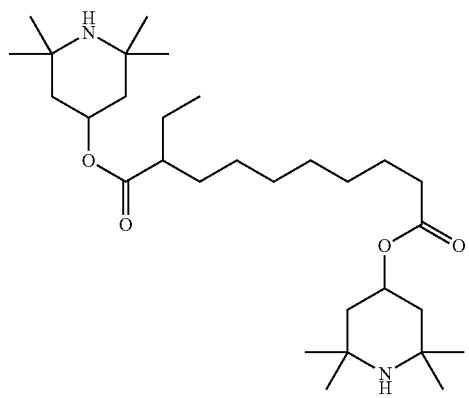

The compounds of the formulae ST-1 to ST-18 are preferably each present in the liquid-crystal mixtures according to the invention in amounts of 0.005-0.5%, based on the mixture.

If the mixtures according to the invention comprise two or more compounds from the group of the compounds of the formulae ST-1 to ST-18, the concentration correspondingly increases to 0.01-1% in the case of two compounds, based on the mixtures.

However, the total proportion of the compounds of the formulae ST-1 to ST-18, based on the mixture according to the invention, should not exceed 2%.

The compounds according to the present invention can be synthesized by or in analogy to known methods described in the literature (for example in the standard works such as Houben-Weyl, Methoden der Organischen Chemie [Methods of Organic Chemistry], Georg-Thieme-Verlag, Stuttgart), under reaction conditions which are known and suitable for said reactions. Use may also be made here of variants which are known per se, but are not mentioned here. In particular, they can be prepared as described in or in analogy to the following reaction schemes. Further methods for preparing the inventive compounds can be taken from the examples.

Other mesogenic compounds which are not explicitly mentioned above can optionally and advantageously also be used in the media in accordance with the present invention. Such compounds are known to the person skilled in the art.

In a preferred embodiment of the present invention, the total concentration of compounds of formula U in the liquid-crystalline medium is 1% or more, preferably 4% or more, very preferably 7% or more and particularly preferably 9% or more.

In a preferred embodiment of the present invention, the liquid-crystalline media preferably comprise in total 2% to 30%, preferably 5% to 25% and particularly preferably 10% to 20% of compounds of formula U.

In a preferred embodiment of the present invention, the liquid-crystalline media comprise in total 10% to 45%, preferably 15% to 40% and particularly preferably 20% to 35% of compounds of formula T, preferably selected from the formulae T-1a, T-2a and T-3a, very preferably from T-1a-5 and T-2a-4.

In a preferred embodiment of the present invention, the liquid-crystalline media comprise in total 15% to 35%, preferably 18% to 32% and particularly preferably 20% to 30% of compounds of formulae T-1a.

In a preferred embodiment, the medium comprises one or more compounds of formula I, preferably of formula I-2 over I-3, in a total concentration in the range of from 2% to 50%, more preferably from 5% to 30%, and particularly preferably from 10% to 25%.

In a preferred embodiment, the medium comprises one or more compounds of formula I-2, preferably of formula I-2c and/or I-2d in a total concentration in the range of from 1% to 30%, more preferably from 5% to 25%, and particularly preferably from 10% to 20%.

In a preferred embodiment, the medium comprises one or more compounds of formula I-3, preferably of formula I-3b and/or I-3d in a total concentration in the range of from 1% to 35%, more preferably from 10% to 30%, and particularly preferably from 15% to 25%.

In a preferred embodiment of the present invention the medium comprises one or more compounds of formula II, preferably of formula II-1, in a total concentration of 5% to 30%, more preferably 10% to 25%, particularly preferably 12% to 20%.

In a preferred embodiment of the present invention the medium comprises one or more compounds of formula IIA-1 in a total concentration of 5% to 25%, more preferably 8% to 20%, particularly preferably 10% to 15%.

In a preferred embodiment of the present invention the medium comprises one or more compounds of formula II-1 in an total concentration of 30% or less, more preferably 25% or less, particularly preferably 20% or less.

In a preferred embodiment of the present invention the medium comprises one or more compounds of formula III, preferably III-1 and/or III-2, more preferably III-1i and/or III-1b, in a total concentration of 15% to 70%, more preferably 25% to 60%, particularly preferably 35% to 50%.

Further preferred embodiments of the present invention, taken alone or in combination with one another, are as follows, wherein some compounds are abbreviated using the acronyms given in Table C below:

The medium comprises one, two, three, four or more compounds of formula III-1, preferably selected from the compounds of the formulae III-1b, III-1f and III-1i; more preferably of III-1b and III-1i;

The medium comprises a compound of formula III-1b, preferably in a total concentration in the range of from 2% to 30%, more preferably 5% to 25%, in particular 10% to 20%;

The medium comprises a compound of formula III-1 b in a total concentration of 10% or more;

The medium comprises a compound of formula III-1i, preferably in a total concentration in the range of from 10% to 40%, more preferably 15% to 38%, in particular 20% to 35%;

The medium comprises the compound PPU-TO-S and/or PPTU-TO-S and/or PTPU-TO-S and/or PP(1)-TO-S;

The medium comprises one or more compounds of formula U and one or more compounds of formula T, preferably in a total concentration in the range of from 25% to 55%, in particular of 30% to 50%;

The medium comprises one or more compounds of formula I-2d, preferably the compounds PGU-2-S and/or PGU-3-S and/or PGU-4-S;

The medium comprises one or more compounds of formula I-2d and formula II-1 b, preferably the compounds PGU-3-S and/or PGU-4-S and PTU-3-S and/or PTU-4-S and/or PTU-5-S;

The medium comprises one or more compounds of formula PPTU-n-S and/or PTPU-n-S in an total concentration in the range of from 10 to 20%;

The medium comprises one or more compounds of formula PPTU-n-S and/or PTPU-n-S and/or PGTU-n-S in a total concentration in the range of from 15 to 30%, where n is 2, 3, 4, 5 or 6;

The medium comprises a compound of formula CPTU-n-S and PPTU-n-S, where n is 2, 3, 4, 5 or 6;

The medium comprises a compound of formula XII-3, preferably of the formula CPU(F,F)-n-S where n is 2, 3, 4 or 5;

The medium comprises one or more compounds of formula ST-3, preferably ST-3a and/or ST-3b, particularly preferably ST-3b-1, in a total concentration in the range of from 0.01 to 1%, preferably from 0.05 to 0.5%, particularly from 0.10 to 0.15%.

The liquid-crystal media in accordance with the present invention preferably have a clearing point of 90° C. or more, more preferably 100° C. or more, more preferably 110° C. or more, more preferably 120° C. or more, more preferably 130° C. or more, particularly preferably 140° C. or more and very particularly preferably 150° C. or more.

The liquid-crystal media in accordance with the present invention preferably have a clearing point of 160° C. or less, more preferably 140° C. or less, particularly preferably 120° C. or less, and very particularly preferably 100° C. or less.

The nematic phase of the media according to the invention preferably extends at least from 0° C. or less to 90° C. or more. It is advantageous for the media according to the invention to exhibit even broader nematic phase ranges, preferably at least from −10° C. or less to 120° C. or more, very preferably at least from −20° C. or less to 140° C. or more and in particular at least from −30° C. or less to 150° C. or more, very particularly preferably at least from −40° C. or less to 170° C. or more.

The $\Delta\varepsilon$ of the liquid-crystal medium according to the present invention, at 1 kHz and 20° C., is preferably 1 or more, more preferably 2 or more and very preferably 3 or more.

The birefringence ($\Delta n$) of the liquid-crystal media according to the present invention, at 589 nm ($Na^D$) and 20° C., is preferably 0.280 or more, more preferably 0.300 or more, even more preferably 0.320 or more, very preferably 0.330 or more and in particular 0.350 or more.

The $\Delta n$ of the liquid-crystal media according to the present invention, at 589 nm ($Na^D$) and 20° C., is preferably in the range from 0.200 to 0.900, more preferably in the range from 0.250 to 0.800, even more preferably in the range from 0.300 to 0.700 and very particularly preferably in the range from 0.350 to 0.600.

In a preferred embodiment of the present application, the $\Delta n$ of the liquid-crystal media in accordance with the present invention is preferably 0.50 or more, more preferably 0.55 or more.

The compounds of the formulae I to III in each case include dielectrically positive compounds having a dielectric anisotropy of greater than 3, dielectrically neutral compounds having a dielectric anisotropy of less than 3 and greater than −1.5 and dielectrically negative compounds having a dielectric anisotropy of −1.5 or less.

The compounds of the formulae I, II and III are preferably dielectrically positive.

In the present application, the expression dielectrically positive describes compounds or components where $\Delta\varepsilon > 3.0$, dielectrically neutral describes those where $-1.5 \leq \Delta\varepsilon \leq 3.0$ and dielectrically negative describes those where $\Delta\varepsilon < -1.5$. $\Delta\varepsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 µm. The voltage applied is a rectangular wave having a frequency of 1 kHz and an effective value of typically 0.5 V to 1.0 V, but it is always selected to be below the capacitive threshold of the respective test mixture.

$\Delta\varepsilon$ is defined as $(\varepsilon_{\parallel} - \varepsilon_{\perp})$, while $\varepsilon_{ave.}$ is $(\varepsilon_{\parallel} + 2\varepsilon_{\perp})/3$.

The host mixture used for the determination of physical constants of pure compounds by extrapolation is ZLI-4792 from Merck KGaA, Germany. The absolute values of the dielectric constants, the birefringence ($\Delta n$) and the rotational viscosity ($\gamma_1$) of the compounds are determined from the change in the respective values of the host mixture on addition of the compounds. The concentration in the host is 10% or in case of insufficient solubility 5%. The values are extrapolated to a concentration of 100% of the added compounds.

In the examples, the phase sequences of pure compounds are given using the following abbreviations:

Tg: glass transition, K: crystalline, N: nematic, SmA: smectic A, SmB: smectic B, I: isotropic.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status Nov. 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\varepsilon$) is determined at a frequency of 1 kHz. The threshold voltages, as well as all other electro-optical properties, are determined using test cells produced at Merck KGaA, Germany. The test cells for the determination of $\Delta\varepsilon$ have a cell thickness of approximately 20 µm. The electrode is a circular ITO electrode having an area of 1.13 cm$^2$ and a guard ring. The orientation layers are SE-1211 from Nissan Chemicals, Japan, for homeotropic orientation ($\varepsilon_{\parallel}$) and polyimide AL-1054 from Japan Synthetic Rubber, Japan, for homogeneous orientation ($\varepsilon_{\perp}$). The capacitances are determined using a Solatron 1260 frequency response analyzer using a sine wave with a voltage of 0.3 $V_{rms}$. The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency range as described in A. Penirschke et al. "Cavity Perturbation Method for Characterization of Liquid Crystals up to 35 GHz", 34th European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an inner diameter of 0.5 mm and an outer diameter of 0.78 mm. The effective length is 2.0 cm. The filled capillary is introduced into the center of the cylindrical cavity with a resonance frequency of 19 GHz. This cavity has a length of 11.5 mm and a radius of 6 mm. The input signal (source) is then applied, and the frequency depending response of the cavity is recorded using a commercial vector network analyzer (N5227A PNA Microwave Network Analyzer, Keysight Technologies Inc. USA. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

All mixtures according to the invention are nematic. The liquid-crystal media according to the invention preferably have nematic phases in preferred ranges given above. The expression have a nematic phase here means on the one hand that no smectic phase and no crystallization are observed at low temperatures at the corresponding temperature and on the other hand that no clearing occurs on heating from the nematic phase. At high temperatures, the clearing point is measured in capillaries by conventional methods. The investigation at low temperatures is carried out in a flow viscometer at the corresponding temperature and checked by storage of bulk samples: The storage stability in the bulk (LTS) of the media according to the invention at a given temperature T is determined by visual inspection. 2 g of the media of interest are filled into a closed glass vessel (bottle) of appropriate size placed in a refrigerator at a predetermined temperature. The bottles are checked at defined time intervals for the occurrence of smectic phases or crystallization. For every material and at each temperature two bottles are stored. If crystallization or the appearance of a smectic phase is observed in at least one of the two correspondent bottles the test is terminated and the time of the last inspection before the one at which the occurrence of a higher ordered phase is observed is recorded as the respective storage stability. The test is finally terminated after 1000 h, i.e an LTS value of 1000 h means that the mixture is stable at the given temperature for at least 1000 h.

The liquid crystals employed preferably have a positive dielectric anisotropy. This is preferably 2 or more, preferably 4 or more, particularly preferably 6 or more and very particularly preferably 10 or more.

Furthermore, the liquid-crystal media according to the invention are characterized by high anisotropy values in the microwave range. The birefringence at about 19 GHz is, for example, preferably 0.14 or more, particularly preferably 0.15 or more, particularly preferably 0.20 or more, particularly preferably 0.25 or more and very particularly preferably 0.30 or more. In addition, the birefringence is preferably 0.80 or less.

Above and below:

$V_o$ denotes threshold voltage, capacitive [V] at 20° C.,
$n_e$ denotes extraordinary refractive index at 20° C. and 589 nm,
$n_o$ denotes ordinary refractive index at 20° C. and 589 nm,
$\Delta n$ denotes optical anisotropy at 20° C. and 589 nm,
$\varepsilon_\perp$ denotes dielectric permittivity perpendicular to the director at 20° C. and 1 kHz,
$\varepsilon_\parallel$ denotes dielectric permittivity parallel to the director at 20° C. and 1 kHz,
$\Delta\varepsilon$ denotes dielectric anisotropy at 20° C. and 1 kHz,
cl.p., T(N,I) denotes clearing point [° C.],
$\gamma_1$ denotes rotational viscosity measured at 20° C. [mPa·s],
$K_1$ denotes elastic constant, "splay" deformation at 20° C. [pN],
$K_2$ denotes elastic constant, "twist" deformation at 20° C. [pN],
$K_3$ denotes elastic constant, "bend" deformation at 20° C. [pN],
$K_{avg.}$ denotes the average elastic constant defined as $K_{avg.}=\frac{1}{3}(1.5K_1+K_3)$ at 20° C. [pN], and
LTS denotes low-temperature stability (nematic phase), determined in test cells or in the bulk, as specified.

The dielectric anisotropy in the microwave range is defined as $$\Delta\varepsilon_r \equiv (\varepsilon_{r,\parallel}-\varepsilon_{r,\perp})$$

The tunability ($\tau$) is defined as $$\tau \equiv (\Delta\varepsilon_r/\varepsilon_{r,\parallel})$$

The material quality ($\eta$) is defined as $$\eta \equiv (\tau/\tan\delta_{\varepsilon r,max}), \text{ where}$$

the maximum dielectric loss is $$\tan\delta_{\varepsilon r,max} \equiv \max \cdot \{\tan\delta_{\varepsilon r,\perp}; \tan\delta_{\varepsilon r,\parallel}\}.$$

The tunability $\tau$ of the medium according to the invention, measured at 20° C. and 19 GHz is 0.250 or more, preferably 0.300 or more, 0.310 or more, 0.320 or more, 0.330 or more, or 0.340 or more, very preferably 0.345 or more and in particular 0.350 or more.

The material quality ($\eta$) of the preferred liquid-crystal materials is 6 or more, preferably 8 or more, preferably 10 or more, preferably 15 or more, preferably 17 or more, preferably 20 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, liquid crystals having a negative value of the dielectric anisotropy can also advantageously be used.

The liquid crystals employed are either individual substances or mixtures. They preferably have a nematic phase.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

Preferably the media according to the present invention comprise one or more chiral compounds as chiral dopants in order to adjust their cholesteric pitch. Their total concentration in the media according to the instant invention is preferably in the range 0.05% to 15%, more preferably from 1% to 10% and most preferably from 2% to 6%.

Optionally the media according to the present invention may comprise further liquid crystal compounds in order to adjust the physical properties. Such compounds are known to the expert. Their concentration in the media according to the instant invention is preferably 0% to 30%, more preferably 0.1% to 20% and most preferably 1% to 15%.

The response times are given as rise time ($\tau_{on}$) for the time for the change of the relative tuning, respectively of the relative contrast for the electro-optical response, from 0% to 90% ($t_{90}-t_0$), i.e. including the delay time ($t_{10}-t_0$), as decay time ($\tau_{off}$) for the time for the change of the relative tuning, respectively of the relative contrast for the electro-optical response, from 100% back to 10% ($t_{100}-t_{10}$) and as the total response time ($\tau_{total}=\tau_{on}+\tau_{off}$), respectively.

The liquid-crystal media according to the invention consist of a plurality of compounds, preferably 3 to 30, more preferably 4 to 20 and very preferably 4 to 16 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to D below. All radicals $C_nH_{2n+1}$, $C_mH_{2m+1}$, and $C_lH_{2l+1}$ or $C_nH_{2n-1}$, $C_mH_{2m-1}$ and $C_lH_{2l-1}$ denote straight-chain alkyl or alkenyl, preferably 1-E-alkenyl, respectively, in each case having n, m or l C atoms. Table A lists the codes used for the ring elements of the core structures of the compounds, while Table B shows the linking groups. Table C gives the meanings of the codes for the left-hand or right-hand end groups. Table D shows illustrative structures of compounds with their respective abbreviations.

TABLE A

| Ring elements | | | |
| --- | --- | --- | --- |
| C | (cyclohexane) | | |
| D | (1,3-dioxane) | DI | (1,3-dioxane) |
| A | (tetrahydropyran) | AI | (tetrahydropyran) |
| G | (difluorobenzene) | GI | (difluorobenzene) |
| U | (difluorobenzene) | UI | (difluorobenzene) |
| U(F,F) | (tetrafluorobenzene) | | |
| Y | (difluorobenzene) | | |
| M | (pyrimidine) | MI | (pyrimidine) |
| N | (pyridine) | NI | (pyridine) |
| Np | (naphthalene) | | |
| N3f | (fluoronaphthalene) | N3fI | (fluoronaphthalene) |
| tH | (tetrahydronaphthalene) | tHI | (tetrahydronaphthalene) |
| tH2f | (difluorotetrahydronaphthalene) | tH2fI | (difluorotetrahydronaphthalene) |
| dH | (decahydronaphthalene) | | |
| K | (difluoroindane) | KI | (difluoroindane) |

TABLE A-continued
Ring elements
| | | | |
|---|---|---|---|
| L | | LI | |
| F | | FI | |
| P | | P(n,m) | |
| P(o) | | PI(o) | |
| P(i3) | | PI(ic3) | |
| P(t4) | | PI(t4) | |
| P(c3) | | PI(c3) | |
| P(c4) | | PI(c4) | |
| P(c5) | | PI(c5) | |
| P(e5) | | PI(e5) | |
| P(c6) | | PI(c6) | |
| P(e6) | | PI(e6) | |
| GI(o) | | G(o) | |
| | in which o = 1, 2, 3, 4, 5 or 6 | | in which o = 1, 2, 3, 4, 5 or 6 |
| GI(i3) | | G(i3) | |
| GI(t4) | 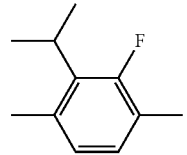 | G(t4) | |
| GI(c3) | 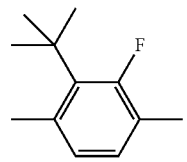 | G(c3) | |
| GI(c4) | 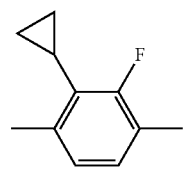 | G(c4) | 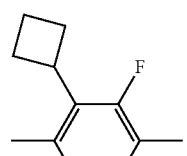 |

TABLE A-continued

Ring elements

GI(c5), G(c5), GI(e5), G(e5), GI(c6), G(c6), GI(e6), G(e6), Np(1,4), Th

TABLE B

Linking groups

| | | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CFCF$_2$— | | |

TABLE B

End groups

| Left-hand side | | Right-hand side | |
|---|---|---|---|
| Used alone | | | |
| -n- | C$_n$H$_{2n+1}$— | -n | —C$_n$H$_{2n+1}$ |
| -nO— | C$_n$H$_{2n+1}$—O— | —On | —O—C$_n$H$_{2n+1}$ |
| —V— | CH$_2$=CH— | —V | —CH=CH$_2$ |
| -nV— | C$_n$H$_{2n+1}$—CH=CH— | -nV | —C$_n$H$_{2n}$—CH=CH$_2$ |
| —Vn- | CH$_2$=CH—C$_n$H$_{2n+1}$— | —Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| —N | N≡C— | —N | —C≡N |
| —S— | S=C=N— | —S | —N=C=S |
| —F— | F— | —F | —F |
| —CL— | Cl— | —CL | —Cl |
| —M— | CFH$_2$— | —M | —CFH$_2$ |
| —D— | CF$_2$H— | —D | —CF$_2$H |
| —T— | CF$_3$— | —T | —CF$_3$ |
| —MO— | CFH$_2$O— | —OM | —OCFH$_2$ |
| —DO— | CF$_2$HO— | —OD | —OCF$_2$H |
| —TO— | CF$_3$O— | —OT | —OCF$_3$ |
| —FXO— | CF$_2$=CH—O— | —OXF | —O—CH=CF$_2$ |
| —A— | H—C≡C— | —A | —C≡C—H |
| -nA— | C$_n$H$_{2n+1}$—C≡C— | —An | —C≡C—C$_n$H$_{2n+1}$ |
| —NA— | N≡C—C≡C— | —AN | —C≡C—C≡N |
| -(cn)- | (CH$_2$)$_{n-2}$ | -(cn) | (CH$_2$)$_{n-2}$ |
| -(cn)m- | (CH$_2$)$_{n-2}$ (CH$_2$)$_m$— | -m(cn) | —(CH$_2$)$_m$ (CH$_2$)$_{n-2}$ |
| Used in combination with others | | | |
| -...A...- | —C≡C— | -...A... | —C≡C— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |

TABLE B-continued

| End groups | | | |
|---|---|---|---|
| Left-hand side | | Right-hand side | |
| -...K...- | —CO— | -...K... | —CO— |
| -...W...- | —CF=CF— | -...W... | —CF=CF— | in which n and m each denote integers, and the three dots "..." are placeholders for other abbreviations from this table.

The following table shows illustrative structures together with their respective abbreviations. These are shown in order to illustrate the meaning of the rules for the abbreviations. They furthermore represent compounds which are preferably used.

TABLE C

Illustrative structures

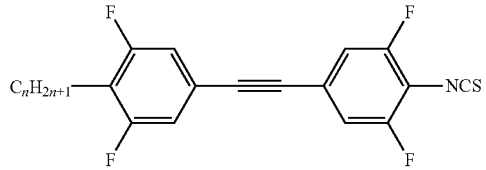

UITU-n-S

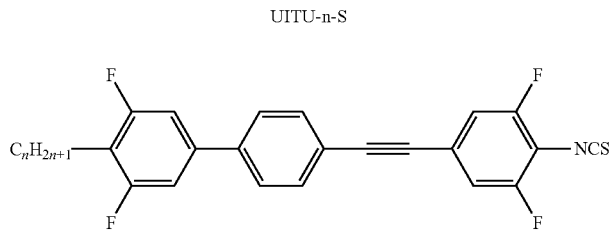

UIPTU-n-S

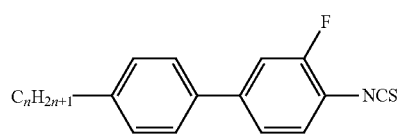

PG-n-S

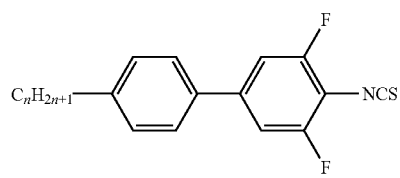

PU-n-S

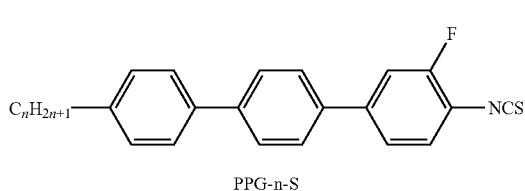

PPG-n-S

TABLE C-continued
Illustrative structures
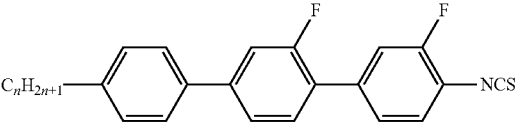
PGG-n-S
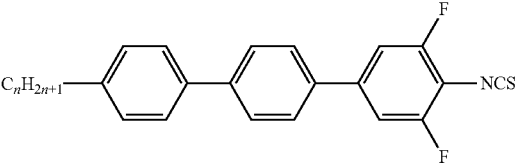
PPU-n-S
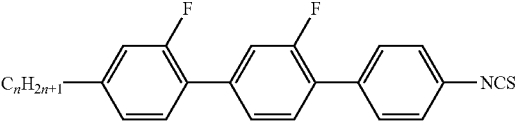
GGP-n-S
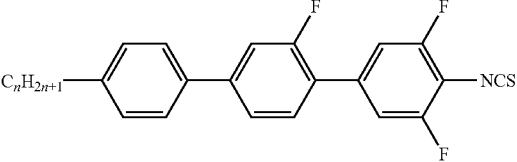
PGU-n-S
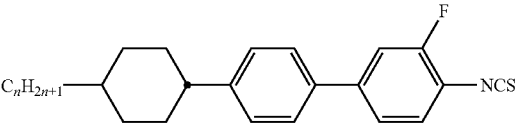
CPG-n-S
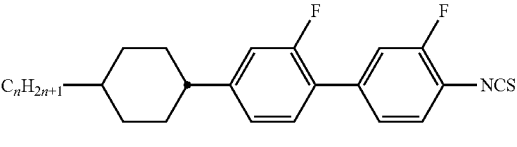
CGG-n-S
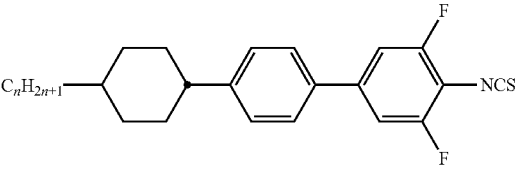
CPU-n-S
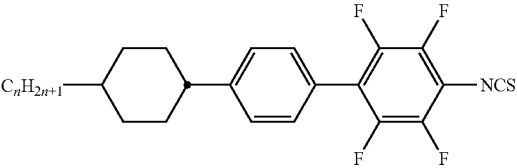
CPU(F,F)-n-S TABLE C-continued
Illustrative structures
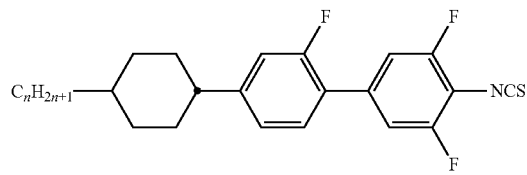
CGU-n-S
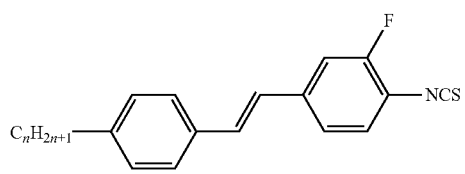
PVG-n-S
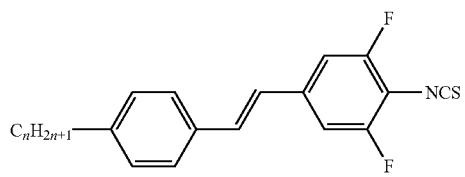
PVU-n-S
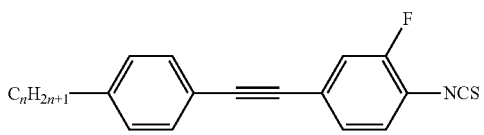
PTG-n-S
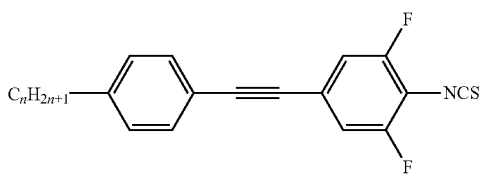
PTU-n-S
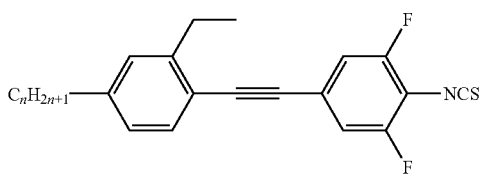
P(2)TU-n-S
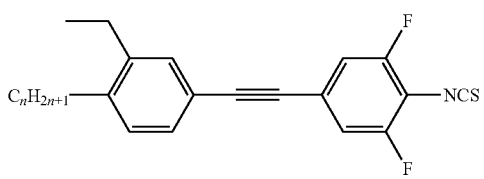
PI(2)TU-n-S TABLE C-continued
Illustrative structures
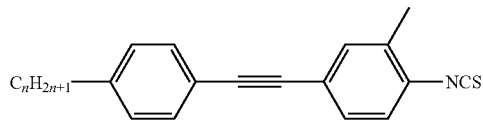
PTP(1)-n-S
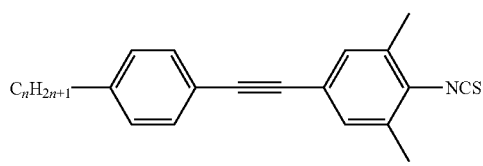
PTP(1,1)-n-S
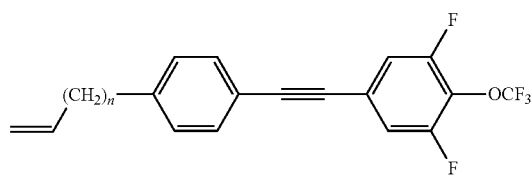
PTU-Vn-OT
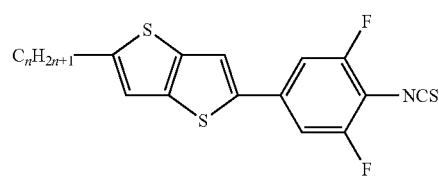
ThU-n-S
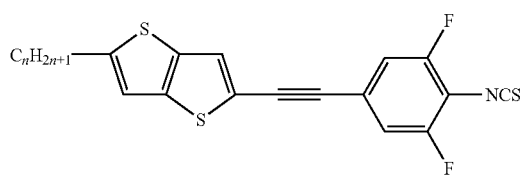
ThTU-n-S
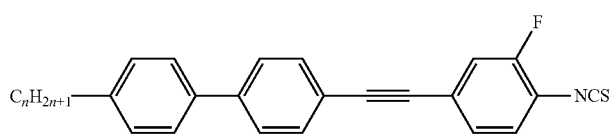
PPTG-n-S
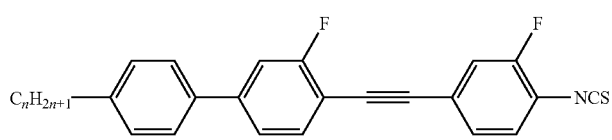
PGTG-n-S TABLE C-continued
Illustrative structures
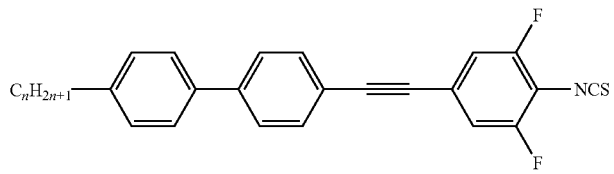
PPTU-n-S
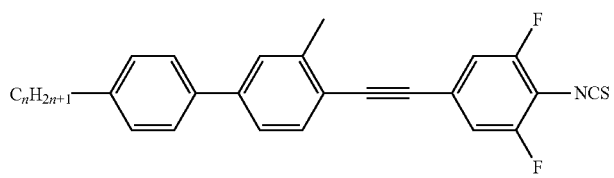
PP(1)TU-n-S
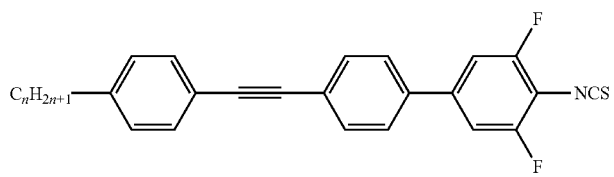
PTPU-n-S
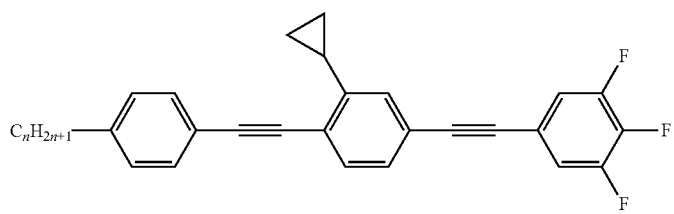
PTPI(c3)TU-n-F
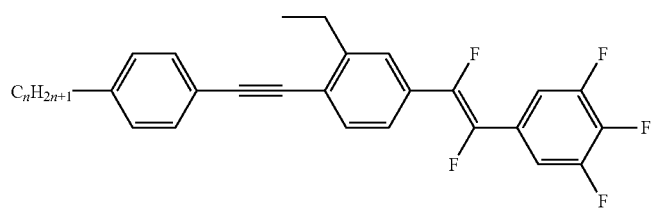
PTPI(2)WU-n-F
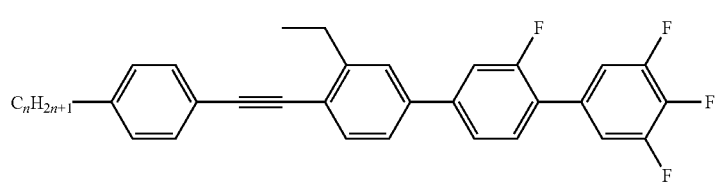
PTPI(2)GU-n-F TABLE C-continued
Illustrative structures
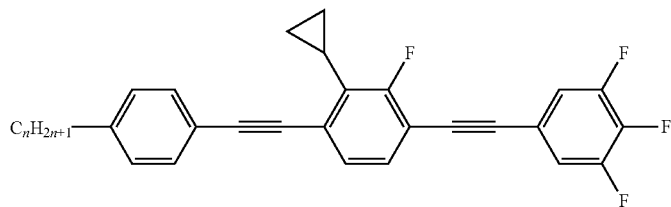
PTG(c3)TU-n-F
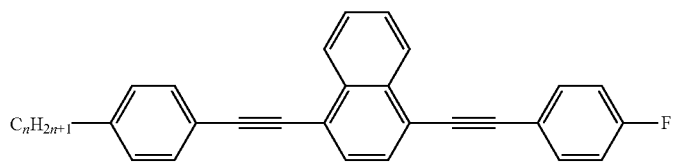
PTN(1,4)TP-n-F
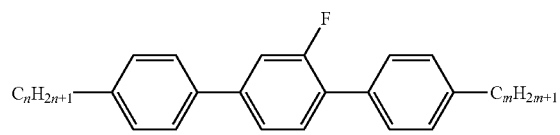
PGP-n-m
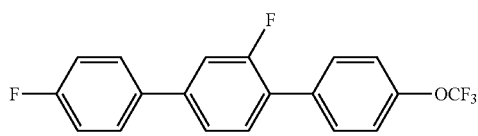 [SMILES: Fc1ccc(-c2ccc(-c3ccc(OC(F)(F)F)cc3)c(F)c2)cc1]
PGP-F-OT
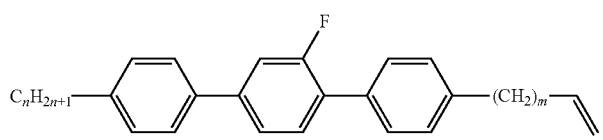
PGP-n-mV
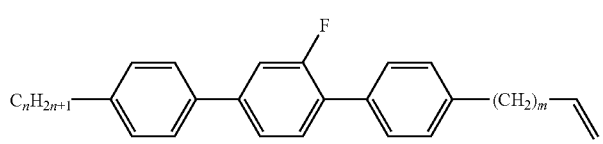
PGP-n-mVI
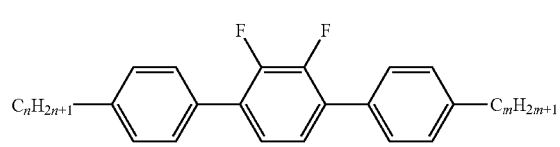
PYP-n-m
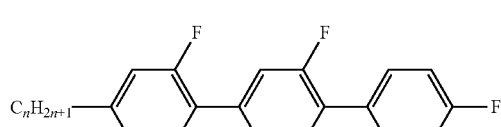
GGP-n-F TABLE C-continued
Illustrative structures
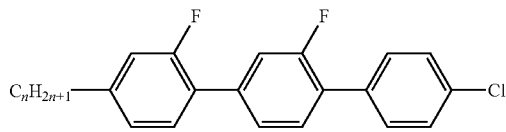
GGP-n-CL
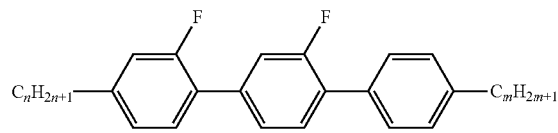
GGP-n-m
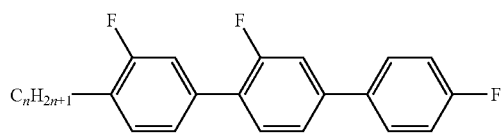
PGIGI-n-F
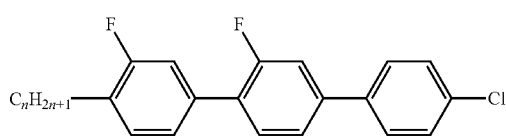
PGIGI-n-CL
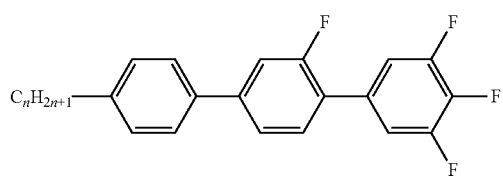
PGU-n-F
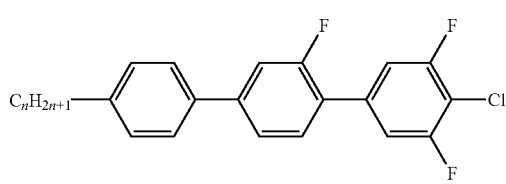
PGU-n-CL
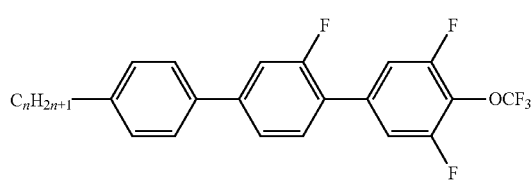
PGU-n-OT
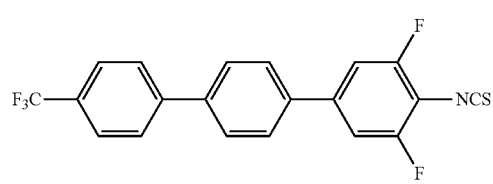
PPU-T-S TABLE C-continued
Illustrative structures
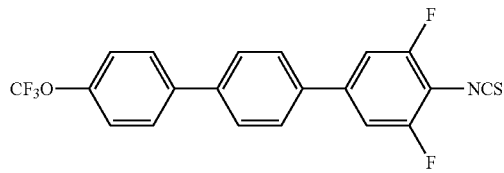
PPU-TO-S
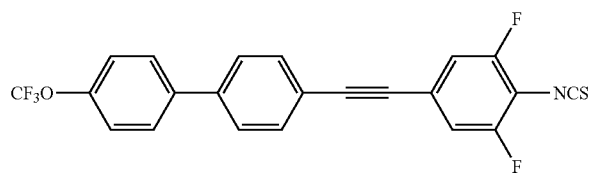
PPTU-TO-S
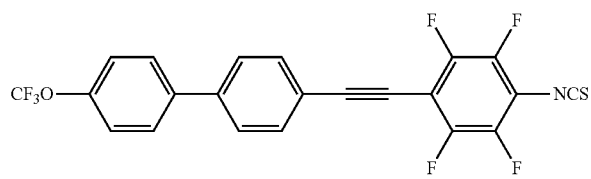
PPTU(F,F)-TO-S
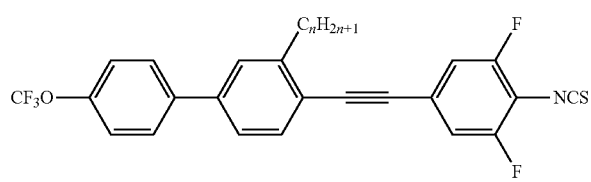
PP(n)TU-TO-S
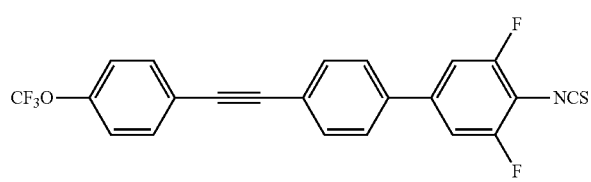
PTPU-TO-S
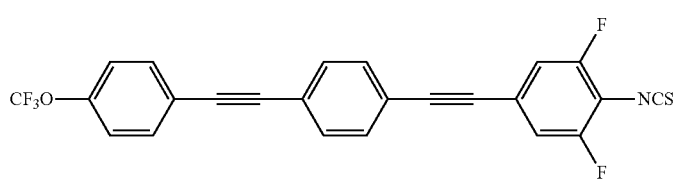
PTPTU-TO-S
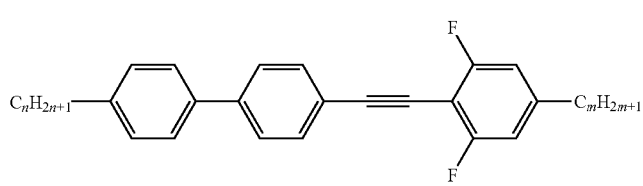
PPTUI-n-m TABLE C-continued
Illustrative structures
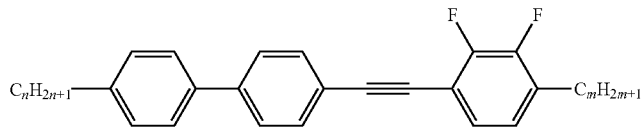
PPTY-n-m
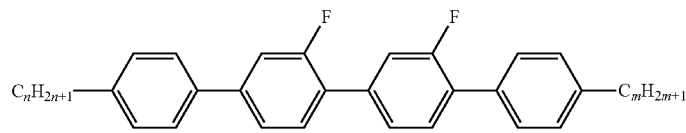
PGGP-n-m
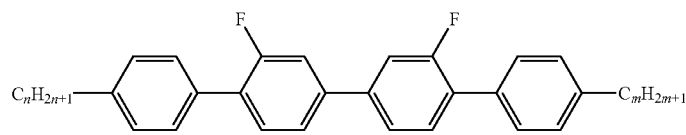
PGIGP-n-m
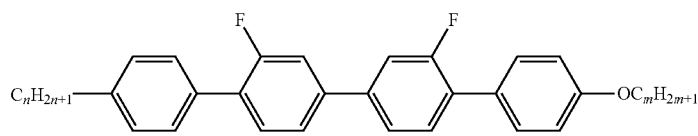
PGIGP-n-Om
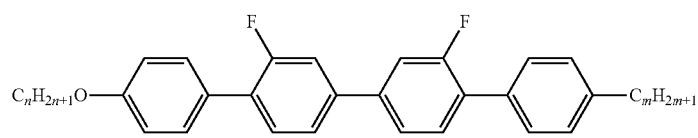
PGIGP-nO-m
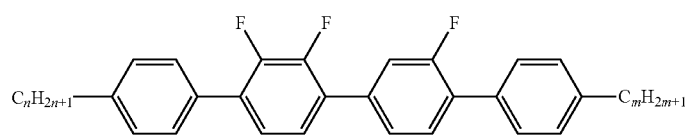
PYGP-n-m
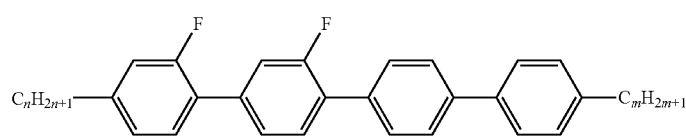
GGPP-n-m
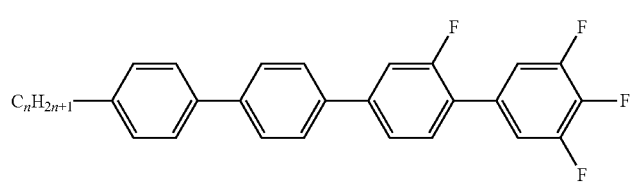
PPGU-n-F TABLE C-continued
Illustrative structures
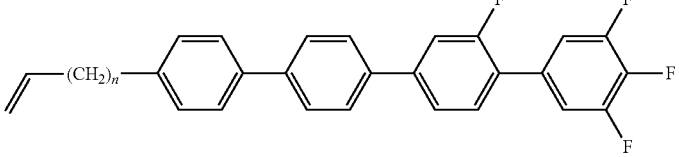
PPGU-Vn-F
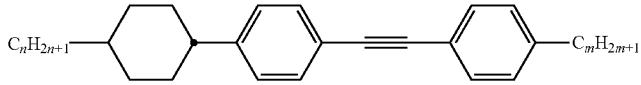
CPTP-n-m
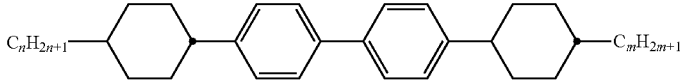
CPPC-n-m
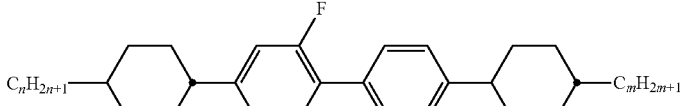
CGPC-n-m
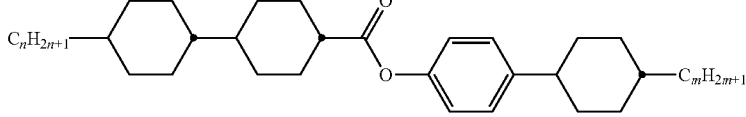
CCZPC-n-m
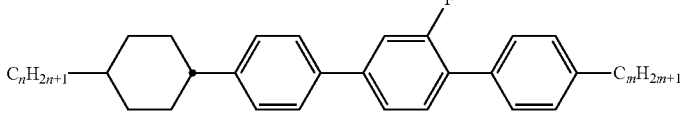
CPGP-n-m
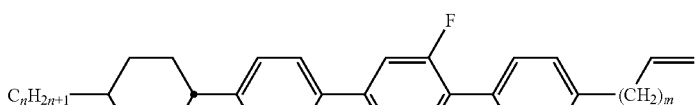
CPGP-n-mV
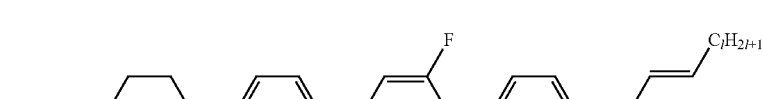
CPGP-n-mVl TABLE C-continued
| Illustrative structures |
| --- |
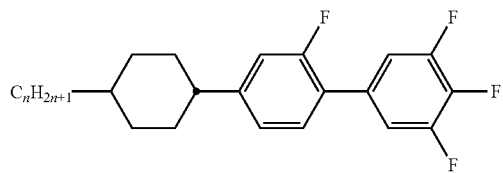
CGU-n-F
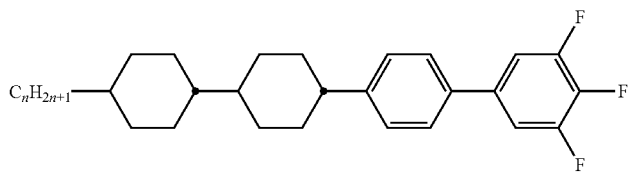
CCPU-n-F
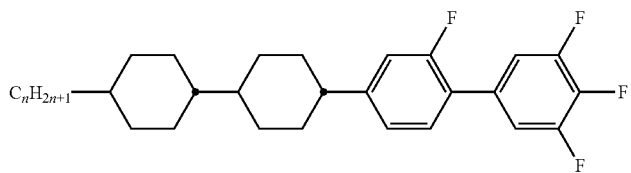
CCGU-n-F
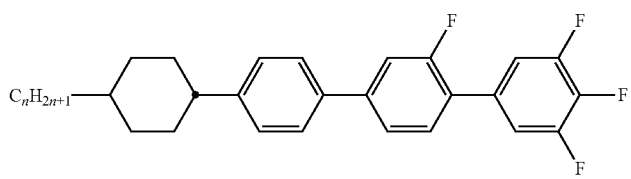
CPGU-n-F
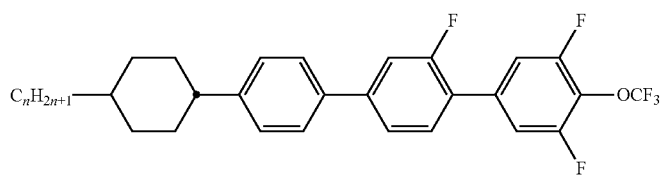
CPGU-n-OT
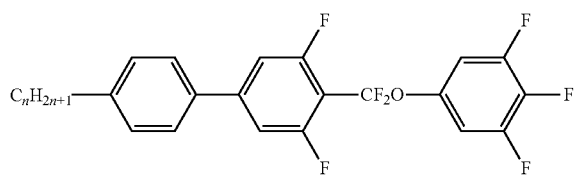
PUQU-n-F
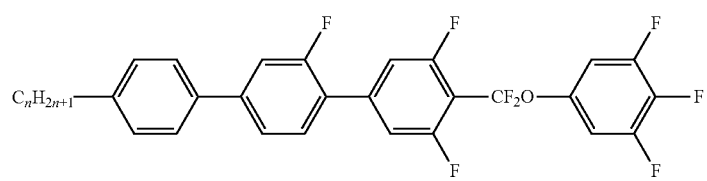
PGUQU-n-F

TABLE C-continued

Illustrative structures

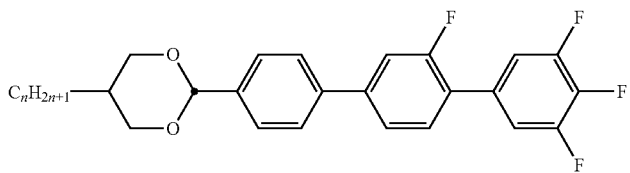

DPGU-n-F

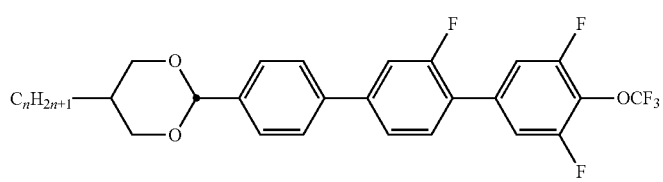

DPGU-n-OT

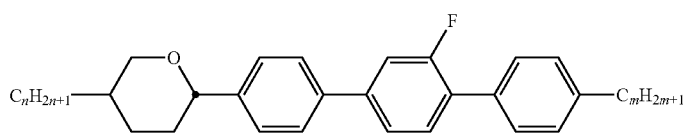

APGP-n-m

The following illustrative structures are compounds, which are preferably additionally used in the media:
in which m and n, identically or differently, are 1, 2, 3, 4, 5, 6 or 7.

Preferably, the medium according to the invention comprises one or more compounds selected from the compounds of Table C.

The following table, Table D, shows illustrative compounds which can be used as alternative stabilizers in the mesogenic media in accordance with the present invention. The total concentration of these and similar compounds in the media is preferably 5% or less.

TABLE D

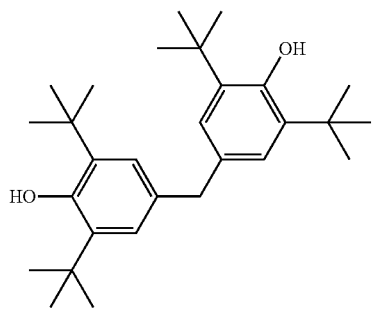 [SMILES: CC(C)(C)c1cc(Cc2cc(C(C)(C)C)c(O)c(C(C)(C)C)c2)cc(C(C)(C)C)c1O]

TABLE D-continued
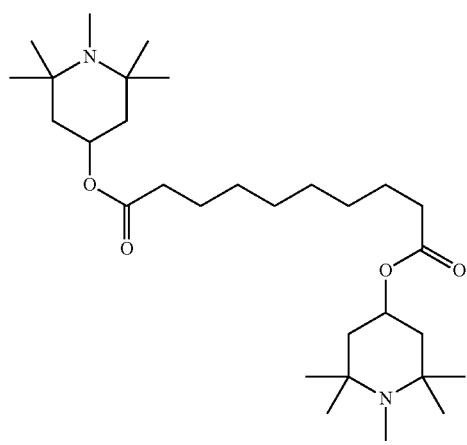
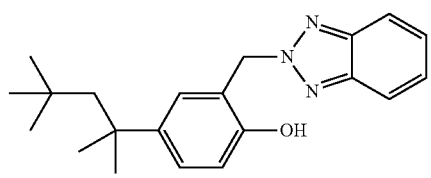 [SMILES: CC(C)(C)CC(C)(C)c1ccc(O)c(Cn2nc3ccccc3n2)c1]
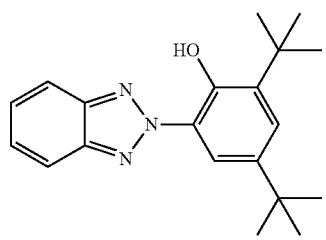 [SMILES: CC(C)(C)c1cc(-n2nc3ccccc3n2)c(O)c(C(C)(C)C)c1]
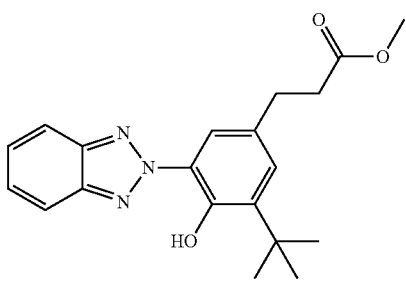 [SMILES: COC(=O)CCc1cc(-n2nc3ccccc3n2)c(O)c(C(C)(C)C)c1]
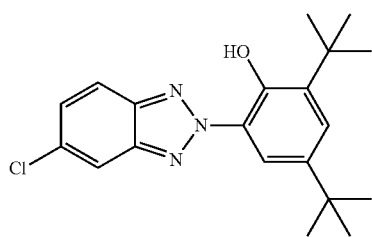 [SMILES: CC(C)(C)c1cc(-n2nc3ccc(Cl)cc3n2)c(O)c(C(C)(C)C)c1]

TABLE D-continued
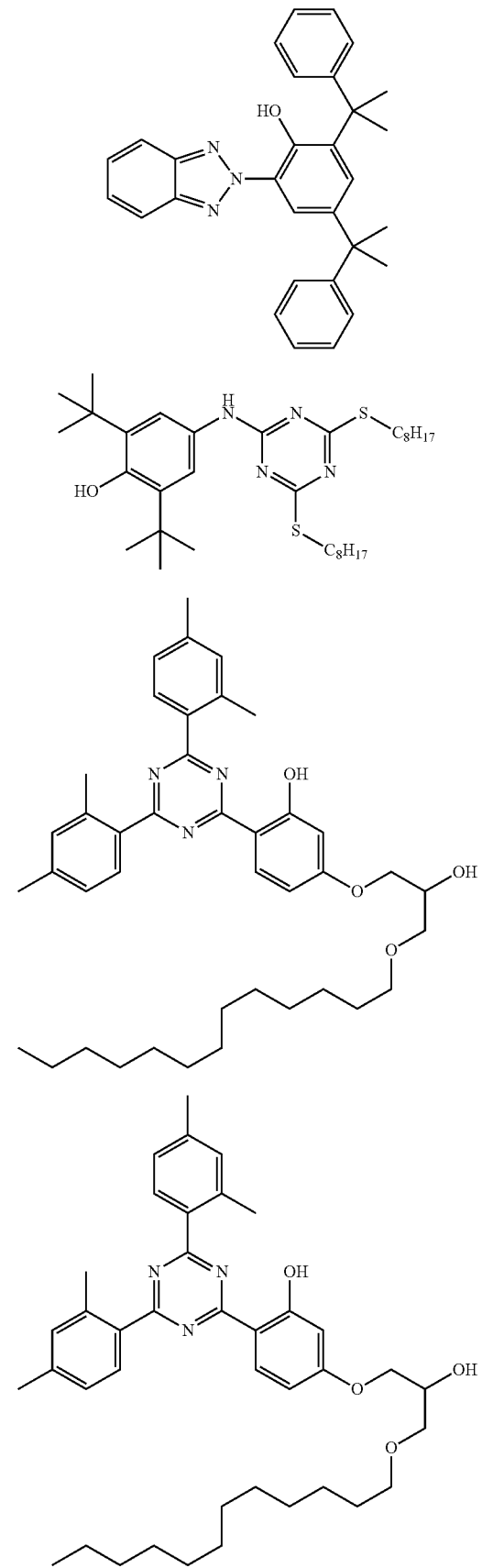

TABLE D-continued
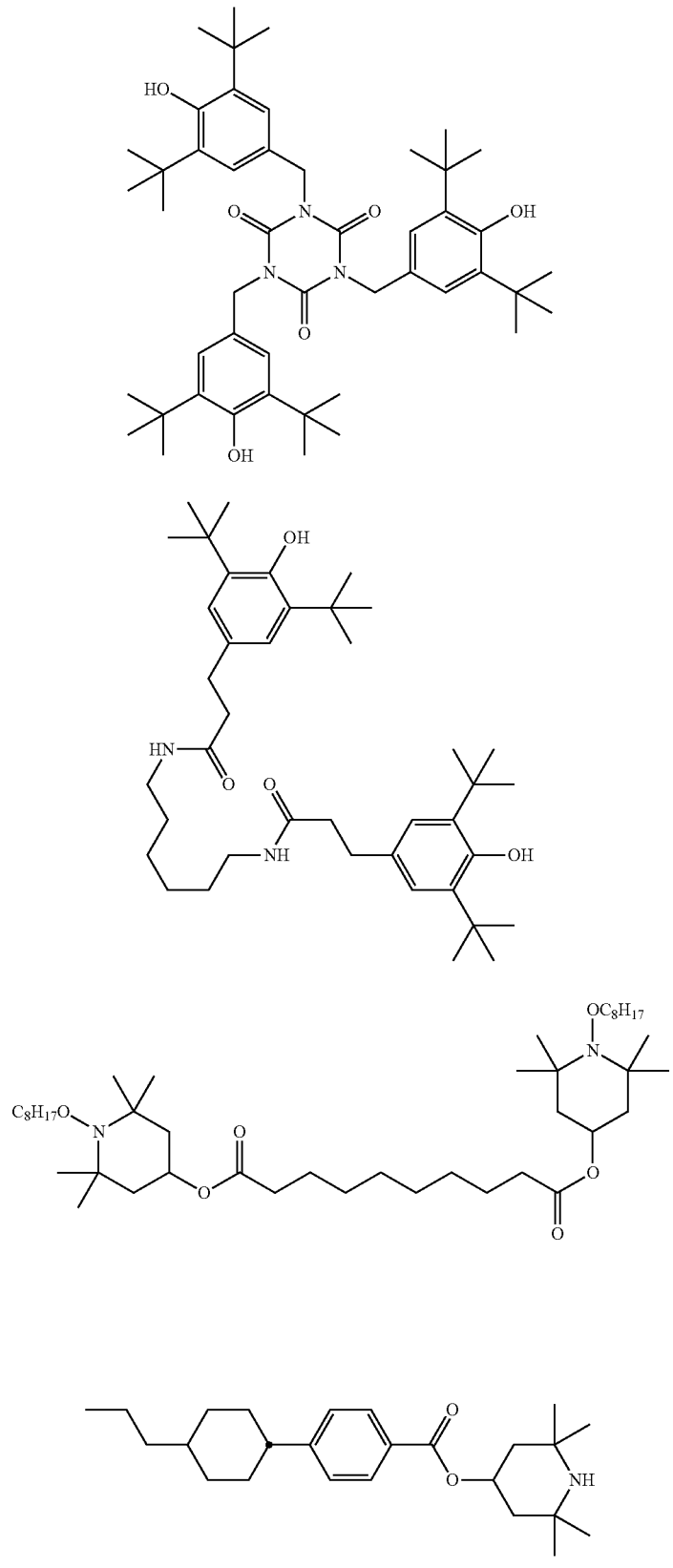

In a preferred embodiment of the present invention, the mesogenic media comprise one or more compounds selected from the group of the compounds from Table D. The following table, Table E, shows illustrative compounds which can preferably be used as chiral dopants in the mesogenic media in accordance with the present invention.
TABLE E
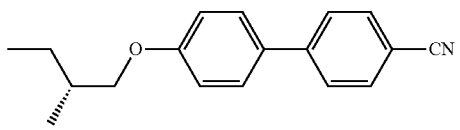 [SMILES: CC[C@@H](C)COc1ccc(-c2ccc(C#N)cc2)cc1]
C 15
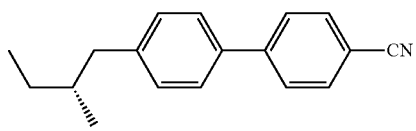 [SMILES: CC[C@@H](C)Cc1ccc(-c2ccc(C#N)cc2)cc1]
CB 15
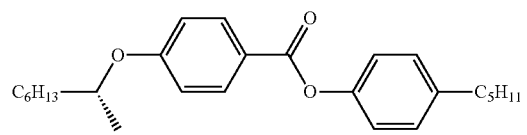
CM 21
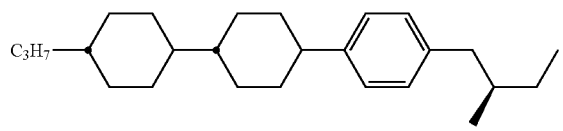
CM 44
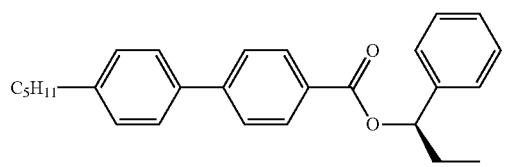
CM 45
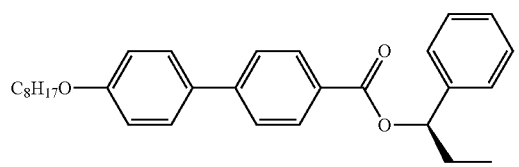
CM 47
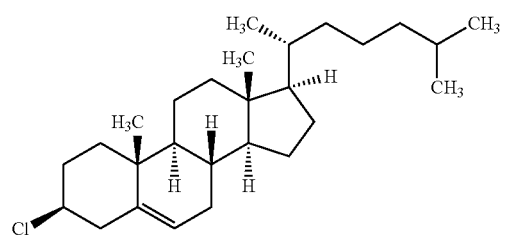
CC TABLE E-continued
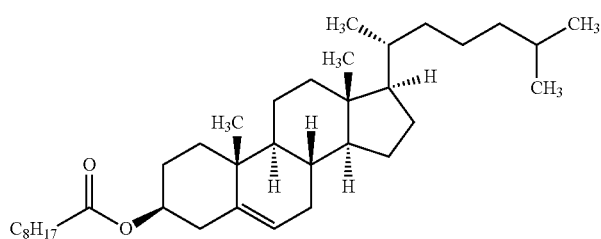
CN
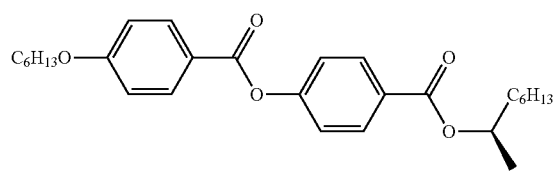
R/S-811
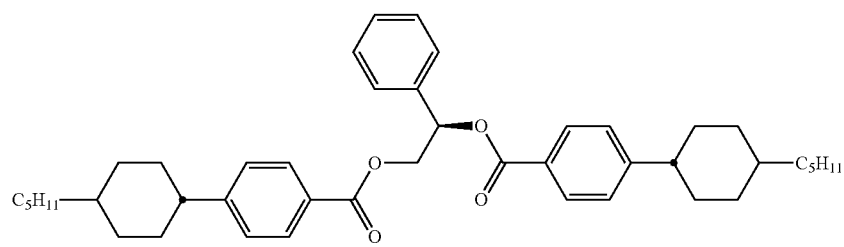
R/S-1011
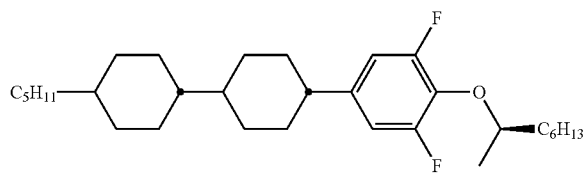
R/S-2011
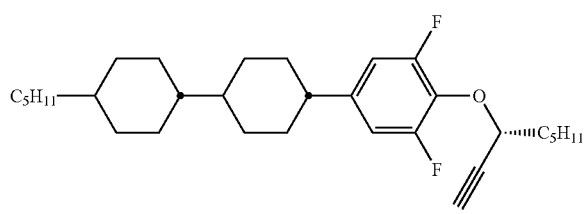
R/S-3011
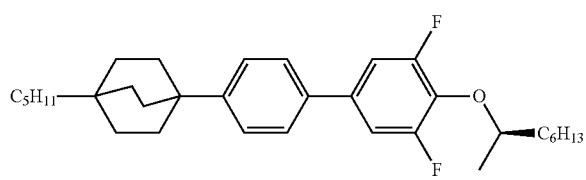
R/S-4011

TABLE E-continued

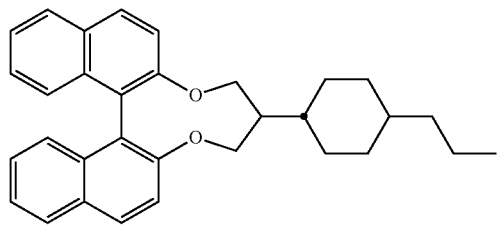

R/S-5011

In a preferred embodiment of the present invention, the mesogenic media comprise one or more compounds selected from the group of the compounds of Table E.

The mesogenic media in accordance with the present application preferably comprise two or more, preferably four or more, compounds selected from the group consisting of the compounds from the above tables.

EXAMPLES

The following examples illustrate the present invention without limiting it in any way. It is clear to the person skilled in the art from the physical properties what properties can be achieved and in what ranges they can be modified. In particular, the combination of the various properties which can preferably be achieved is thus well defined for the person skilled in the art.

SYNTHESIS EXAMPLES

Abbreviations

RT room temperature (typically 20° C.±1° C.)
THF tetrahydrofuran
MTB ether methyl-tert-butyl ether
DCM dichloromethane
dist. distilled Example 1: 2-Butyl-5-[2-[4-(3,5-difluoro-4-isothio-cyanato-phenyl)phenyl]ethynyl]-1,3-difluoro-benzene Step 1.1: 2-(4-Butyl-3,5-difluoro-phenyl)ethynyl-trimethyl-silane

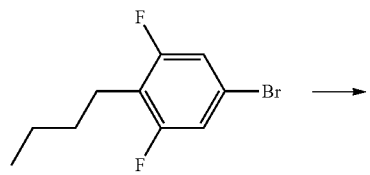

A mixture of 5-bromo-2-butyl-1,3-difluoro-benzene (CAS-no. 160976-00-1, 15.1 g, 61 mmol), trimethylsilyl acetylene (17.6 ml, 124 mmol), diisopropylamine (70 ml), copper(I)iodide (277 mg, 1.5 mmol) and bis(triphenylphosphine)-palladium(II)chloride (1.7 g, 2.4 mmol) is heated at reflux temperature overnight. Then the reaction mixture is cooled to RT, and MTB ether and dist. water are added. The aqueous phase is separated and extracted with MTB ether. The combined organic phases are washed with brine, dried (sodium sulfate) and concentrated in vacuo. The residue is purified by silica gel chromatography (n-heptane) to give 2-(4-butyl-3,5-difluoro-phenyl)ethynyl-trimethyl-silane as a yellow oil.

Step 1.2: 2-Butyl-5-ethynyl-1,3-difluoro-benzene

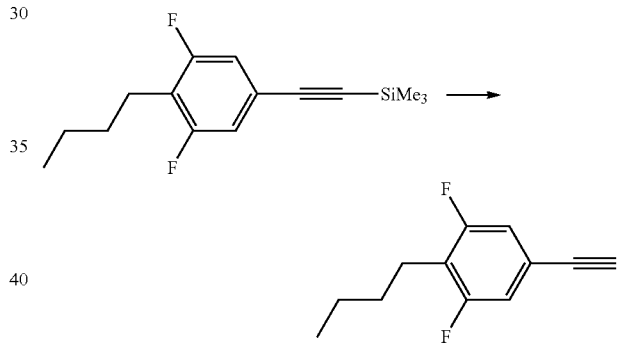

Tetra-n-butylammonium fluoride (1 M in THF, 60 ml) is added dropwise to a solution of 2-(4-butyl-3,5-difluoro-phenyl)ethynyl-trimethyl-silane (15.9 g, 60 mmol) in THF (350 ml) at RT, and the reaction mixture is stirred overnight. Then it is hydrolyzed by addition of HCl (1 N) and dist. water, and MBT ether is added. The aqueous phase is separated and extracted with MTB ether. The combined organic phases are washed with brine, dried (sodium sulfate) and concentrated in vacuo. The residue is purified by silica gel chromatography (heptane) to give 2-butyl-5-ethynyl-1,3-difluoro-benzene as a light yellow oil.

Step 1.3: 4-[4-[2-(4-Butyl-3,5-difluoro-phenyl)ethynyl]phenyl]-2,6-difluoro-aniline

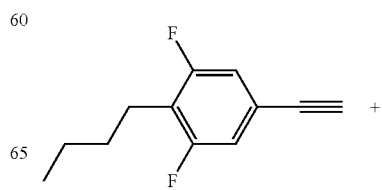

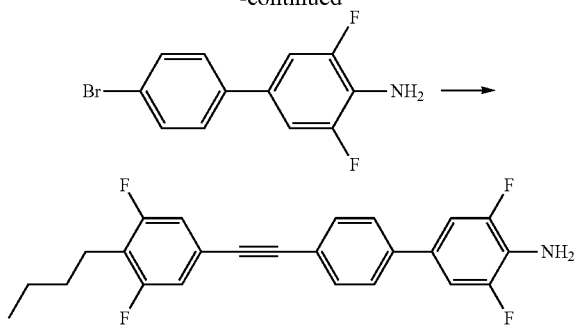

A solution of 2-butyl-5-ethynyl-1,3-difluoro-benzene (4.6 g, 24 mmol), 4-(4-bromophenyl)-2,6-difluoro-aniline (CAS-no. 2244281-20-5, 7.0 g, 23 mmol) and diisopropylamine (55 ml) in THF (60 ml) is heated at reflux temperature. Copper(I)iodide (4.4 mg), 2-dicyclohexylphosphino-2'4'6'-triisopropyl-1,1'-biphenyl (22 mg) and chloro(2-dicyclohexylphosphino-2'4'6'-triisopropyl-1,1'-biphenyl)(2'-amino-1,1'-biphenyl-2-yl)palladium(II) (37 mg) are added, and the reaction mixture is stirred at reflux temperature overnight. Then it is cooled to RT, filtered and concentrated in vacuo. The residue is purified by silica gel chromatography (heptane/MTB ether 5/1) and crystallization (heptane) to give 4-[4-[2-(4-butyl-3,5-difluoro-phenyl)ethynyl]phenyl]-2,6-difluoro-aniline as brown crystals.

Step 1.4: 2-Butyl-5-[2-[4-(3,5-difluoro-4-isothiocyanato-phenyl)phenyl]ethynyl]-1,3-difluoro-benzene

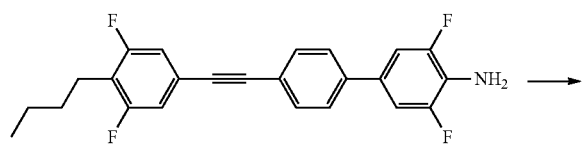

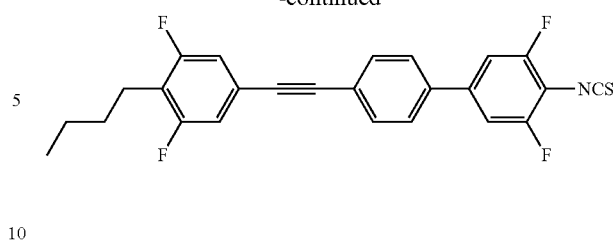

A solution of 4-[4-[2-(4-butyl-3,5-difluoro-phenyl)ethynyl]phenyl]-2,6-difluoro-aniline (7.4 g, 19 mmol) and 1,4-diazabicyclo[2.2.2]octane (5.2 g, 47 mmol) in DCM (70 ml) is cooled to 0° C. and treated dropwise with thiophosgene (1.6 ml, 20 mmol). The reaction mixture is stirred at RT for 60 min. Then it is hydrolyzed with brine, and the aqueous phase is separated and extracted with DCM. The combined organic phases are washed with brine, dried (sodium sulfate) and concentrated in vacuo. The residue is purified by silica gel chromatography (heptane) and crystallization (heptane) to give 2-butyl-5-[2-[4-(3,5-difluoro-4-isothiocyanato-phenyl)phenyl]ethynyl]-1,3-difluoro-benzene as light orange crystals.

Phase sequence: K 84 N 174 I. K 84 N 174.0 I

Δε=7.40

Δn=0.4180

$\gamma_1$=735 mPas

In analogy to Synthesis Example 1 the following compounds are obtained:

| No. | Compound | physical parameters |
|---|---|---|
| 2 | ![compound 2] | K 80 I<br>Δε = 5.50<br>Δn = 0.3090<br>$\gamma_1$ = 126 mPas |
| 3 | ![compound 3] | K 63 I<br>Δε = 4.90<br>Δn = 0.2722<br>$\gamma_1$ = 86 mPas |
| 4 | ![compound 4] | K 64 I<br>Δε = 4.70<br>Δn = 0.2870<br>$\gamma_1$ = 94 mPas |

-continued

| No. | Compound | physical parameters |
|---|---|---|
| 5 | | K 79 I<br>Δε = 5.43<br>Δn = 0.2690<br>γ₁ = 104 mPas |
| 6 | | K 111 N 151.0 I<br>Δε = 7.40<br>Δn = 0.3430<br>γ₁ = 878 mPas |
| 7 | | K 88 I<br>Δε = 3.89<br>Δn = 0.2376<br>γ₁ = 915 mPas |
| 8 | | K 113 N 172.2 I<br>Δε = 6.90<br>Δn = 0.4250<br>γ₁ = 707 mPas |
| 9 | | K 84 N 165.5 I<br>Δε = 7.60<br>Δn = 0.4213<br>γ₁ = 701 mPas |
| 10 | | K 73 N 170.0 I<br>Δε = 7.60<br>Δn = 0.4180<br>γ₁ = 753 mPas |
| 11 | | |
| 12 | | K 114 I<br>Δε = 4.70<br>Δn = 0.3770<br>γ₁ = 947 mPas |

-continued

| No. | Compound | physical parameters |
|---|---|---|
| 13 | (structure) | |
| 14 | (structure) | K 107 SmB 110 SmA 168 N 217.6<br>$\Delta\varepsilon = 9.90$<br>$\Delta n = 0.4390$<br>$\gamma_1 = 472$ mPas |
| 15 | (structure) | |
| 16 | (structure) | |
| 17 | (structure) | |
| 18 | (structure) | |
| 19 | (structure) | |
| 20 | (structure) | K 92 I<br>$\Delta\varepsilon = -0.3$<br>$\Delta n = 0.2570$<br>$\gamma_1 = 62$ mPas |

-continued
| No. | Compound | physical parameters |
|---|---|---|
| 21 | 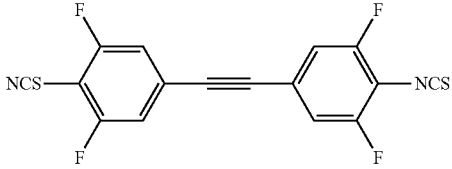 | K 140 I |
| 22 | 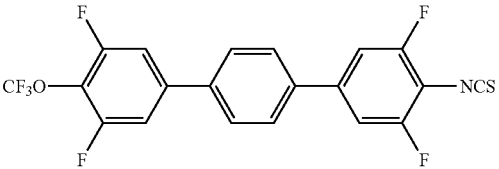 | K 127 N 164.1 I |
| 23 | 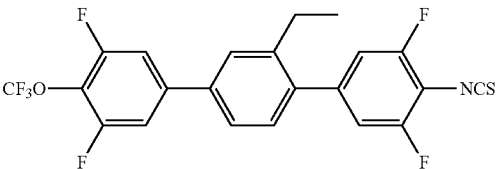 | Tg −23 K 78 I<br>Δε = −1.49<br>Δn = 0.1908<br>γ₁ = 607 mPas |
| 24 | 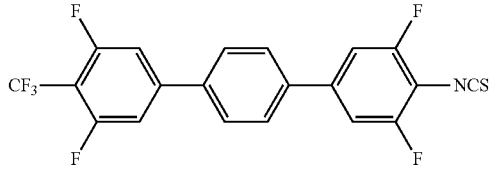 | K 149 I<br>Δε = 0.10<br>Δn = 0.3070 |
| 25 | 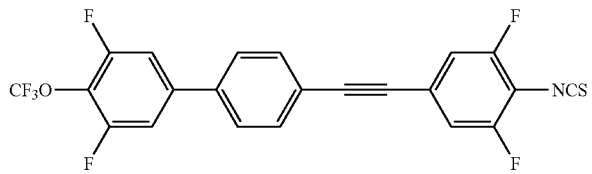 | K 115 N 182.9 I<br>Δε = 1.31<br>Δn = 0.3744<br>γ₁ = 489 mPas |
| 26 | 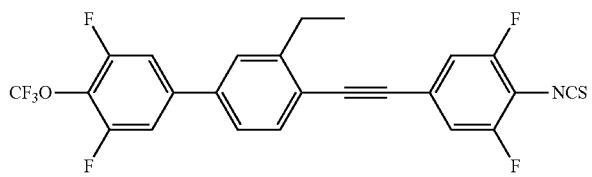 | K 139 N (115) I |
| 27 | 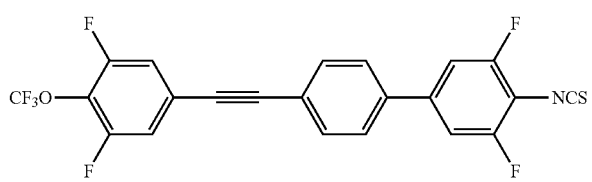 | K 116 N 184.4 I<br>Δε = 0.52<br>Δn = 0.3829<br>γ₁ = 603 mPas |

MIXTURE EXAMPLES

Liquid-crystal mixtures N1 to N19 and comparative mixture C1 having the compositions and properties as indicated in the following tables are prepared and characterized with respect to their general physical properties and their applicability in microwave components at 19 GHz and 20° C.

Comparative Mixture C1

| | | | |
|---|---|---|---|
| PPTU-4-S | 6.0% | T(N,l) [° C.]: | 158 |
| PPTU-5-S | 10.0% | Δn [589 nm, 20° C.]: | 0.3797 |
| PPU-TO-S | 22.0% | $n_e$ [589 nm, 20° C.]: | 1.9144 |
| CPU-2-S | 26.0% | $n_o$ [589 nm, 20° C.]: | 1.5347 |
| CPTU-4-S | 10.0% | Δε [1 kHz, 20° C.]: | 15.4 |
| CPTU-5-S | 14.0% | $\varepsilon_\parallel$ [1 kHz, 20° C.]: | 19.4 |
| P(2)TU-5-S | 12.0% | $\varepsilon_\perp$ [1 kHz, 20° C.]: | 4.0 |
| Σ | 100.0% | $\gamma_1$ [mPa s, 20° C.]: | 528 |
| | | $K_1$ [pN, 20° C.]: | 14.2 |
| | | $K_3$ [pN, 20° C.]: | 24.8 |
| | | $K_3/K_1$ [pN, 20° C.]: | 1.74 |
| | | $V_0$ [V, 20° C.]: | 1.01 |
| | | LTS bulk [h, −30° C.]: | 1000 |
| | | LTS bulk [h, −40° C.]: | 600 |
| | | τ [20° C., 19 GHz]: | 0.314 |
| | | $\varepsilon_{r,\parallel}$ [20° C., 19 GHz]: | 3.56 |
| | | $\varepsilon_{r,\perp}$ [20° C., 19 GHz]: | 2.45 |
| | | tan $\delta_{\varepsilon\ r,\parallel}$ [20° C., 19 GHz]: | 0.0056 |
| | | tan $\delta_{\varepsilon\ r,\perp}$ [20° C., 19 GHz]: | 0.0091 |
| | | η [20° C., 19 GHz]: | 34.5 |

Example N1

| | | | |
|---|---|---|---|
| PPTU-4-S | 6.0% | Δε [589 nm, 20° C.]: | 14.0 |
| PPTU-5-S | 12.0% | $\varepsilon_\parallel$ [1 kHz, 20° C.]: | 17.7 |
| PPU-TO-S | 23.0% | $\varepsilon_\perp$ [1 kHz, 20° C.]: | 3.7 |
| CPTU-5-S | 25.0% | $\gamma_1$ [mPa s, 20° C.]: | 631 |
| P(2)TU-5-S | 14.0% | $K_1$ [pN, 20° C.]: | 16.0 |
| CPU-2-S | 10.0% | $K_3$ [pN, 20° C.]: | 23.6 |
| UITPU-4-S | 10.0% | $K_3/K_1$ [pN, 20° C.]: | 1.47 |
| Σ | 100.0% | $V_0$ [V, 20° C.]: | 1.13 |
| | | τ [20° C., 19 GHz]: | 0.324 |
| | | $\varepsilon_{r,\parallel}$ [20° C., 19 GHz]: | 3.62 |
| | | $\varepsilon_{r,\perp}$ [20° C., 19 GHz]: | 2.45 |
| | | tan $\delta_{\varepsilon\ r,\parallel}$ [20° C., 19 GHz]: | 0.0051 |
| | | tan $\delta_{\varepsilon\ r,\perp}$ [20° C., 19 GHz]: | 0.0082 |
| | | η [20° C., 19 GHz]: | 39.7 |

Example N1 corresponds to Comparative mixture C1 and additionally comprises a compound of formula U according to the invention. An improvement of the material quality η from 34.5 to 39.7 is observed.

Example N2

| | | | |
|---|---|---|---|
| PPTU-4-S | 6.0% | T(N,l) [° C.]: | 159 |
| PPTU-5-S | 12.0% | Δε [589 nm, 20° C.]: | 15.0 |
| PPU-TO-S | 25.0% | $\varepsilon_\parallel$ [1 kHz, 20° C.]: | 18.7 |
| CPTU-5-S | 25.0% | $\varepsilon_\perp$ [1 kHz, 20° C.]: | 3.7 |
| PTU-3-S | 10.0% | $\gamma_1$ [mPa s, 20° C.]: | 530 |
| PTU-5-S | 10.0% | $K_1$ [pN, 20° C.]: | 17.0 |
| UITPU-4-S | 12.0% | $K_3$ [pN, 20° C.]: | 26.2 |
| Σ | 100.0% | $K_3/K_1$ [pN, 20° C.]: | 1.54 |
| | | $V_0$ [V, 20° C.]: | 1.13 |
| | | τ [20° C., 19 GHz]: | 0.338 |
| | | $\varepsilon_{r,\parallel}$ [20° C., 19 GHz]: | 3.69 |
| | | $\varepsilon_{r,\perp}$ [20° C., 19 GHz]: | 2.44 |
| | | tan $\delta_{\varepsilon\ r,\parallel}$ [20° C., 19 GHz]: | 0.0055 |
| | | tan $\delta_{\varepsilon\ r,\perp}$ [20° C., 19 GHz]: | 0.0089 |
| | | η [20° C., 19 GHz]: | 38.2 |

Example N3

| | | | |
|---|---|---|---|
| PGU-3-S | 13.0% | τ [20° C., 19 GHz]: | 159.9 |
| PPTU-4-S | 6.0% | $\varepsilon_{r,\parallel}$ [20° C., 19 GHz]: | 0.323 |
| PPTU-5-S | 10.0% | $\varepsilon_{r,\perp}$ [20° C., 19 GHz]: | 3.6339 |
| PPU-TO-S | 22.0% | tan $\delta_{\varepsilon\ r,\parallel}$ [20° C., 19 GHz]: | 2.4589 |
| CPTU-4-S | 8.0% | tan $\delta_{\varepsilon\ r,\perp}$ [20° C., 19 GHz]: | 0.0050 |
| CPTU-5-S | 12.0% | η [20° C., 19 GHz]: | 0.0082 |
| UITU-3-S | 7.0% | τ [20° C., 19 GHz]: | 39.3 |
| UITU-5-S | 7.0% | | |
| CPU(F,F)-3-S | 15.0% | | |
| Σ | 100.0% | | |

Example N4

| | | | |
|---|---|---|---|
| PPTU-4-S | 6.0% | τ [20° C., 19 GHz]: | 160.7 |
| PPTU-5-S | 10.0% | $\varepsilon_{r,\parallel}$ [20° C., 19 GHz]: | 0.318 |
| PPU-TO-S | 22.0% | $\varepsilon_{r,\perp}$ [20° C., 19 GHz]: | 3.6235 |
| CPU-2-S | 22.0% | tan $\delta_{\varepsilon\ r,\parallel}$ [20° C., 19 GHz]: | 2.4719 |
| CPTU-4-S | 8.0% | tan $\delta_{\varepsilon\ r,\perp}$ [20° C., 19 GHz]: | 0.0054 |
| CPTU-5-S | 12.0% | η [20° C., 19 GHz]: | 0.0085 |
| UITU-3-S | 7.0% | τ [20° C., 19 GHz]: | 37.2 |
| UITU-5-S | 7.0% | | |
| PPTU-TO-S | 6.0% | | |
| Σ | 100.0% | | |

Example N5

| | | | |
|---|---|---|---|
| PPTU-4-S | 6.0% | τ [20° C., 19 GHz]: | 158.5 |
| PPTU-5-S | 10.0% | $\varepsilon_{r,\parallel}$ [20° C., 19 GHz]: | 0.322 |
| PPU-TO-S | 22.0% | $\varepsilon_{r,\perp}$ [20° C., 19 GHz]: | 3.6162 |
| CPU-2-S | 22.0% | tan $\delta_{\varepsilon\ r,\parallel}$ [20° C., 19 GHz]: | 2.4511 |
| CPTU-4-S | 8.0% | tan $\delta_{\varepsilon\ r,\perp}$ [20° C., 19 GHz]: | 0.0053 |
| CPTU-5-S | 12.0% | η [20° C., 19 GHz]: | 0.0084 |
| UITU-3-S | 7.0% | τ [20° C., 19 GHz]: | 38.4 |
| UITU-5-S | 7.0% | | |
| PP(1)TU-TO-S | 6.0% | | |
| Σ | 100.0% | | |

Example N6

| | | | |
|---|---|---|---|
| PPTU-4-S | 6.0% | τ [20° C., 19 GHz]: | 157.2 |
| PPTU-5-S | 10.0% | LTS bulk [h, −30° C.]: | 144 |
| PPU-TO-S | 22.0% | τ [20° C., 19 GHz]: | 0.323 |

-continued

| | | | |
|---|---|---|---|
| CPU-2-S | 22.0% | $\varepsilon_{r,\parallel}$ [20° C., 19 GHz]: | 3.6535 |
| CPTU-4-S | 8.0% | $\varepsilon_{r,\perp}$ [20° C., 19 GHz]: | 2.4726 |
| CPTU-5-S | 12.0% | $\tan \delta_{\varepsilon\,r,\parallel}$ [20° C., 19 GHz]: | 0.0053 |
| UITU-3-S | 6.0% | $\tan \delta_{\varepsilon\,r,\perp}$ [20° C., 19 GHz]: | 0.0084 |
| UITU-5-S | 6.0% | $\eta$ [20° C., 19 GHz]: | 38.4 |
| ThTU-5-S | 8.0% | | |
| Σ | 100.0% | | |

Example N7

| | | | |
|---|---|---|---|
| PPTU-4-S | 6.0% | $\tau$ [20° C., 19 GHz]: | 151.4 |
| PPTU-5-S | 10.0% | LTS bulk [h, −30° C.]: | 120 |
| PPU-TO-S | 20.0% | $\tau$ [20° C., 19 GHz]: | 0.326 |
| CPU-2-S | 20.0% | $\varepsilon_{r,\parallel}$ [20° C., 19 GHz]: | 3.6117 |
| CPTU-4-S | 8.0% | $\varepsilon_{r,\perp}$ [20° C., 19 GHz]: | 2.4338 |
| CPTU-5-S | 12.0% | $\tan \delta_{\varepsilon\,r,\parallel}$ [20° C., 19 GHz]: | 0.0053 |
| UITU-3-S | 7.0% | $\tan \delta_{\varepsilon\,r,\perp}$ [20° C., 19 GHz]: | 0.0082 |
| UITU-5-S | 7.0% | $\eta$ [20° C., 19 GHz]: | 39.8 |
| ThTU-n-S | 10.0% | | |
| Σ | 100.0% | | |

Example N8

| | | | |
|---|---|---|---|
| PTU-3-S | 6.0% | $\tau$ [20° C., 19 GHz]: | 160 |
| PTU-5-S | 6.0% | $\varepsilon_{r,\parallel}$ [20° C., 19 GHz]: | 0.345 |
| PPTU-4-S | 8.0% | $\varepsilon_{r,\perp}$ [20° C., 19 GHz]: | 3.7673 |
| PPTU-5-S | 10.0% | $\tan \delta_{\varepsilon\,r,\parallel}$ [20° C., 19 GHz]: | 2.4678 |
| PGTU-4-S | 6.0% | $\tan \delta_{\varepsilon\,r,\perp}$ [20° C., 19 GHz]: | 0.0057 |
| PPU-TO-S | 24.0% | $\eta$ [20° C., 19 GHz]: | 0.0097 |
| CPTU-4-S | 8.0% | $\tau$ [20° C., 19 GHz]: | 35.6 |
| CPTU-5-S | 14.0% | | |
| PPTU-TO-S | 10.0% | | |
| UITU-3-S | 4.0% | | |
| UITU-5-S | 4.0% | | |
| Σ | 100.0% | | |

Example N9

| | | | |
|---|---|---|---|
| PPTU-4-S | 6.0% | T(N,l) [° C.]: | 148.5 |
| PPTU-5-S | 12.0% | Δε [589 nm, 20° C.]: | 14.0 |
| PGU-3-S | 14.0% | $\varepsilon_{\parallel}$ [1 kHz, 20° C.]: | 17.8 |
| PPU-TO-S | 28.0% | $\varepsilon_{\perp}$ [1 kHz, 20° C.]: | 3.8 |
| CPTU-4-S | 20.0% | $K_1$ [pN, 20° C.]: | 15.6 |
| UITU-3-S | 10.0% | $K_3$ [pN, 20° C.]: | 24.0 |
| UITU-5-S | 10.0% | $K_3/K_1$ [pN, 20° C.]: | 1.54 |
| Σ | 100.0% | $V_0$ [V, 20° C.]: | 1.07 |
| | | $\tau$ [20° C., 19 GHz]: | 0.330 |
| | | $\varepsilon_{r,\parallel}$ [20° C., 19 GHz]: | 3.6647 |
| | | $\varepsilon_{r,\perp}$ [20° C., 19 GHz]: | 2.4566 |
| | | $\tan \delta_{\varepsilon\,r,\parallel}$ [20° C., 19 GHz]: | 0.0055 |
| | | $\tan \delta_{\varepsilon\,r,\perp}$ [20° C., 19 GHz]: | 0.0091 |
| | | $\eta$ [20° C., 19 GHz]: | 36.3 |

Example N10

| | | | |
|---|---|---|---|
| PPTU-4-S | 6.0% | T(N,l) [° C.]: | 155 |
| PPTU-5-S | 12.0% | $\tau$ [20° C., 19 GHz]: | 0.327 |
| PPU-TO-S | 28.0% | $\varepsilon_{r,\parallel}$ [20° C., 19 GHz]: | 3.6644 |
| CPTU-4-S | 14.0% | $\varepsilon_{r,\perp}$ [20° C., 19 GHz]: | 2.4661 |
| CPTU-5-S | 20.0% | $\tan \delta_{\varepsilon\,r,\parallel}$ [20° C., 19 GHz]: | 0.0052 |
| UITU-3-S | 10.0% | $\tan \delta_{\varepsilon\,r,\perp}$ [20° C., 19 GHz]: | 0.0080 |
| UITU-5-S | 10.0% | $\eta$ [20° C., 19 GHz]: | 40.9 |
| Σ | 100.0% | | |

Example N11

| | | | |
|---|---|---|---|
| PPTU-4-S | 6.0% | T(N,l) [° C.]: | 160 |
| PPTU-5-S | 12.0% | LTS bulk [h, −20° C.]: | 268 |
| PPU-TO-S | 20.0% | $\tau$ [20° C., 19 GHz]: | 0.325 |
| CPU-2-S | 16.0% | $\varepsilon_{r,\parallel}$ [20° C., 19 GHz]: | 3.5874 |
| CPTU-4-S | 12.0% | $\varepsilon_{r,\perp}$ [20° C., 19 GHz]: | 2.4224 |
| CPTU-5-S | 18.0% | $\tan \delta_{\varepsilon\,r,\parallel}$ [20° C., 19 GHz]: | 0.0051 |
| UITU-3-S | 8.0% | $\tan \delta_{\varepsilon\,r,\perp}$ [20° C., 19 GHz]: | 0.0079 |
| UITU-5-S | 8.0% | $\eta$ [20° C., 19 GHz]: | 41.1 |
| Σ | 100.0% | | |

Example N12

| | | | |
|---|---|---|---|
| PPTU-4-S | 6.0% | T(N,l) [° C.]: | 160 |
| PPTU-5-S | 10.0% | $\tau$ [20° C., 19 GHz]: | 0.324 |
| PPU-TO-S | 22.0% | $\varepsilon_{r,\parallel}$ [20° C., 19 GHz]: | 3.5821 |
| CPU-2-S | 24.0% | $\varepsilon_{r,\perp}$ [20° C., 19 GHz]: | 2.4228 |
| CPTU-4-S | 10.0% | $\tan \delta_{\varepsilon\,r,\parallel}$ [20° C., 19 GHz]: | 0.0054 |
| CPTU-5-S | 14.0% | $\tan \delta_{\varepsilon\,r,\perp}$ [20° C., 19 GHz]: | 0.0085 |
| UITU-3-S | 7.0% | $\eta$ [20° C., 19 GHz]: | 38.1 |
| UITU-5-S | 7.0% | | |
| Σ | 100.0% | | |

Example N13

| | | | |
|---|---|---|---|
| PPTU-4-S | 6.0% | T(N,l) [° C.]: | 162 |
| PPTU-5-S | 10.0% | $\tau$ [20° C., 19 GHz]: | 0.302 |
| CPU-2-S | 28.0% | $\varepsilon_{r,\parallel}$ [20° C., 19 GHz]: | 3.5488 |
| CPU-4-S | 22.0% | $\varepsilon_{r,\perp}$ [20° C., 19 GHz]: | 2.4763 |
| PPU-TO-S | 24.0% | $\tan \delta_{\varepsilon\,r,\parallel}$ [20° C., 19 GHz]: | 0.0057 |
| UITU-3-S | 5.0% | $\tan \delta_{\varepsilon\,r,\perp}$ [20° C., 19 GHz]: | 0.0090 |
| UITU-5-S | 5.0% | $\eta$ [20° C., 19 GHz]: | 33.6 |
| Σ | 100.0% | | |

Example N14

| | | | |
|---|---|---|---|
| PPTU-4-S | 6.0% | T(N,I) [° C.]: | 160.5 |
| PPTU-5-S | 10.0% | LTS bulk [h, −20° C.]: | 168 |
| PPU-TO-S | 22.0% | τ [20° C., 19 GHz]: | 0.321 |
| CPU-2-S | 24.0% | $\varepsilon_{r,\|}$ [20° C., 19 GHz]: | 3.5871 |
| CPTU-5-S | 24.0% | $\varepsilon_{r,\perp}$ [20° C., 19 GHz]: | 2.4362 |
| UITU-3-S | 7.0% | tan $\delta_{\varepsilon\,r,\|}$ [20° C., 19 GHz]: | 0.0052 |
| UITU-5-S | 7.0% | tan $\delta_{\varepsilon\,r,\perp}$ [20° C., 19 GHz]: | 0.0082 |
| Σ | 100.0% | η [20° C., 19 GHz]: | 39.1 |

Example N15

| | | | |
|---|---|---|---|
| PPTU-4-S | 6.0% | LTS bulk [h, −20° C.]: | 96 |
| PPTU-5-S | 10.0% | τ [20° C., 19 GHz]: | 0.318 |
| PPU-TO-S | 22.0% | $\varepsilon_{r,\|}$ [20° C., 19 GHz]: | 3.5865 |
| CPU-2-S | 24.0% | $\varepsilon_{r,\perp}$ [20° C., 19 GHz]: | 2.4446 |
| CPTU-4-S | 24.0% | tan $\delta_{\varepsilon\,r,\|}$ [20° C., 19 GHz]: | 0.0055 |
| UITU-3-S | 7.0% | tan $\delta_{\varepsilon\,r,\perp}$ [20° C., 19 GHz]: | 0.0086 |
| UITU-5-S | 7.0% | η [20° C., 19 GHz]: | 37.0 |
| Σ | 100.0% | | |

Example N16

| | |
|---|---|
| PPTU-4-S | 6.0% |
| PPTU-5-S | 10.0% |
| PPU-TO-S | 20.0% |
| CPU-2-S | 20.0% |
| CPTU-4-S | 10.0% |
| CPTU-5-S | 20.0% |
| UITU-3-S | 7.0% |
| UITU-5-S | 7.0% |
| Σ | 100.0% |

Example N17

| | |
|---|---|
| PPTU-4-S | 6.0% |
| PPTU-5-S | 10.0% |
| PPU-TO-S | 20.0% |
| CPU-2-S | 18.0% |
| CPTU-4-S | 10.0% |
| CPTU-5-S | 20.0% |
| UITU-3-S | 8.0% |
| UITU-5-S | 8.0% |
| Σ | 100.0% |

Example N18

| | | | |
|---|---|---|---|
| PPTU-4-S | 6.0% | T(N,I) [° C.]: | 157 |
| PPTU-5-S | 14.0% | τ [20° C., 19 GHz]: | 0.322 |
| CPTU-5-S | 25.0% | $\varepsilon_{r,\|}$ [20° C., 19 GHz]: | 3.60 |
| PTU-3-S | 9.0% | $\varepsilon_{r,\perp}$ [20° C., 19 GHz]: | 2.44 |
| PTU-5-S | 9.0% | tan $\delta_{\varepsilon\,r,\|}$ [20° C., 19 GHz]: | 0.0049 |
| UITPU-4-S | 12.0% | tan $\delta_{\varepsilon\,r,\perp}$ [20° C., 19 GHz]: | 0.0085 |
| CPU-2-S | 25.0% | η [20° C., 19 GHz]: | 38.1 |
| Σ | 100.0% | | |

Example N19

| | | | |
|---|---|---|---|
| PPTU-4-S | 6.0% | T(N,I) [° C.]: | 156 |
| PPTU-5-S | 12.0% | τ [20° C., 19 GHz]: | 0.331 |
| PPU-TO-S | 20.0% | $\varepsilon_{r,\|}$ [20° C., 19 GHz]: | 3.65 |
| CPTU-5-S | 22.0% | $\varepsilon_{r,\perp}$ [20° C., 19 GHz]: | 2.44 |
| PTU-3-S | 10.0% | tan $\delta_{\varepsilon\,r,\|}$ [20° C., 19 GHz]: | 0.0052 |
| PTU-5-S | 10.0% | tan $\delta_{\varepsilon\,r,\perp}$ [20° C., 19 GHz]: | 0.0085 |
| IS-8706 | 10.0% | η [20° C., 19 GHz]: | 39.2 |
| UITPU-4-S | 10.0% | | |
| Σ | 100.0% | | |

Example N20

| | | | |
|---|---|---|---|
| PPTU-4-S | 6.0% | T(N,I) [° C.]: | 165 |
| PPTU-5-S | 12.0% | Δε [1 kHz, 20° C.]: | 17.4 |
| PPU-TO-S | 11.0% | $\varepsilon_{\|}$ [1 kHz, 20° C.]: | 21.2 |
| CPTU-5-S | 25.0% | $\varepsilon_{\perp}$ [1 kHz, 20° C.]: | 3.8 |
| CPU-2-S | 22.0% | $\gamma_1$ [mPa s, 20° C.]: | 532 |
| PTU-3-S | 7.0% | $K_3$ [pN, 20° C.]: | 17.0 |
| PTU-5-S | 7.0% | $K_1$ [pN, 20° C.]: | 24.0 |
| UITPU-4-S | 10.0% | $K_3/K_1$ [pN, 20° C.]: | 1.42 |
| Σ | 100.0% | $V_0$ [V, 20° C.]: | 1.04 |
| | | LTS bulk [h, −40°C]: | 192 |
| | | τ [20° C., 19 GHz]: | 0.328 |
| | | $\varepsilon_{r,\|}$ [20° C., 19 GHz]: | 3.60 |
| | | $\varepsilon_{r,\perp}$ [20° C., 19 GHz]: | 2.42 |
| | | tan $\delta_{\varepsilon\,r,\|}$ [20° C., 19 GHz]: | 0.0051 |
| | | tan $\delta_{\varepsilon\,r,\perp}$ [20° C., 19 GHz]: | 0.0084 |
| | | η [20° C., 19 GHz]: | 39.0 |

Example N21

| | | | |
|---|---|---|---|
| PPTU-4-S | 6.0% | T(N,I) [° C.]: | 165 |
| PPTU-5-S | 12.0% | τ [20° C., 19 GHz]: | 0.325 |
| PPU-TO-S | 11.0% | $\varepsilon_{r,\|}$ [20° C., 19 GHz]: | 3.56 |
| CPTU-5-S | 25.0% | $\varepsilon_{r,\perp}$ [20° C., 19 GHz]: | 2.41 |
| CPU-2-S | 20.0% | tan $\delta_{\varepsilon\,r,\|}$ [20° C., 19 GHz]: | 0.0050 |
| PTU-3-S | 7.0% | tan $\delta_{\varepsilon\,r,\perp}$ [20° C., 19 GHz]: | 0.0081 |
| PTU-5-S | 7.0% | η [20° C., 19 GHz]: | 40.1 |
| UITPU-5-S | 12.0% | | |
| Σ | 100.0% | | |

Example N22

| | | | |
|---|---|---|---|
| PPTU-4-S | 6.0% | T(N,I) [° C.]: | 165 |
| PPTU-5-S | 12.0% | $\Delta\varepsilon$ [1 kHz, 20° C.]: | 17.1 |
| PPU-TO-S | 11.0% | $\varepsilon_\parallel$ [1 kHz, 20° C.]: | 20.8 |
| CPTU-5-S | 25.0% | $\varepsilon_\perp$ [1 kHz, 20° C.]: | 3.8 |
| CPU-2-S | 20.0% | $\gamma_1$ [mPa s, 20° C.]: | 548 |
| PTU-3-S | 7.0% | $K_3$ [pN, 20° C.]: | 17.0 |
| PTU-5-S | 7.0% | $K_1$ [pN, 20° C.]: | 24.9 |
| UITPU-5-S | 12.0% | $K_3/K_1$ [pN, 20° C.]: | 1.47 |
| $\Sigma$ | 100.0% | $V_0$ [V, 20° C.]: | 1.07 |
| | | LTS bulk [h, -40°C]: | 336 |
| | | $\tau$ [20° C., 19 GHz]: | 0.328 |
| | | $\varepsilon_{r,\parallel}$ [20° C., 19 GHz]: | 3.60 |
| | | $\varepsilon_{r,\perp}$ [20° C., 19 GHz]: | 2.42 |
| | | $\tan\delta_{\varepsilon\,r,\parallel}$ [20° C., 19 GHz]: | 0.0050 |
| | | $\tan\delta_{\varepsilon\,r,\perp}$ [20° C., 19 GHz]: | 0.0083 |
| | | $\eta$ [20° C., 19 GHz]: | 39.5 |

Example N23

| | | | |
|---|---|---|---|
| PPTU-4-S | 6.0% | T(N,I) [° C.]: | 163 |
| PPTU-5-S | 12.0% | $\tau$ [20° C., 19 GHz]: | 0.332 |
| PPU-TO-S | 15.0% | $\varepsilon_{r,\parallel}$ [20° C., 19 GHz]: | 3.60 |
| CPTU-5-S | 25.0% | $\varepsilon_{r,\perp}$ [20° C., 19 GHz]: | 2.40 |
| CPU-2-S | 14.0% | $\tan\delta_{\varepsilon\,r,\parallel}$ [20° C., 19 GHz]: | 0.0051 |
| PTU-3-S | 8.0% | $\tan\delta_{\varepsilon\,r,\perp}$ [20° C., 19 GHz]: | 0.0084 |
| PTU-5-S | 8.0% | $\eta$ [20° C., 19 GHz]: | 39.5 |
| UITPU-4-S | 7.35 | | |
| UITPU-5-S | 4.65 | | |
| $\Sigma$ | 100.0% | | |

Example N24

| | | | |
|---|---|---|---|
| PTU-3-S | 10.0% | T(N,I) [° C.]: | 156 |
| PTU-5-S | 10.0% | $\Delta\varepsilon$ [1 kHz, 20° C.]: | 19.3 |
| PPTU-4-S | 6.0% | $\varepsilon_\parallel$ [1 kHz, 20° C.]: | 23.4 |
| PPTU-5-S | 11.0% | $\varepsilon_\perp$ [1 kHz, 20° C.]: | 4.0 |
| PGTU-4-S | 6.0% | $K_1$ [pN, 20° C.]: | 18.4 |
| PGU-3-S | 12.0% | $K_3$ [pN, 20° C.]: | 24.4 |
| PPU-TO-S | 13.0% | $K_3/K_1$ [pN, 20° C.]: | 1.33 |
| CPTU-5-S | 22.0% | $V_0$ [V, 20° C.]: | 1.03 |
| UIPTU-5-S | 10.0% | $\tau$ [20° C., 19 GHz]: | 0.338 |
| $\Sigma$ | 100.0% | $\varepsilon_{r,\parallel}$ [20° C., 19 GHz]: | 3.71 |
| | | $\varepsilon_{r,\perp}$ [20° C., 19 GHz]: | 2.46 |
| | | $\tan\delta_{\varepsilon\,r,\parallel}$ [20° C., 19 GHz]: | 0.0056 |
| | | $\tan\delta_{\varepsilon\,r,\perp}$ [20° C., 19 GHz]: | 0.0102 |
| | | $\eta$ [20° C., 19 GHz]: | 33.1 |

Example N25

| | | | |
|---|---|---|---|
| PPTU-4-S | 10.0% | T(N,I) [° C.]: | 166 |
| PPTU-5-S | 20.0% | $\Delta\varepsilon$ [1 kHz, 20° C.]: | 14.5 |
| CPTU-5-S | 13.0% | $\varepsilon_\parallel$ [1 kHz, 20° C.]: | 17.9 |
| PGTU-4-S | 10.0% | $\varepsilon_\perp$ [1 kHz, 20° C.]: | 3.4 |
| PPTU-TO-S | 10.0% | $K_1$ [pN, 20° C.]: | 21.5 |
| PTUI-4-S | 17.0% | $K_3$ [pN, 20° C.]: | 22.5 |
| UIPTU-5-S | 20.0 % | $K_3/K_1$ [pN, 20° C.]: | 1.05 |
| $\Sigma$ | 100.0% | $V_0$ [V, 20° C.]: | 1.29 |
| | | $\tau$ [20° C., 19 GHz]: | 0.357 |
| | | $\varepsilon_{r,\parallel}$ [20° C., 19 GHz]: | 3.82 |
| | | $\varepsilon_{r,\perp}$ [20° C., 19 GHz]: | 2.46 |
| | | $\tan\delta_{\varepsilon\,r,\parallel}$ [20° C., 19 GHz]: | 0.0049 |
| | | $\tan\delta_{\varepsilon\,r,\perp}$ [20° C., 19 GHz]: | 0.0079 |
| | | $\eta$ [20° C., 19 GHz]: | 45.5 |

Example N26

| | | | |
|---|---|---|---|
| CPTU-5-S | 23.5% | T(N,I) [° C.]: | 173.5 |
| CPU(F,F)-3-S | 19.0% | $\tau$ [20° C., 19 GHz]: | 0.299 |
| CPUI-4-S | 12.5% | $\varepsilon_{r,\parallel}$ [20° C., 19 GHz]: | 3.46 |
| PTUI-4-S | 10.0% | $\varepsilon_{r,\perp}$ [20° C., 19 GHz]: | 2.43 |
| UIPTU-5-S | 15.0% | $\tan\delta_{\varepsilon\,r,\parallel}$ [20° C., 19 GHz]: | 0.0043 |
| PPTUI-4-S | 20.0% | $\tan\delta_{\varepsilon\,r,\perp}$ [20° C., 19 GHz]: | 0.0048 |
| $\Sigma$ | 100.0% | $\eta$ [20° C., 19 GHz]: | 62.9 |

Example N27

| | | | |
|---|---|---|---|
| PPTU-4-S | 6.0% | T(N,I) [° C.]: | 172.2 |
| PPTU-5-S | 12.0% | LTS bulk [h, -20° C.]: | 24 |
| PPU-TO-S | 23.0% | LTS bulk [h, -30° C.]: | 120 |
| CPTU-5-S | 25.0% | $\tau$ [20° C., 19 GHz]: | 0.323 |
| CPU(F,F)-3-S | 18.0% | $\varepsilon_{r,\parallel}$ [20° C., 19 GHz]: | 3.52 |
| CPU(F,F)-4-S | 6.0% | $\varepsilon_{r,\perp}$ [20° C., 19 GHz]: | 2.38 |
| UITU-4-S | 5.0% | $\tan\delta_{\varepsilon\,r,\parallel}$ [20° C., 19 GHz]: | 0.0045 |
| UITU-5-S | 5.0% | $\tan\delta_{\varepsilon\,r,\perp}$ [20° C., 19 GHz]: | 0.0067 |
| $\Sigma$ | 100.0% | $\eta$ [20° C., 19 GHz]: | 48.2 |

Example N28

| | | | |
|---|---|---|---|
| PTU-3-S | 5.0% | T(N,I) [° C.]: | 158.7 |
| PTU-5-S | 5.0% | LTS bulk [h, -30° C.]: | 72 |
| PPTU-4-S | 6.0% | $\tau$ [20° C., 19 GHz]: | 0.322 |
| PPTU-5-S | 12.0% | $\varepsilon_{r,\parallel}$ [20° C., 19 GHz]: | 3.58 |
| PPU-TO-S | 23.0% | $\varepsilon_{r,\perp}$ [20° C., 19 GHz]: | 2.43 |
| CPTU-5-S | 23.0% | $\tan\delta_{\varepsilon\,r,\parallel}$ [20° C., 19 GHz]: | 0.0050 |
| CPU(F,F)-3-S | 18.0% | $\tan\delta_{\varepsilon\,r,\perp}$ [20° C., 19 GHz]: | 0.0078 |
| UITU-4-S | 4.0% | $\eta$ [20° C., 19 GHz]: | 41.3 |
| UITU-5-S | 4.0% | $\tan\delta_{\varepsilon\,r,\parallel}$ [20° C., 19 GHz]: | |
| $\Sigma$ | 100.0% | | |

Example N29

| | | | |
|---|---|---|---|
| PPTU-4-S | 6.0% | T(N,I) [° C.]: | 156 |
| PPTU-5-S | 12.0% | τ [20° C., 19 GHz]: | 0.331 |
| PPU-TO-S | 20.0% | $\varepsilon_{r,\parallel}$ [20° C., 19 GHz]: | 3.65 |
| CPTU-5-S | 22.0% | $\varepsilon_{r,\perp}$ [20° C., 19 GHz]: | 2.44 |
| PTU-3-S | 10.0% | tan $\delta_{\varepsilon\, r,\parallel}$ [20° C., 19 GHz]: | 0.0052 |
| PTU-5-S | 10.0% | tan $\delta_{\varepsilon\, r,\perp}$ [20° C., 19 GHz]: | 0.0085 |
| CPU(F,F)-3-S | 10.0% | η [20° C., 19 GHz]: | 39.2 |
| UITPU-4-S | 10.0% | | |
| Σ | 100.0% | | |

The invention claimed is:

1. A compound of formula U

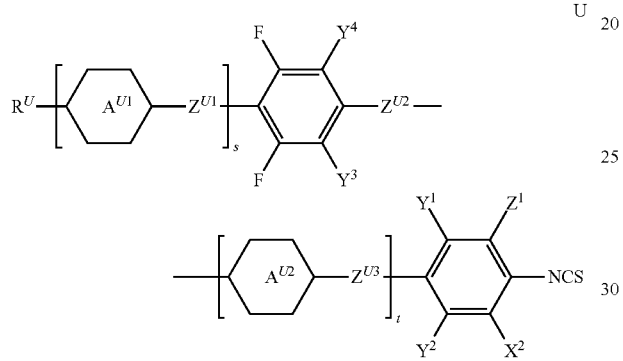

in which
R$^U$ denotes H, alkyl or alkoxy having 1 to 12 C atoms, or alkenyl, alkenyloxy or alkoxyalkyl having 2 to 12 C atoms, in which one or more CH$_2$—groups may be replaced by

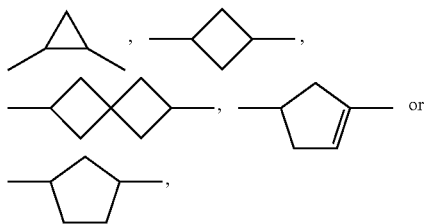

or a group R$^P$,
R$^P$ denotes halogen, CN, NCS, R$^F$, R$^F$—O— or R$^F$—S—, wherein
R$^F$ denotes fluorinated alkyl having 1 to 9 C atoms or fluorinated alkenyl having 2 to 9 C atoms,
Z$^{U1}$, Z$^{U2}$, Z$^{U3}$ identically or differently, denote —CH=CH—, —CF=CF—, —CH=CF—, —CF=CH—, —C≡C— or a single bond,
X$^1$, X$^2$ identically or differently, denote H, Cl, F, CH$_3$ or C$_2$H$_5$,
Y$^1$, Y$^2$, Y$^3$, Y$^4$ identically or differently, denote H, F, Cl, or straight chain alkyl, or alkoxy, each having 1 to 12 C atoms or straight chain alkenyl or alkenyloxy, each having 2 to 12 C atoms or branched or cyclic alkyl, alkenyl, alkoxy or alkenyloxy, each having 3 to 12 C atoms, where at least one of Y$^1$, Y$^2$, Y$^3$ and Y$^4$ is different from F,
s is 0, 1 or 2,
t is 0, 1 or 2, and
s+t is 0, 1 or 2,

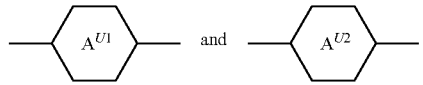

identically or differently, denote a radical selected from the following groups:

a) the group consisting of 1,4-phenylene, 1,4-naphthylene, and 2,6-naphthylene, in which one or two CH groups may be replaced by N and in which one or more H atoms may be replaced by L, b) the group consisting of trans-1,4-cyclohexylene, 1,4-cyclohexenylene, bicyclo[1.1.1]pentane-1,3-diyl, 4,4"-bicyclohexylene, bicyclo[2.2.2]octane-1,4-diyl, spiro[3.3]heptane-2,6-diyl, in which one or more non-adjacent CH$_2$ groups may be replaced by —O— and/or —S— and in which one or more H atoms may be replaced by F, and c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, SF$_5$ or straight-chain, in each case optionally fluorinated, alkyl, alkoxy, alkylcarbonyl, alkoxycarbonyl, alkylcarbonyloxy or alkoxycarbonyloxy having 1 to 12 C atoms or branched, in each case optionally fluorinated, alkyl, alkoxy, alkylcarbonyl, alkoxycarbonyl, alkylcarbonyloxy or alkoxycarbonyloxy having 3 to 12 C atoms.

2. The compound according to claim 1, wherein

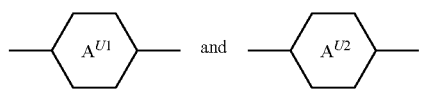

on each occurrence, independently of one another, denote

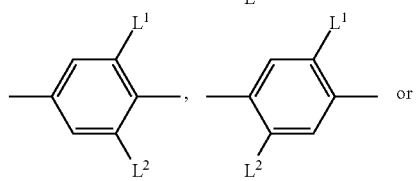

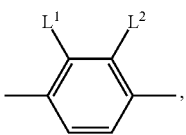

in which one or two CH-groups may be replaced by N, and wherein

alternatively denotes

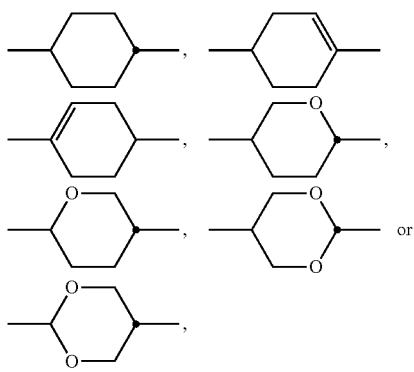

and

L¹ and L² identically or differently, denote F, Cl or straight chain alkyl having 1 to 12 C atoms or straight chain alkenyl having 2 to 12 C atoms or branched or cyclic alkyl or alkenyl each having 3 to 12 C atoms.

3. The compound according to claim 1, wherein $Z^{U1}$ and $Z^{U2}$, identically or differently, denote —C≡C— or a single bond.

4. The compound according to claim 1, wherein the compound is selected from the compounds of formulae U-1 to U-20

U-1
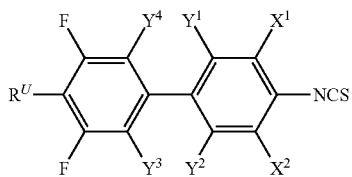

U-2
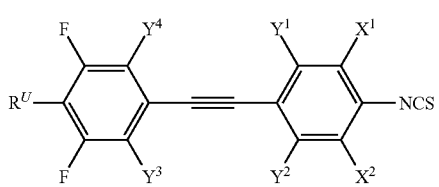

U-3
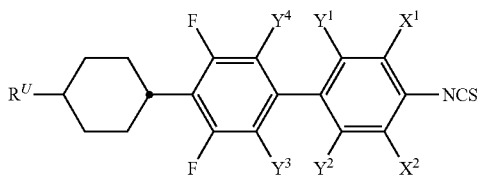

U-4
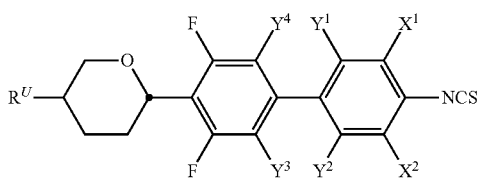

U-5
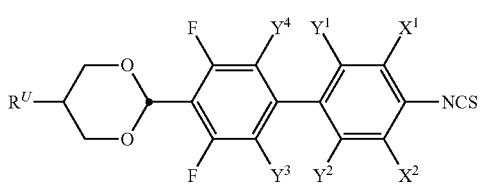

U-6
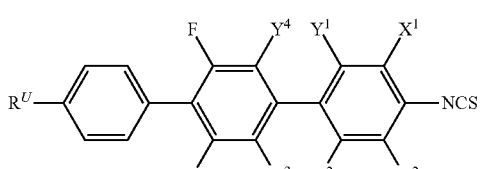

U-7
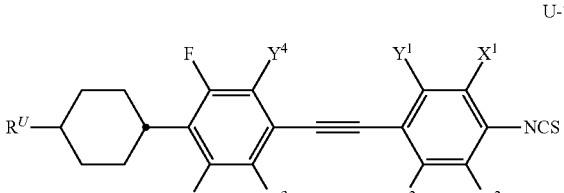

U-8
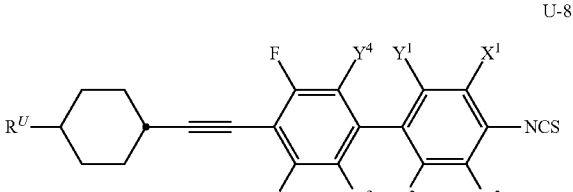

U-9
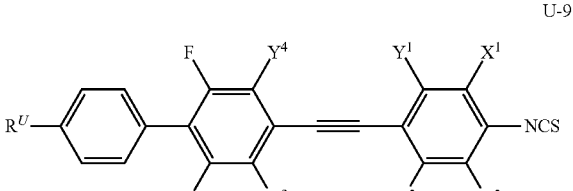

U-10
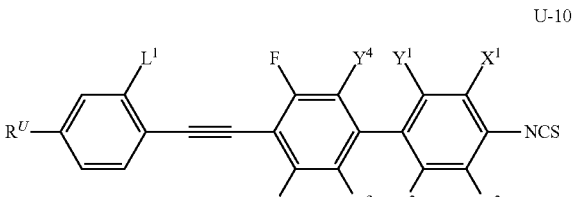

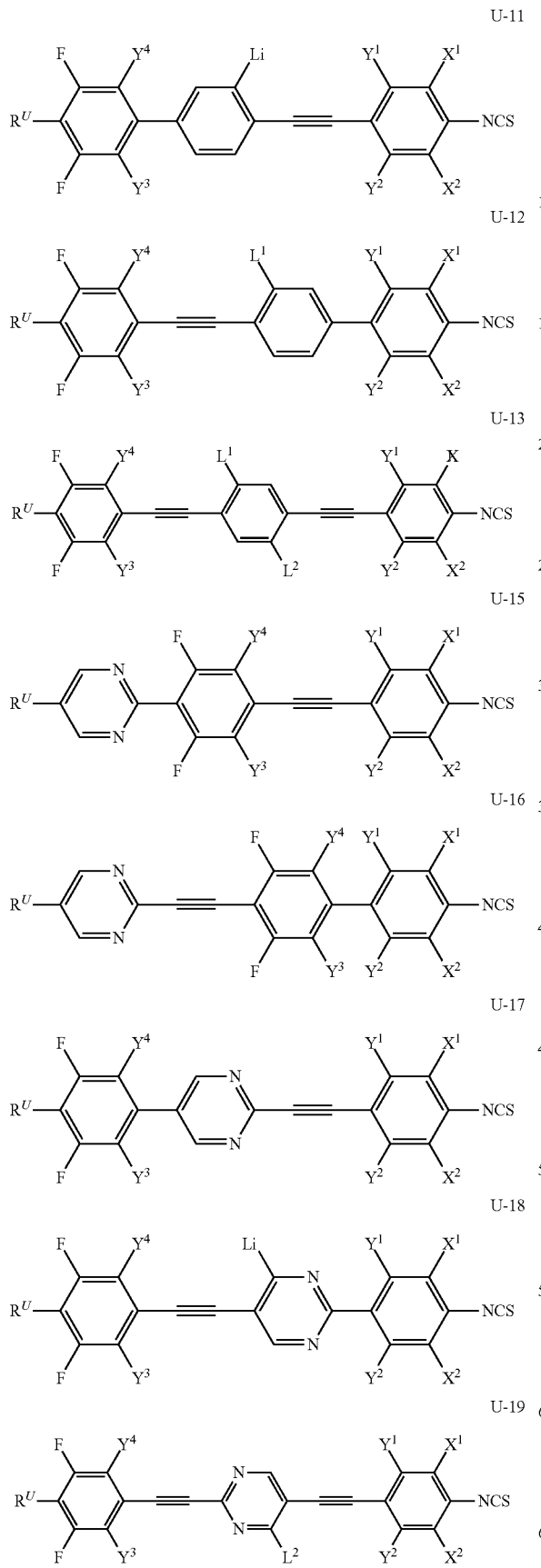

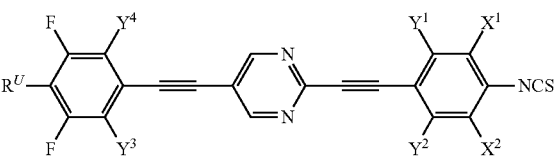

in which
L¹, L² identically or differently, denote H, F, Cl, methyl, ethyl, n-propyl, isopropyl, cyclopropyl, cyclobutyl, cyclopentyl or cyclopentenyl, and $R^U$, $X^1$, $X^2$, $Y^1$, $Y^2$, $Y^3$ and $Y^4$ have the meanings given for formula U.

5. The compound according to claim 1, wherein the radicals $X^1$ and $X^2$ denote H or F.

6. The compound according to claim 1, wherein the radicals $Y^1$, $Y^2$, $Y^3$, and $Y^4$, identically or differently, denote H, F, Cl, methyl, ethyl, n-propyl, isopropyl, cyclopropyl, cyclobutyl, cyclopentyl or cyclopentenyl.

7. The compound according to claim 1, wherein $R^U$ denotes alkyl having 1 to 12 C atoms.

8. The compound according to claim 1, wherein the group $R^U$ denotes $R^P$.

9. A liquid crystal medium comprising one or more compounds according to claim 1.

10. The liquid crystal medium according to claim 9, wherein the medium comprises one or more compounds selected from the group of compounds of formulae I, II and III,

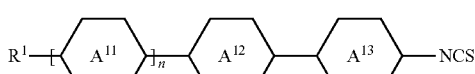

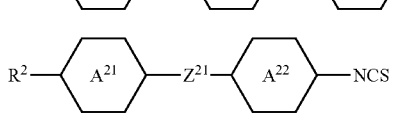

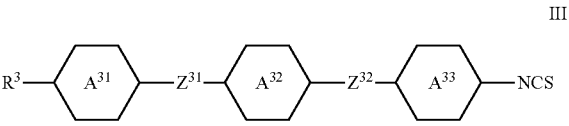

in which
R¹ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more CH₂- groups may be replaced by

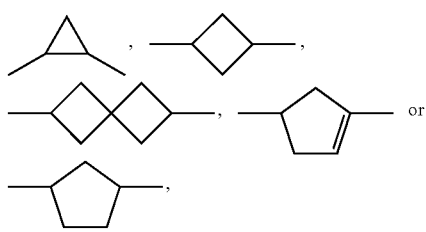

n is 0, 1 or 2,

or

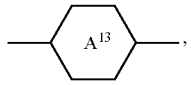

on each occurrence, independently of one another, denote

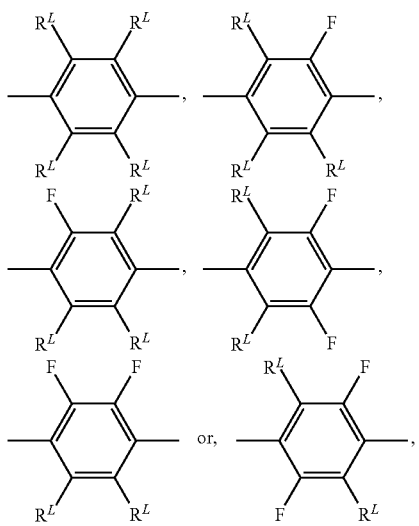

in which $R^L$, on each occurrence identically or differently, denotes H or alkyl having 1 to 6 C atoms, and wherein

alternatively denotes

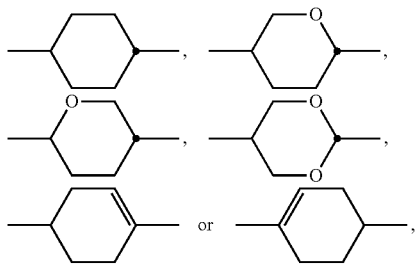

$R^2$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

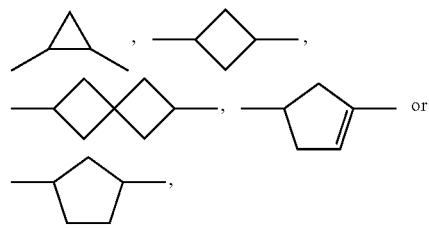

$Z^{21}$ denotes trans-CH=CH—, trans-CF=CF— or —C≡C—,

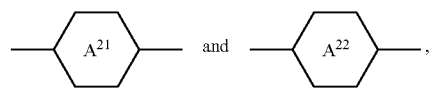

independently of one another, denote

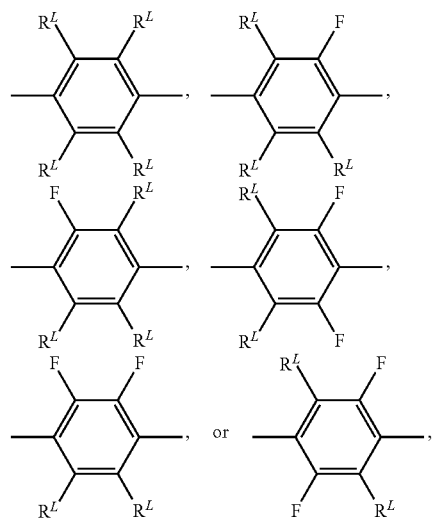

in which $R^L$, on each occurrence identically or differently, denotes H or alkyl having 1 to 6 C atoms;

$R^3$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

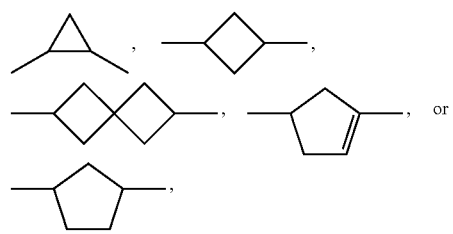

one of $Z^{31}$ and $Z^{32}$ denotes trans-CH=CH—, trans-CF=CF— or —C≡C— and the other one, independently thereof, denotes —C≡C—, trans-CH=CH—, trans-CF=CF— or a single bond, and

to

, independently of one another, denote

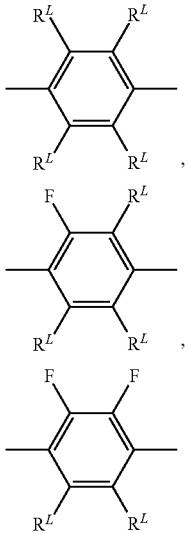 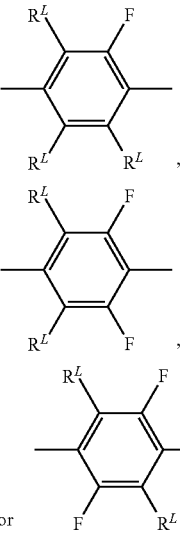

in which $R^L$, on each occurrence identically or differently, denotes H or alkyl having 1 to 6 C atoms, and wherein

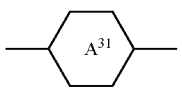

alternatively denotes

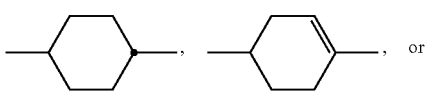

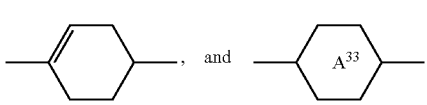

alternatively denotes

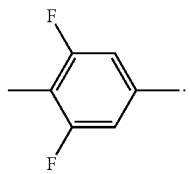

11. The liquid crystal medium according to claim 10, wherein the medium comprises one or more compounds selected from the group of compounds of formulae I-1 to I-5

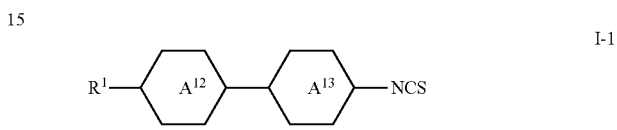

I-1

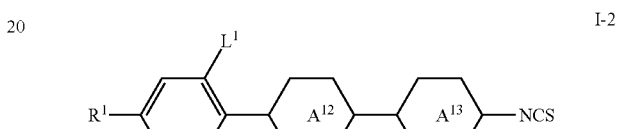

I-2

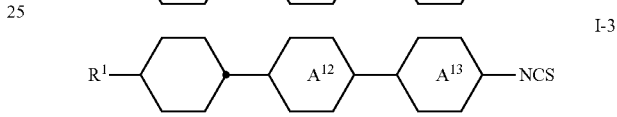

I-3

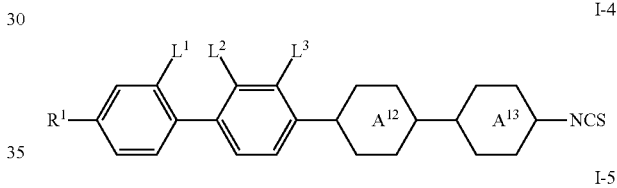

I-4

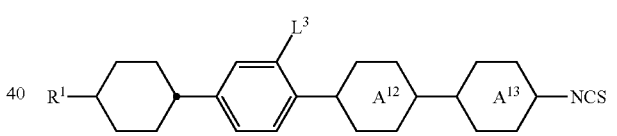

I-5 in which $L^1$, $L^2$ and $L^3$ on each occurrence, identically or differently, denote H or F, and $R^1$,

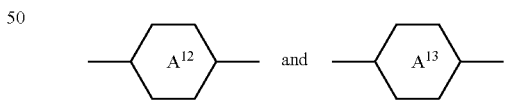

have the meanings given for formula I.

12. The liquid crystal medium according to claim 10, wherein the medium comprises one or more compounds selected from the group of compounds of formulae II-1 to II-3

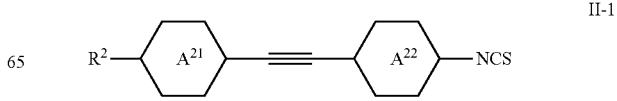

II-1

-continued

II-2
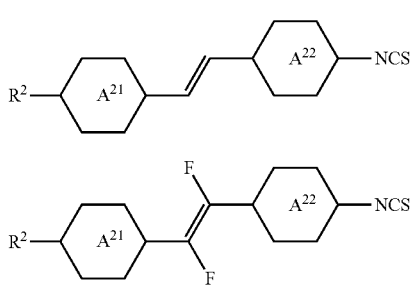

II-3 in which
R²,

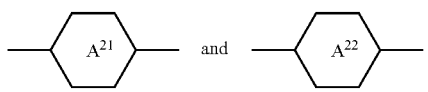

have the meanings given for formula II.

13. Liquid crystal medium according to claim 10, wherein the medium comprises one or more compounds selected from the group of compounds of formulae III-1 to III-6

III-1
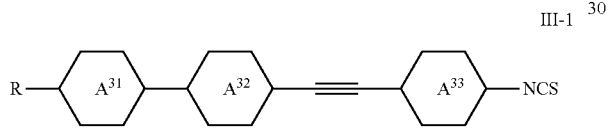

III-2
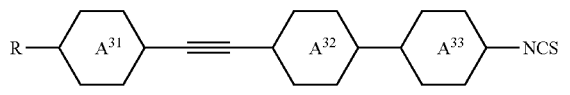

III-3
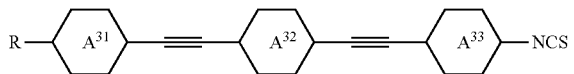

III-4
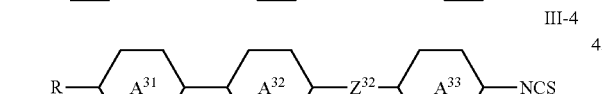

III-5
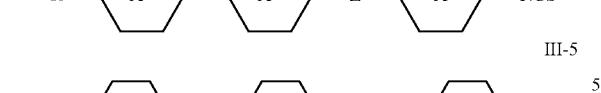

III-6
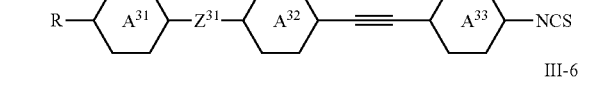

in which
R³,

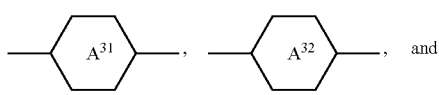

-continued

have the meanings given for formula III, and
Z³¹ and Z³² independently of one another, denote trans-CH=CH— or trans-CF=CF—, and in formula III-6 alternatively one of Z³¹ and Z³² may denote —C≡C—.

14. The liquid crystal medium according to claim 9, wherein the medium comprises one or more compounds of formula T T
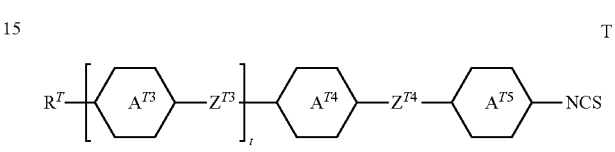

in which
$R^T$ denotes halogen, CN, NCS, $R^F$, $R^F$—O— or $R^F$—S—, wherein
$R^F$ denotes fluorinated alkyl having 1 to 12 C atoms or fluorinated alkenyl having 2 to 12 C atoms,

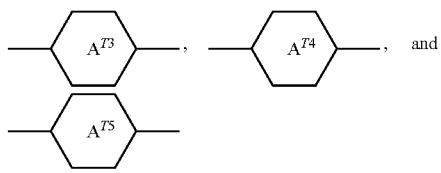

on each occurrence, independently of one another, denote

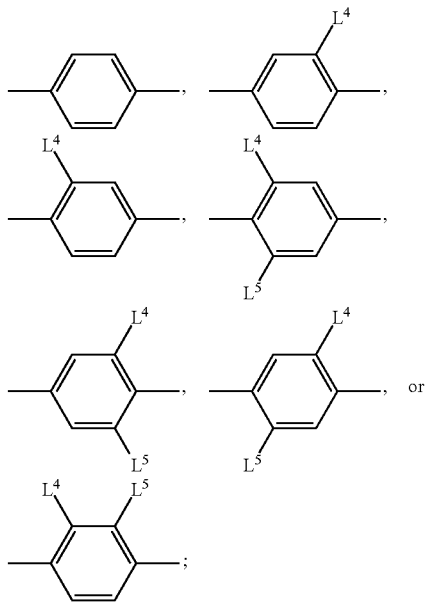

$L^4$ and $L^5$ identically or differently, denote F, Cl or straight chain alkyl having 1 to 12 C atoms or straight chain alkenyl having 2 to 12 C atoms or branched or cyclic alkyl or alkenyl each having 3 to 12 C atoms;

$Z^{T3}$, $Z^{T4}$ identically or differently, denote —CH=CH—, —CF=CF—, —CH=CF—, —CF=CH—, —C≡C— or a single bond, and t is 0 or 1.

15. A component for high-frequency technology, comprising the liquid crystal medium according to claim 9.

16. The component according to claim 15, wherein the component is a liquid-crystal based antenna element, a phase shifter, a tunable filter, a tunable metamaterial structure, a matching network or a varactor.

17. A microwave antenna array, comprising one or more components according to claim 15.

18. A liquid crystal medium comprising one or more compounds according to claim 4.

19. A component for high-frequency technology, comprising the liquid crystal medium according to claim 18.

20. The component according to claim 19, wherein the component is a liquid-crystal based antenna element, a phase shifter, a tunable filter, a tunable metamaterial structure, a matching network or a varactor.

* * * * *